(12) United States Patent
Dean et al.

(10) Patent No.: US 7,747,305 B2
(45) Date of Patent: Jun. 29, 2010

(54) COMPUTER-AIDED-DESIGN OF SKELETAL IMPLANTS

(75) Inventors: David Dean, Shaker Hts., OH (US); Kyoung-June Min, Beachwood, OH (US); Robert A. Ratcheson, Shaker Hts., OH (US)

(73) Assignee: Case Western Reserve University, Cleveland, OH (US)

( * ) Notice: Subject to any disclaimer, the term of this patent is extended or adjusted under 35 U.S.C. 154(b) by 438 days.

(21) Appl. No.: 11/299,138

(22) Filed: Dec. 9, 2005

(65) Prior Publication Data
US 2006/0094951 A1 May 4, 2006

Related U.S. Application Data

(63) Continuation of application No. PCT/US2004/018807, filed on Jun. 14, 2004.

(60) Provisional application No. 60/477,694, filed on Jun. 11, 2003.

(51) Int. Cl.
*A61B 5/00* (2006.01)

(52) U.S. Cl. .................. 600/407; 345/420; 345/620; 623/11.11; 623/16.11; 623/17.19; 623/23.64; 623/901; 703/11

(58) Field of Classification Search ............ 600/407, 600/410, 416, 425; 382/128, 131; 345/418–420, 345/581, 589, 619, 620, 625, 441, 442; 623/11.11, 623/16.11, 17.19, 23.64, 901; 703/1, 11
See application file for complete search history.

(56) References Cited

U.S. PATENT DOCUMENTS

| 5,522,019 A | * | 5/1996 | Bala et al. ............ 345/424 |
| 2002/0059049 A1 | * | 5/2002 | Bradbury et al. .......... 703/11 |

* cited by examiner

*Primary Examiner*—Ruth S Smith
(74) *Attorney, Agent, or Firm*—Tarolli, Sundheim Covell & Tummino LLP

(57) ABSTRACT

The present invention is directed to a computer aided design method for producing an implant for a patient prior to operation comprising the steps of: generating data with a non-invasive 3D (3-dimensional) scan of the patient's defect site that digitally represents the area that will receive the implant; designing and validating an implant on a computer based on digital data generated from a volume image of the patient; and fabricating the implant based solely on the implant design data generated on computer.

19 Claims, 18 Drawing Sheets

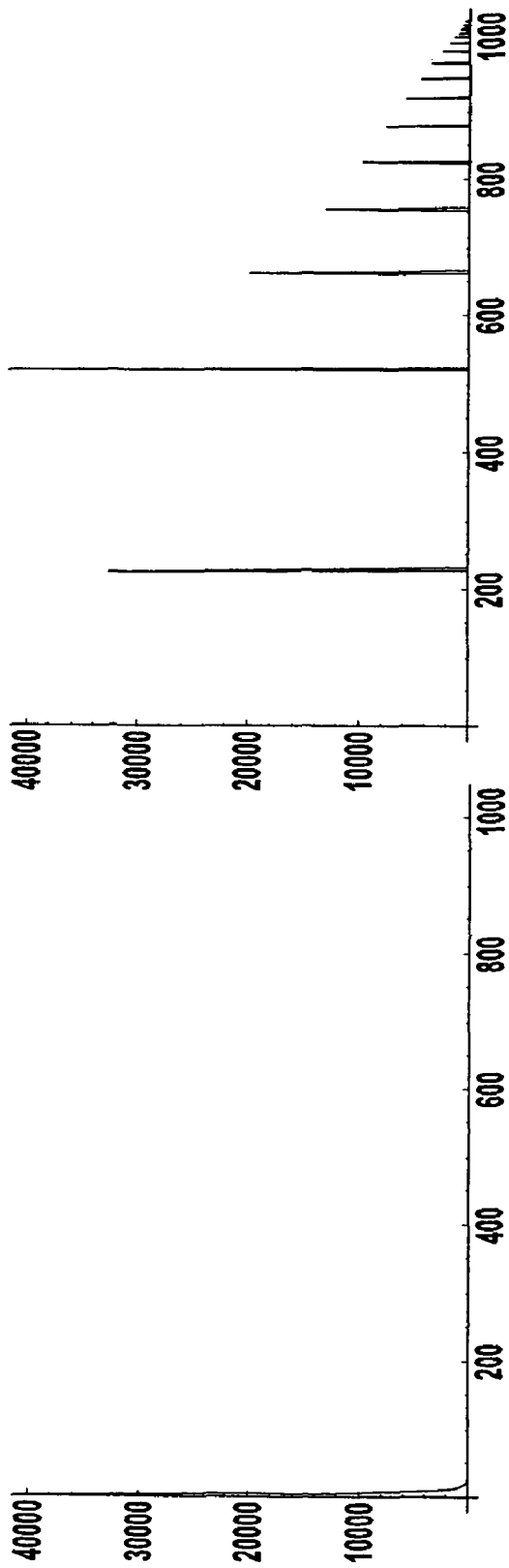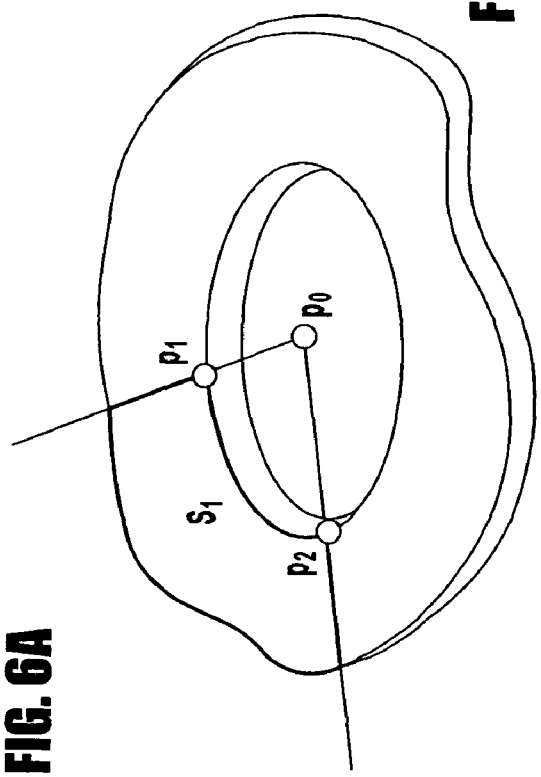

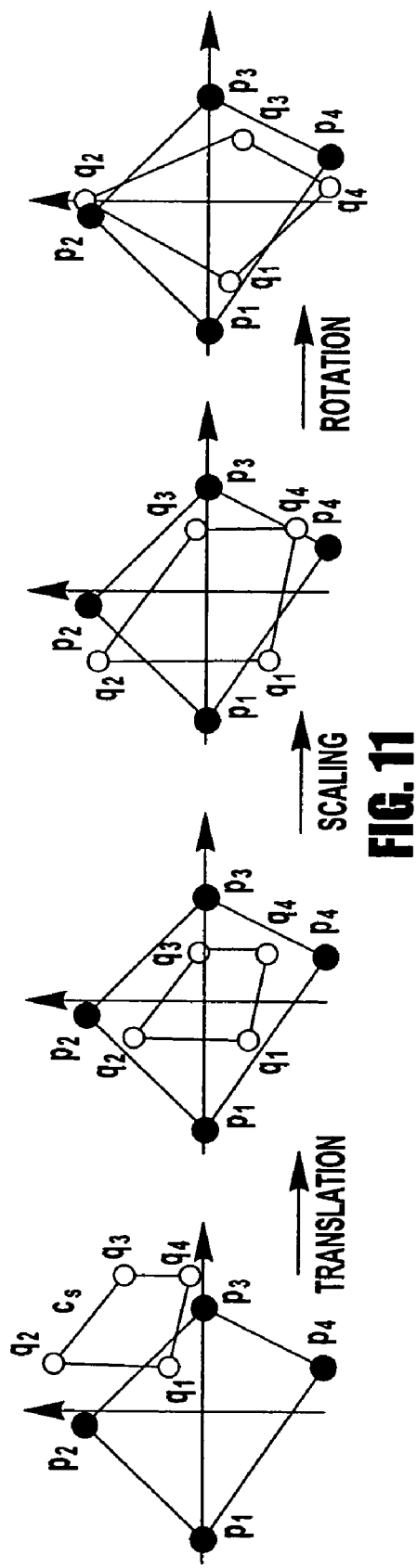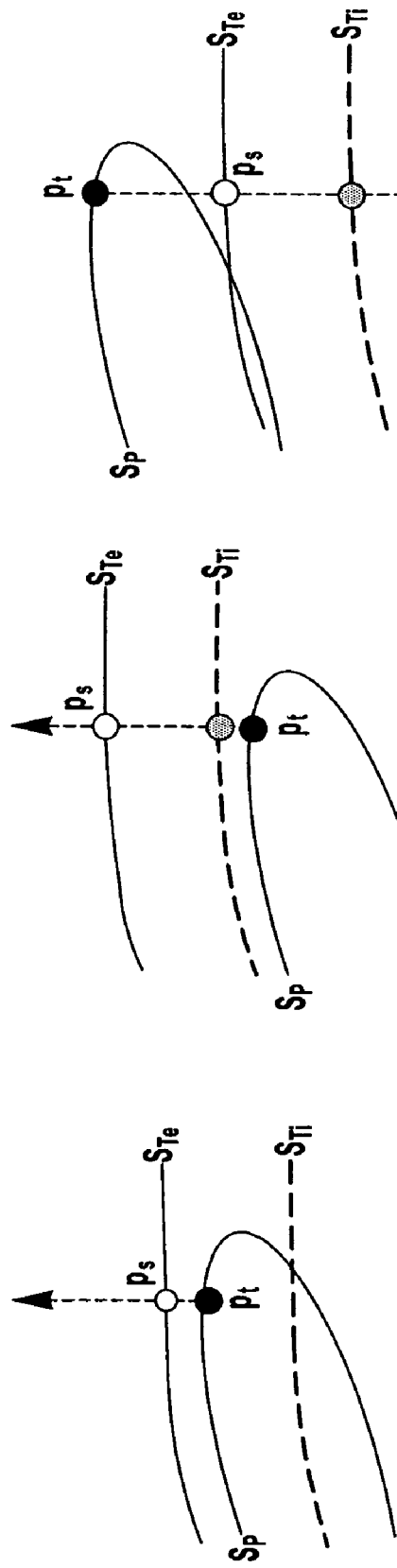

FIG. 22A  FIG. 22B  FIG. 22C  FIG. 22D

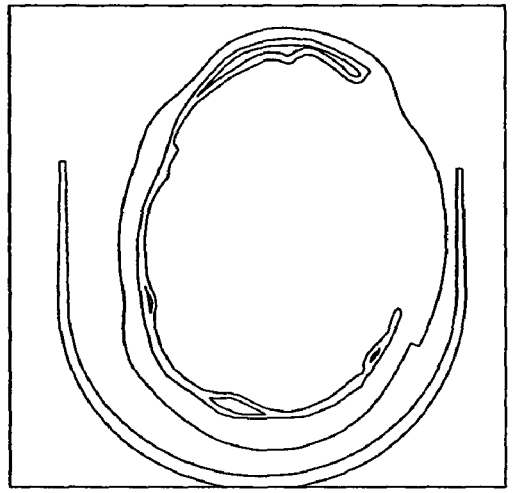 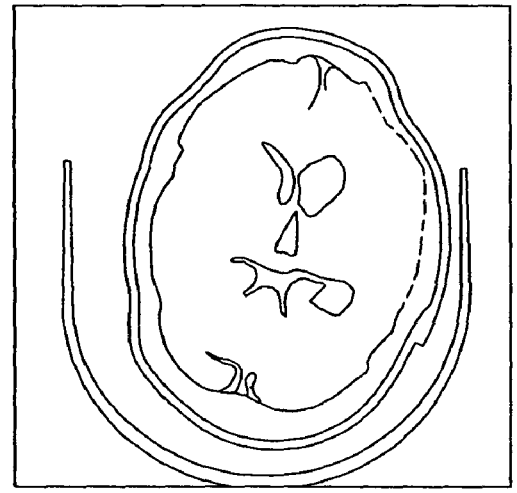
FIG. 25A  FIG. 25B
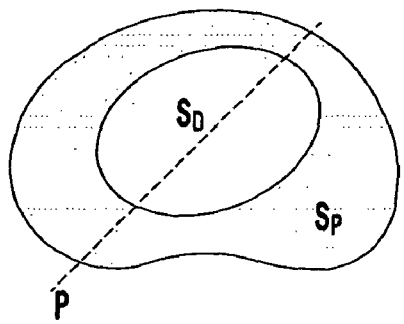 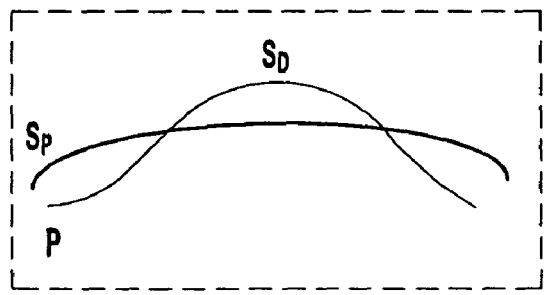
FIG. 26A  FIG. 26B
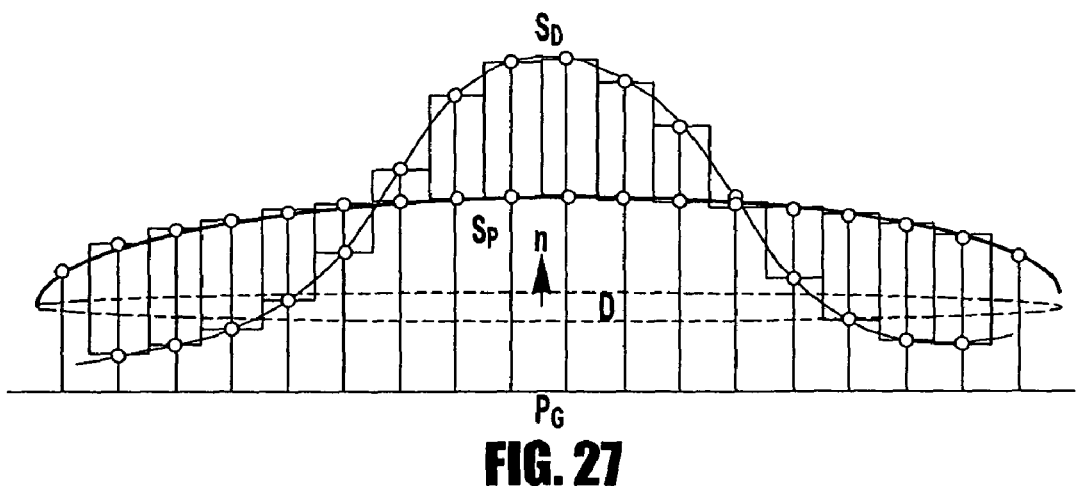
FIG. 27

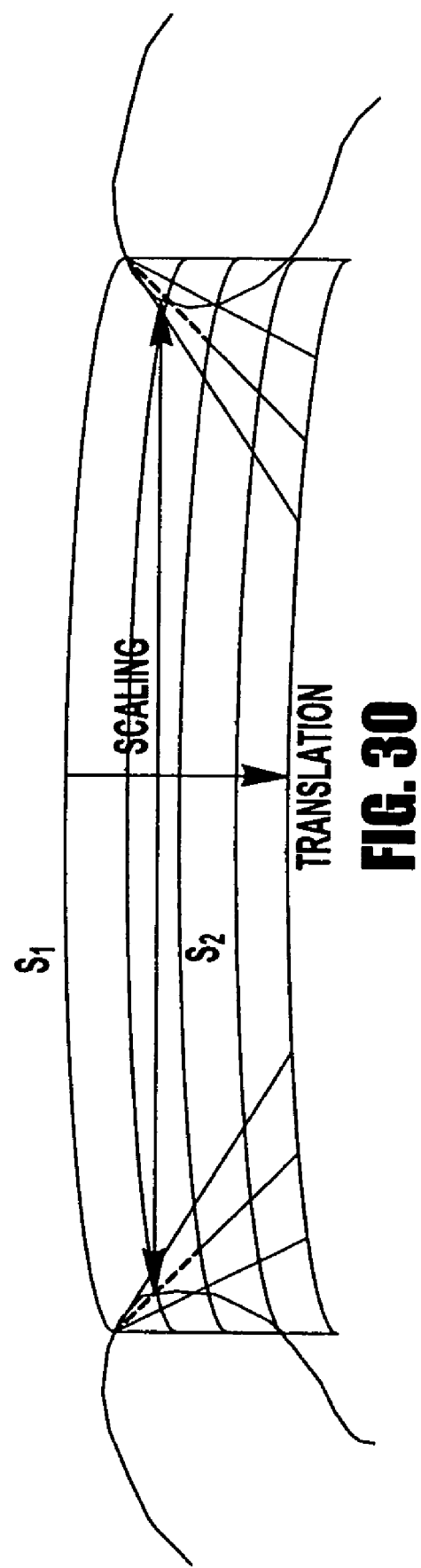

COMPUTER-AIDED-DESIGN OF SKELETAL IMPLANTS

CROSS-REFERENCE TO RELATED APPLICATIONS

This application claims the benefit of U.S. Provisional Patent Application No. 60/477,694 filed on Jun. 11, 2003 which is incorporated herein by reference.

This application is a continuation of copending PCT Patent Application No. PCT/US2004/018807 filed on Jun. 14, 2004, which is incorporated herein by reference.

TECHNICAL FIELD

The present invention generally relates to the generation of patient-specific, pre-operatively fabricated prosthetic implants and more particularly to a cranial implant.

BACKGROUND OF THE INVENTION

Large (>100cm$^2$) cranial defects require well-fitting prosthetic implants to protect the patient's brain from trauma or infection, and to restore an aesthetic shape to the patient's head. During the cranial reconstructive surgery referred to as cranioplasty, if sufficient cranial bone is not available for engraftment, then malleable and biocompatible materials are used to fashion an implant. The manual skill required of the surgeon, risk of the surgical procedure, cost to the patient, and length of the surgery all increase in proportion to the defect's size. Recently, high-resolution 3D computerized tomography (CT) has been shown useful as a basis for design and pre-operative fabrication of a cranial prosthetic, however design and production of a large, well-fitting implant is not a trivial task.

Traditional computer aided design (CAD) software is based on the use of constructive solid geometry (CSG) modeling. The CSG modeling paradigm formalizes the idea of combining a set of ideal geometric shapes, referred to as primitive solids, via regularized Boolean set operations (i.e., U*, ∩*, and -*) to fashion a desired shape. From this perspective, a CSG model is a tree having primitive solids as its leaves (i.e., leaves are nodes without child nodes) and regularized Boolean operations and geometric transformations as nodes of this tree. An example of a CSG tree representing a L-bracket object is shown in FIGS. 1A and 1B [Hoff 89] wherein: portion (a) is a dimensional specification of an L-bracket and portion (b) is the CSG tree representing a combination of three primitives (e.g., two boxes and a cylinder) via regularized Boolean operations that results in the L-bracket model.

These solids can be visually represented with predefined sets of vertices, edges, and polygons, referred to as a boundary representation (B-rep). By combining primitive solids such as cubes, spheres, or tori, a designer can gradually generate new models according to dimensional specifications. However, evaluating B-reps from a CSG solid without redundancy, and retaining topological validity of B-rep solids, usually requires computationally expensive calculation. CAD tools taking a CSG approach eventually attempt to mimic the designer's hand skills and sculpting tools, allowing drawings on canvas via combinations of CSG primitive solids on screen.

Other than a B-rep polygonal mesh, surfaces can also be represented parametrically as: Bezier, B-splines, and non uniform rational B-spline (NURBS) [FvFH 90, Watt 93]. Parametric surfaces require definitions with control and knot points, where each piece-wise curve segment passes through or affects the resulting shape. Sweeping operations on a parametric curve can define a parametric surface, however the tensor product of two parametric surfaces provides more control over the shape of freeform surfaces. Unlike 2D curve drawing tools, the direct manipulation of 3D parametric surfaces via control points is neither intuitive nor conducive to creating a complex freeform surface design. One alternative to direct manipulation is B-spline surface control point schemes derived from previously collected polygonal B-rep models. The conversion requires computationally expensive calculations to solve simultaneous linear boundary point and interior point equations [BaGr 80], which limit the possible degree of the surface complexity and accuracy. However, B-spline surfaces can be flexibly created using techniques such as hierarchical refining of B-spline patches [FoBa 88], and by automated conversion from arbitrary topological types [EcHo 96]. Thus, the traditional CAD approach can be considered as a bottom-up approach, starting with a set of primitives that are split or merged into more complex shapes at the root of a CSG tree [FIG. 1B].

Use of CAD/CAM in Medicine

Producing patient-specific CAD data for computer aided manufacture (CAM) implant production via rapid prototyping (RP) technology has extended the CAD/CAM area to medical imaging applications. The jaggy 'stair-case' artifacts seen in RP fabricated models previously due to low resolution-layered fabrication have been resolved by improved device resolution and various surface smoothing and refinement techniques [RaLu 96]. However, volumetric medical image data cannot be input directly into traditional CAD programs (i.e., software), programs that commonly require B-rep format objects. To convert a stack of CT volume data to a B-rep polygonal mesh surface, isosurface construction algorithms, such as Marching Cubes [LoCl 87] or the Wrapper [GuDe 94, GuHu 95] may be employed. The resulting B-rep is referred to as a 3D iso-intensity or isosurface image, where the surface corresponds to the boundary between structures with distinct radio-densities.

Recently, NURBS-based volume modeling was proposed as a means to represent not only the surface boundary but also the interior of medical CAD objects [MaLC 01a]. NURBS volume representations have an operational advantage over B-rep surfaces in terms of simplified Boolean CSG operations that avoid complex boundary problems. Nonetheless, NURBS volume data also require isosurface construction for RP printing since the de-facto standard file format for most current RP CAM (Computer Aided Manufacturing) is the stereolithography (STL) format, which describes a B-rep [MaLC 01b].

Most medical CAD research has been focused on the CAD/CAM of artificial hip and knee prosthetic implants. Recently, patient-specific hip implants have been an option added to the off-the-shelf implant designs produced by the traditional CAD approach. Patient-specific morphology includes hip implant stems that better fit when they are inserted into the bone marrow cavity of a patient's femur. Adams et al. [AHPK 02] suggest designing these patient-specific implants on the basis of femoral 3D CT scans with 2-5mm slice thickness. The resulting implant designs are then verified in a virtual implantation system evaluating anatomical parameters such as the amount of patient bone removal and femoral attachment contact surface location. Also, a hybrid CAD environment that supports direct parametric surface editing of high resolution CT volume images have been suggested by Viceconti et al. [VTGZ 01].

Use of CAD/CAM for Cranial Implants

Eufinger et al. [EuSa 01] claim that craniofacial structures require higher accuracy, therefore requiring use of larger image data sets than the femoral bone CT data utilized for implant design. They also note that interactive CAD processing of the requisite large image data files was not computationally possible until the 1990s. Cranial prosthetic implants must accurately fit the defect site in order to reduce the possibility of subsequent movement, dislodging, or extrusion [MaVa 90]. For this reason, early papers on patient-specific craniofacial implant fabrication suggest the use of a negative impression directly from the patient's exposed skull with vulcanizing silicon [MoPF 76].

The use of skull models obtained by RP from 3D CT data as a guide to manual implant production is computationally less expensive than a full CAD approach to implant design and fabrication. Several surgical supply companies have recently begun to produce solid plastic models of the patient's anatomy via RP techniques, such as stereolithography [SmBu 01, VoSA 20], based on 3D CT data. Modern RP systems produce models with accuracy up to 0.05 mm resolution[1], which exceeds the accuracy of conventional clinical CT data acquisition. A cranial prosthetic implant is then produced by manually molding plastic material on the surface of the 3D printed skull model. A negative impression (mold) is made of this hand-modelled implant, and this mold is then used to make a cast in implantable material. This method is known to produce better-fitting prosthetic implants than traditional CAD/CAM prefabrication methods. A clinical trial using this technique has reported 93.1% excellent intra-operative implant fit among 29 patients [SaHK 02]. These implants were cast in biocompatible materials such as CFRP (Carbon Fibre Reinforced Polymer) [SaHK 02], Polymethylmetacrylate (PMMA), or Proplast II [VoSA 20]. Although this method makes full use of computer algorithms to visualize and produce a 3D skull model, it is not, strictly, a CAD approach since the implant is manually sculpted by a skilled technician. RP produced skull models also have been found to be useful for preoperative diagnosis and surgical planning [SHZW 98].

[1]Viper si2 SLA system specification, 3D Systems©, Valencia Calif.

Irrespective of the accuracy, manually producing a cranial implant is an expensive process due to the cost of fabricating RP skull models and the time a board-certified anaplast or a prosthodont must bill to produce the implant. Usually the CAM systems are not in-house resulting in further delay [SmBu 01], and these implants cannot be exactly reproduced [WEKM 95]. Moreover, the absence of soft-tissue information removed during the skull segmentation process leading to an RP skull model raise risks of the improper fit of the implant due to unanticipated intersection with over- and under-lying soft-tissue layers, the scalp and dura mater, respectively [Bond 02].

An attempt to replace the manual design of an implant for unilateral cranial defect for one designed entirely on computer (i.e., Computer Aided Design, CAD) by reflecting the normal side of the cranium onto the defect side has been suggested by Linney and colleagues [LTRG 93]. Unfortunately, this technique cannot be applied to cases where the defect crosses over the mid-sagittal plane (i.e., a bilateral cranial defect) of the cranium. A concrete and practical CAD approach by Wehmöller et al. [WEKW 95] allows an operator to draw space curves and freeform surfaces with traditional CAD tools on the patient's skull image that is rendered as a stack of contours. The output data is then sent to a CNC milling machine to produce a solid titanium implant. Although their method may produce a reasonably fitting implant, the continuity of curvature across the surface at the implant-patient contact may be insufficient. This is because the resulting implant surface shape is derived solely from an operator's hand drawings that do not ensure a sufficient between-slice articulation of the contours. Carr et al. [CaFB 97] report a novel approach to cranial implant surface design using a surface interpolation method based on the TPS (Thin Plate Spline) radial basis function. Their work presents use of the TPS interpolation to deform an ideally thin planar surface to the defect site. Due to the high computational expense of the TPS interpolation method, they deferred use of this method until faster evaluation methods and increased computational capacity was-available. Their cranial implant shows an excellent continuity of surface curvature across the defect margin, benefiting from the property of the TPS interpolation.

Most CAD/CAM approaches to patient-specific cranial prosthetic implants have used titanium as the implant material for CNC milling machines [WEKW 95, CaFB 97, HFBL 98, JNRL 99, EuSa 01, KWSW 01]. The thickness specification of the titanium implants is usually chosen as 1.5 mm or less [EuSa 01]. This thin specification facilitates flexibility for designing the implant rim description, often with screw holes that partially overlap with cranial defect margin [JNRL 99]. Although this simplifies the CAD steps, the CAM phase of titanium processing can raise difficulties due to machining strength limits of many RP systems [WEKW 95]. A survey evaluating post-operative performance of CAD/CAM fabricated titanium cranial implants reports 76 out of 78 patients having successful outcomes [KWSW 01].

The primary problem preventing modeling of biomedical shapes using traditional CAD/CAM is the size of the original CT volume image and derived polygonal mesh image data sets. Most of current cranial implant CAD approaches need to partition the defect site during the design phase if the defect is as large [WEKW 95, CaFB 97] as those analyzed in this patent application. However, using anatomical models as primitives in a bottom-up CAD approach would require extremely expensive calculations for operations such as locating boundary intersections between hundreds of thousands of polygons. The traditional CAD approach of combining mathematical primitive models to design an implant may improve interactivity, but it also involves a significant amount of the designer's time for manual editing. Moreover, it may fail in maintaining fidelity to the inevitably complex patient-specific defect region dimensions. Thus, accurate 3D isosurface models derived from patient 3D-CT scans of the defect site should be utilized at the initial stage of the design process to guarantee sufficient implant accuracy (i.e., good fit) and performance (i.e., subsequent protection from trauma and infection).

ASPECTS OF THE PRESENT INVENTION

One aspect of the present invention is a computer aided design (CAD) software toolkit dedicated to designing large, well-fitting cranial prosthetic implants directly from the patient's 3D CT scan.

Another aspect of the present invention are CAD tools that would simulate a clinician's manual preparation of a cranial implant represented as a triangular mesh (i.e., B-rep) surface that fits a large cranial defect triangular mesh image obtained from a 3D CT-scan.

Still another aspect of the present invention is the accurate identification of the defect margin external surface boundary as a crestline.

Still another aspect of the present invention interpolation of a skull template to design the cranial implant surface where there is insufficient anatomy to utilize right-left symmetric mirroring.

Still another aspect of the present invention is a procedure for implant surface smoothing and partitioning from either a right-left mirrored (same patient), or full skull (different patient or an average), skull template.

Still another aspect of the present invention is the linking of the design of the prosthetic's edge and thickness to validation of non-overlap with the adjacent tissues, all done pre-operatively, prior to fabrication of the implant.

SUMMARY OF THE INVENTION

The design of patient-specific implants, and their production prior to surgery, is a difficult task with traditional computer aided design (CAD) tools. We present a CAD approach that utilizes three dimensional (3D) computerized tomographic-(CT) or volume-images (e.g. X-ray CT or magnetic resonance image data) for the design of prosthetic implants that are manufactured via a rapid prototyping (RP) device. The design process employs dedicated algorithms and starts with a verbose patient's 3D polygonal mesh image derived from 3D CT- or other volume-image data followed by four design stages: First, the external defect margin is identified as a crestline on the patient's polygonal mesh image. Detection of this crestline is assisted by a minimum-cost path searching-algorithm adapted from graph theory. The path traversal cost is primarily based on a principal curvature analysis. Second, either a left-right mirrored- or an average-organ template is interpolated into the defect site. The organ template deformation is driven by a two-pass thin plate spline (TPS) warp, first globally, then locally. Third, the organ template surface is regularly re-sampled and then smoothed using ray-surface collision detection and 2D low-pass image mask filtering. In addition, the portion of the organ template inside the patient image defect margin is partitioned from the rest of the organ template. Fourth, this prototype implant surface is validated by a check for non-intersection with adjacent patient tissues. If there are intersections, the prototype implant surface is modified if necessary. An internal implant surface, and a tapered surface connecting the internal and external implant surfaces, are interactively designed so as to insure appropriate implant-patient contact. This step results in a closed polygonal mesh surface that can be produced as a solid implant shape via an RP device. The design environment is interactive in real-time. The results from using the implants generated by the implant CAD system of the present invention have shown to be immediately clinically acceptable for the repair of defects in the human skull as well as extensible to: other bones, other organs, the outer surface of the body, or microscopic bodily structures.

According to the present invention, there is disclosed a computer aided design method for producing an implant for a patient prior to operation comprising the steps of: generating data with a non-invasive 3D (3-dimensional) scan of the patient's defect site that digitally represents the area that will receive the implant; designing and validating an implant on a computer based on digital data generated from a volume image of the patient; and fabricating the implant based solely on the implant design data generated on computer.

Further according to the present invention, the step of designing an implant based on the data generated from the 3D scan of a patient includes the steps of constructing a surface image representing a patient's defect site from 3D volume images.

Also according to the present invention, the step of generating data includes: defining a contour, describing the external boundary of the patient's defect site to receive the implant, on a surface image representing a patient's defect site that is derived from the 3D volume images in an accurate 3D space.

Still further according to the present invention, the step of designing an implant Further includes the steps of determining a 3D region of interest that includes only the region of the isosurface image immediately adjacent to the defect site; and clipping the 3D region of interest from the complete isosurface image.

Still further according to the present invention, the step of designing an implant further includes the steps of: placing a plurality of landmarks in order to seed the defect margin contour line on the isosurface image surrounding the defect margin.

Also according to the present invention, the step of designing an implant further includes the steps of: determining 3D surface curvature and traversal cost factors; and color mapping of the magnitude of the curvature at each 3D surface point.

Still further according to the present invention, the steps include redistributing the color values in an image referred to as a histogram over the entire intensity scale so as to make the contrast between low an high curvature regions visually useful.

Also according to the present invention, the steps include measuring the thickness of the patient's body structure underlying the defect margin crestline in order to determine its sufficiency for affixing the implant.

Also according to the present invention, the steps include resampling the defect-filling template surface to have uniformly shaped and spaced triangles; the use of these resampled manifolds for the accurate partitioning of a defect filling template image; and articulating the prototype implant surface while maintaining surface curvature continuity across the defect margin. The method also includes the step of using an implant surface smoothing algorithm that removes slice edge artifact when volume image slices have larger inter-slice than pixel dimensions.

Still further according to the present invention, the steps include validating the prototype implant surface and taper fit with adjacent bone and soft tissue structures prior to fabricating the implant using Rapid Prototyping production.

Also according to the present invention, the step of constructing the implant based on the data generated the 3D volume scan includes the steps of designing a full thickness 3D implant that articulates well with the defect site; validating that this implant design does not intersect adjacent tissues in the defect site; and designing an implant surface image that can be directly sent to a rapid prototyping device to print a full thickness implant from the data derived from the 3D scan and a template.

Still further according to the present invention, the steps include selecting the defect site from any portion of a person's body that is defective and requires an implant wherein the portion of the person's body is selected from the group comprising a skeletal element, a soft tissue organ, the external surface, and microscopic structures. The method includes the step of selecting a defect site from the skeletal element of a person's head.

According to the present invention, there is disclosed a computer aided design apparatus for producing an implant for a patient prior to operation comprising: means for gathering surface data (i.e., digital data) of the patient's defect site to receive the implant via non-invasive 3D volume imaging; means for designing with a computer (computer aided design) an implant based on the data generated from a 3D volume scan of the patient; and means for designing the implant based on the data generated by the 3D volume scan.

Also according to the present invention, there is disclosed a computer aided design wherein the means for constructing the implant based on the data generated the 3D volume scan includes means for inputting the data of the 3D volume (e.g., 3D CT) scan directly to a rapid prototyping device to print a full thickness implant.

Also according to the present invention the means for constructing an isosurface image representing a patient's defect site is from 3D volumetric images.

Still further according to the present invention, the computer aided design apparatus includes means for determining a 3D region of interest that includes only a region of the isosurface image immediately adjacent to the defect site; and means for clipping the 3D defect region of interest from the complete isosurface image.

Yet further according to the present invention, the computer aided design apparatus includes means for measuring the thickness of the body structure found internal to the crestline.

According to the present invention, there is disclosed a method of using a two pass warp to match a right-left mirrored or average template to the defect site, including: providing a two-pass warp, following an initial local positioning by least-squares fitting; providing a first pass warp based on globally defined bilateral and midline landmarks; and providing a second pass warp based on locally defined landmarks.

REFERENCES CITED

The following references are cited throughout the present specification and are identified by the code on the left of each reference.

[AHPK 02] Adam, F.; Hammer, D. S.; Pape, D.; Kohn, D. "Femoral anatomy, computed tomography and computer-aided design of prosthetic implants," *Arch. Orthop. Trauma. Surg.*, 122 (2002) 262-268.

[BaGo 88] Barry, P. J.; Goldman, R. N. "A recursive evaluation algorithm for a class of Catmull-Rom Splines," *Comput. Graphics (Proc. ACM Siggraph)*, 22 (1988) 199-204.

[BaGr 80] Barsky, B. A.; Greenberg, D. P. "Determining a set of B-spline control vertices to generate an interpolating surface," *Comput. Vision. Graphics*, 14 (1980) 203-226.

[Bond 02] Bond, A., Software Director of Osteoplastics Corp. *Personal Communication*, Cleveland, Ohio, 2002.

[Book 89] Bookstein, F. L. "Principal warps: Thin-plate splines and the decomposition of deformations," *IEEE T Pattern Anal.*, 11 (1989) 567-585.

[BoCu 88] Bookstein, F. L.; Cutting, C. B. "A proposal for the apprehension of curving craniofacial form in three dimensions," in *Craniofacial Morphogenesis and Dysmorphogenesis*, Ferrara, (Ed.), Center for Human Growth and Development, University of Michigan Press, Ann Arbor, Mich., 1988.

[CaFB 97] Carr, J. C.; Fright, W. R.; Beatson, R. K. "Surface interpolation with radial basis functions for medical imaging," *IEEE T. Med. Imaging.*, 16 (1997) 96-107.

[Case 96] Casey, J. *Exploring Curvature*, Vieweg Mathematics Press, Göttingen, Germany, 1996.

[CaRo 74] Catmull, E.; Rom, R. "A class of local interpolating splines," in *Computer Aided Geometric Design*, Academic Press, New York, 1974.

[CoLR 90] Cormen, T. H.; Leiserson , C. E.; Rivest, R. L. *Introduction to Algorithms*, MIT Press, Cambridge, 1990.

[CBDK 93] Cutting, C. B.; Bookstein, F. L.; Dean, D.; Kim, D. "A spline-based approach for averaging three dimensional curves and surfaces," in *SPIE Medical Imaging* 93, 2035-03, 29-44, SPIE, Bellingham, Wash., 1993.

[DBKL 98] Dean, D.; Bookstein, F. L.; Koneru, S.; Lee, J.-H.; Kamath, J.; Cutting, C. B.; Hans, M. G.; Goldberg, J. "Average African-American 3d-CT skull images: The potential clinical importance of ethnicity and sex," *J. Craniofac. Surg.*, 9 (1998) 348-358.

[DeMB 02] Dean, D.; Min, K. J.; Bond, A. "Computer aided design of pre-fabricated cranial plates," *J. Craniofac. Surg.* In Press, (2003)

[DMSB 99] Desbrun, M.; Meyer, M.; Schroder, P.; Barr, A. H. "Implicit fairing of irregular meshes using diffusion and curvature flow," *Comput. Graphics. (Proc. ACM Siggraph)*, (1999) 317-324.

[EcHo 96] Eck, M.; Hoppe, H. "Automatic reconstruction of B-Spline surfaces of arbitrary topological type," *Comput. Graphics. (Proc. ACM Siggraph)*, Proc. $23^{rd}$ Annual Conf. (1996) 325-334.

[EuSa 01] Eufinger, H.; Saylor, B. "Computer-assisted prefabrication of individual craniofacial implants," *AORN J.*, 74 (2001) 648-654.

[FvFH 90] Foley, J. D.; van Dam, A.; Feiner, S. K.; Hughes, J. F. *Computer Graphics: Principles and Practice*, Addison-Wesley Publishing Company, Massachusetts, 1990.

[FoBa 88] Forsey, D. R.; Bartels, R. H. "Hierarchical B-spline refinement," *Comput. Graphics (Proc. ACM Siggraph)*, 22 (1988) 205-212.

[GoWo 92] Gonzalez, R. C.; Woods, R. E. *Digital Image Processing*, Addison-Wesley Publishing Company, Massachusetts, 1992.

[GoLM 96] Gottschalk, S.; Lin, M. C.; Manocha, D. "OBB Tree: a hierarchical structure for rapid interference detection," *Comput. Graphics (Proc. ACM Siggraph)*, Proc. $23^{rd}$ Annual Conf. (1996) 171-180.

[GuDe 94] Quezeic, A.; Dean, D. "The wrapper: A surface optimization algorithm that preserves highly curved areas," in *Proc. Visualization in Biomedical Computing '94*, SPIE 2359-58, 631-642, SPIE, Bellingham, Wash. 1994.

[GuHu 95] Gueziec, A.; Hummel, R. "Exploiting triangulated surface extraction using tetrahedral decomposition," *IEEE T. Vis. Comput. Graphics*, 1 (1995) 328-342.

[HFBL 98] Heissler, E.; Fischer, F.; Bolouri, S.; Lehmann, T.; Mather, W.; Gebhardt, A.; Lanksch, W.; Bier, J. "Custom-made cast titanium implants produced with CAD/CAM for the reconstruction of cranium defects," *Int. J. Oral Maxillofac. Surg.*, 27 (1998) 334-338.

[HiCo 90] Hilbert, D.; Cohn-Vossen, S. *Geometry and the Imagination*, Chelsea Publishing Company, New York, 1990.

[Hoff 89] Hoffmann, C. H. *Geometric & Solid Modeling: An Introduction*, Morgan Kaufmann Publishers Inc., California, 1989.

[Hubb 90] Hubbard, P. M. "Constructive solid geometry for triangulated polyhedra", *Technical Report* CS-90-07, 1-21, Dept. of Computer Science, Brown University, Providence, R.I., 1990.

[JiTT 01] Jimenez, P.; Thomas, F.; Torras, C. "3D collision detection: a survey," *Comput. & Graphics*, 25 (2001) 269-285.

[JNRL 99] Joffe, J. M.; Nicoll, S. R.; Richards, R.; Linney, A. D.; Harris, M. "Validation of computer assisted manufacture of titanium plates for cranioplasty," *Int. J. Oral. Maxillofac. Surg.*, 28 (1999) 309-313.

[KWSW 01] Kamyszek, T.; Weihe, s.; Scholz, M.; Wehmöller, M.; Eufinger, H. "The reconstruction of cranial bone defects with individually prefabricated titanium implant: follow-up and evaluation of 76 patients with 78 titanium implants from 1994 to 1998 " *Mund-, Kiefer-und Gesichschirurgie*, 5 (2001) 233-238.

[KaWT 88] Kass, M.; Witkin, A.; Terzopoulos, D. "Snakes: Active contour models," *Int. J. Comput. Vis.*, 1 (1988) 321-344.

[LTRG 93] Linney, A. D.; Tan, A. C.; Richards, J.; Gardener, S.; Grindrod, S.; Moss, J. P. "Three-dimensional visualization of data on human anatomy: Diagnosis and surgical planning," *J. Audiov. Media Med.*, 16 (1993) 4-10.

[LoCl 87] Lorensen, W. E.; Cline, H. E. "Marching cubes: a high resolution 3d surface reconstruction algorithm," *Comput. Graphics. (Proc. ACM Siggraph)*, 21 (1987) 163-169.

[MaLC 01] Ma, D; Lin, F.; Chua, C. K. "Rapid prototyping applications in medicine. part 2: STL file generation and case studies," *Int. J. Adv. Manuf Technol.*, 18 (2001) 118-127.

[MaLC 01b] Ma, D; Lin, F.; Chua, C. K. "Rapid prototyping applications in medicine. part 1: NURBS-based volume rendering," *Int. J. Adv. Manuf Technol.*, 18 (2001) 103-117.

[MCVM 97] Maes, F.; Collignon, A.; Vandermeulen, D.; Marchal, G.; Suetens, P. "Multimodality image registration by maximization of mutual information," *IEEE T. Med. Imaging*, 16 (1997) 187-198.

[MaVa 90] Marsh, J. L.; Vannier, M. V. "Discussion of "computer-designed prostheses for orbitocranial reconstruction" by Tosh, Ellis and Steward," *Plast. Reconstr Surg.*, 71 (1990) 759-767.

[MoPF 76] Mohler, L. R.; Porterfield, H. W.; Ferraro, J. W. "Custom implants for reconstruction of craniofacial defects," *Arch. Surg.*, 111 (1976) 452-455.

[MoKY 01] Mokhtarian, F.; Khalili, N.; Yuen, P. "Curvature computation on free-form 3d meshes at multiple scales," *Comput. Vis. Image. Und.*, 83 (2001) 118-139.

[OhBB 01] Ohtake, Y; Belyaev, A.; Bogaevski, I. "Mesh regularization and adaptive smoothing," *Comput. Aided Design*, 33 (2001) 789-800.

[RaLu 96] Rajan, D. S.; Luo, R. C. "CAD model slicing and surface smoothing for building rapid prototyping parts," *Industrial Electronics, Control, and Instrumentation*, 1996., *Proc. 1996 IEEE IECON 22nd Int. Conf*, 1496-1501, Part 3, Taipei, Taiwan, 1996.

[RTEM 99] Richolt, J. A.; Teschner, M.; Everett P. C; Millis, M. B.; Kikinis, R. "Impingement simulation of the hip in SCFE using 3D models,". *Comput. Aided. Surg.*, 4 (1999) 144-151.

[Robb 95] Robb, R. A. Three Dimensional Biomedical Imaging, VCH Publishers, Inc., New York, 1995.

[Rohl 89] Rohlf, F. J. "Rotational Fit (Procrustes) Methods" in *Proc. of the Michigan Morphometrics Workshop*, Univ. Michigan Mus. Zoo., Ann Arbor, Mich., 1989.

[SHZW 98] Sailer, H. F.; Haers, P. E.; Zollikofer, C. P. E.; Warnke, T.; Carls, F. R.; Stucki, P. "The value of stereolithographic models for preoperative diagnosis of craniofacial deformities and planning of surgical corrections," *Int. J. Oral.* Maxillofac. Surg., 27 (1998) 327-333.

[SaHK 02] Saringer, W.; Nöbauer-Huhmann, N.; Knosp, E. "Cranioplasty with individual carbon fibre reinforced polymere (CFRP) medical grade implants based on CAD/CAM technique," *Acta Nurochir.*, 144 (2002) 1193-1293.

[SeSe 88] Segal, M.; Sequin, C. H. "Partitioning polyhedral objects into nonintersecting parts," *IEEE Comput. Graphics*, 8 (1988) 53-67.

[Shoe 95] Shoemake, K. "Linear form curves," in *Graphics Gems V*, Academic Press Inc., San Diego, Calif., (1995) 210-223.

[SmBu 01] Smith, D. G; Burgess, E. M. "The use of CAD/CAM technology in prosthetics and orthotics-current clinical models and a view to future," *J. Rehabil. Res. Dev.*, 38 (2001) 327-334.

[SoHB 99] Sonka, M.; Hlavac, V; Boyle, R. *Image Processing Analysis and Machine Vision*, Brooks/Cole Publishing Company, Pacific Grove, Calif., 1999.

[SuDe. 01] Subramanyan, K.; Dean, D. "A procedure to average 3D anatomical structures," *Med. Image Anal.*, 4 (2001) 317-334.

[Subr 00] Subramanyan, K. *Computer-Assisted Craniofacial Surface Apprehension and Representation*, Ph.D Thesis, Case Western Reserve University, Cleveland, Ohio, 2000.

[Tamp 92] Tampieri, F. "Newell's method for computing the plane equation of a polygon," in *Graphics Gems III*, Academic Press, Inc., San Diego, Calif., (1992) 231-232.

[Taub 95] Taubin, G. "A signal processing approach to fair surface design," *Comput. Graphics. (Proc. ACM Siggraph)*, (1995) 351-358.

[ThGo 93] Thirion, J. P.; Gourdon, A. "The marching lines algorithm: New result and proofs" , INRIA, *Rapport de recherche de l'INRIA*, RR-1881, Sophia Antipolis, 1993.

[Thir 94] Thirion, J. P. "Extremal points: Definition and application to 3D image registration", in *IEEE Conf. on Comput. Vis. and Pattern Recogn.*, 587-592, Seattle, Wash., 1994.

[Thom 63] Thomson, D. W. *On Growth and Form*, University Press, Cambridge, 1963.

[VTGZ 01] Viceconti, M.; Testi, D.; Gori, R.; Zannoni, C.; Cappello, A.; Lollis, A. D. "HIDE: a new hybrid environment for the design of custom-made hip prosthesis," *Comput. Meth. Prog. Bio.*, 64 (2001) 137-144.

[VoSA 00] Voigt, M.; Schaefer, D. J.; Andree, C. "Three-dimensional reconstruction of a defect of the frontozygomatic area by custom made Proplast II implant," *Eur. J. Plast. Surg.*, 23 (2000) 391-394.

[VoMM 99] Vollmer, J.; Mencl, R.; Muller, M. "Improved Laplacian smoothing of noisy surface meshes," *Comput. Graphics Forum*, 18 (1999) 131-138.

[Watt 93] Watt, A. *3D Computer Graphics*, Addison-Wesley Publishing Company, Massachusetts, 1993.

[WEKM 95] Wehmöller, M.; Eufinger, H.; Kruse, D.; Maßberg, W. "CAD by processing of computed tomography data and CAM of individually designed prostheses," *Int. J. Oral Maxillofac. Surg.*, 24 (1995) 90-97.

[Wern 94] Wernecke, J. *The Inventor Mentor: Programming Object-Oriented 3D Graphics with Open Inventor™*, Release 2, Addison-Wesley Publishing Company, New York, 1994.

| GLOSSARY | |
|---|---|
| CT | computed tomography (in this case X-ray CT) |
| CAD | Computer aided design |
| CSG | Constructive solid geometry |
| B-rep | Boundary representation |
| CAM | Computer aided manufacture |
| CNC | Computer numerical control |
| RP | Rapid prototyping |
| CFRP | Carbon Fiber Reinforced Polymer |

-continued

GLOSSARY

| | |
|---|---|
| 3D | Three dimensional |
| ROI | Region of interest |
| Cranial Defect Margin CWRU-103us | A space curve that represents the external edge of the defect site |
| Defect Site | Any portions of a persons body that is defective and requires an implant |

BRIEF DESCRIPTION OF THE DRAWINGS

The structure, operation, and advantages of the present invention will become further apparent upon consideration of the following description taken in conjunction with the accompanying figures (FIGS.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

FIGS. 6A-6B shows an Operational Curvature Histogram Equalization in accordance with the present invention;

FIG. 7 shows Sector $S_1$ in accordance with the present invention;

FIG. 11 shows a Procrustes Superimposition Method in accordance with the present invention;

FIG. 12A-12C shows local point correspondence during the detection of the Defect Margin Region in accordance with the present invention;

FIGS. 22A-22D shows three patch elements representing the possible triangle partitioning scenarios in accordance with the present invention;

FIGS. 25A-25B shows the dura mater surface segmentation in accordance with the present invention;

FIGS. 26A-26B shows significant collisions using the collision detection algorithm in accordance with the present invention;

FIG. 27 shows the volume estimation of dura mater penetrated by the first draft of the implant shape and also sub-implant space that is available to accommodate the dural sac owing to compression of the intersected portion were the implant to be pressed on top of it in accordance with the present invention;

FIG. 30 shows determination of implant thickness and taper in accordance with the present invention.

DETAILED DESCRIPTION OF THE PRESENT INVENTION

Figure 1B:
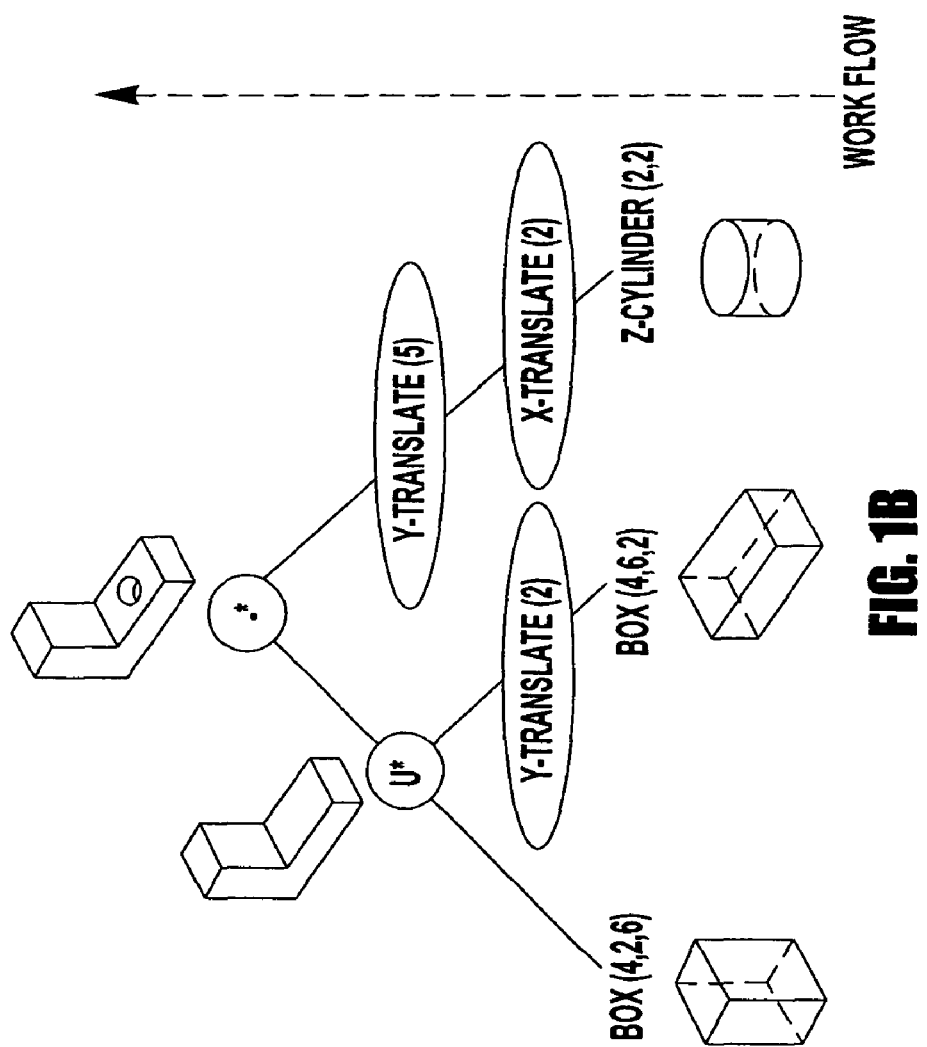
FIG. 1B is a CSG Tree Representation in accordance with the prior art.
Figure 1A:
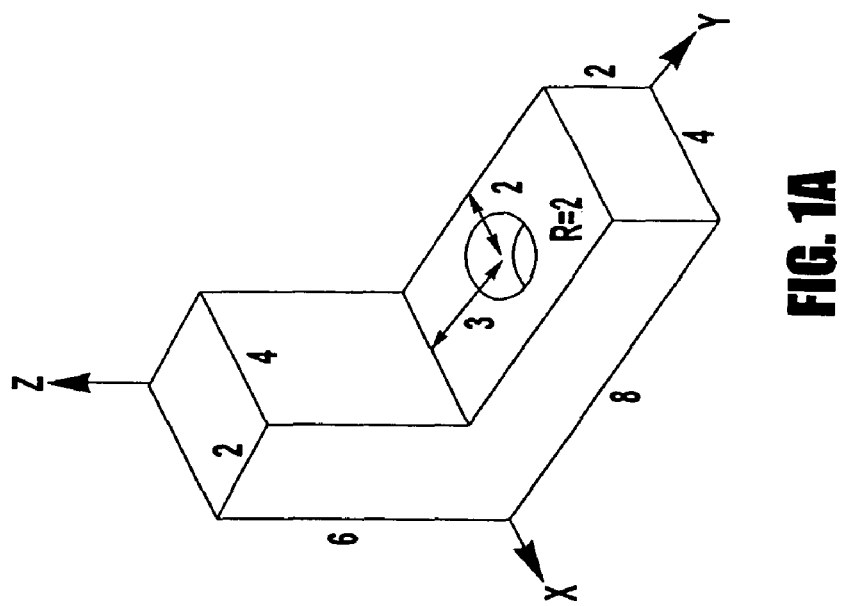
FIG. 1A is a dimensional specification of a L-bracket in accordance with the prior art.
Figure 2:
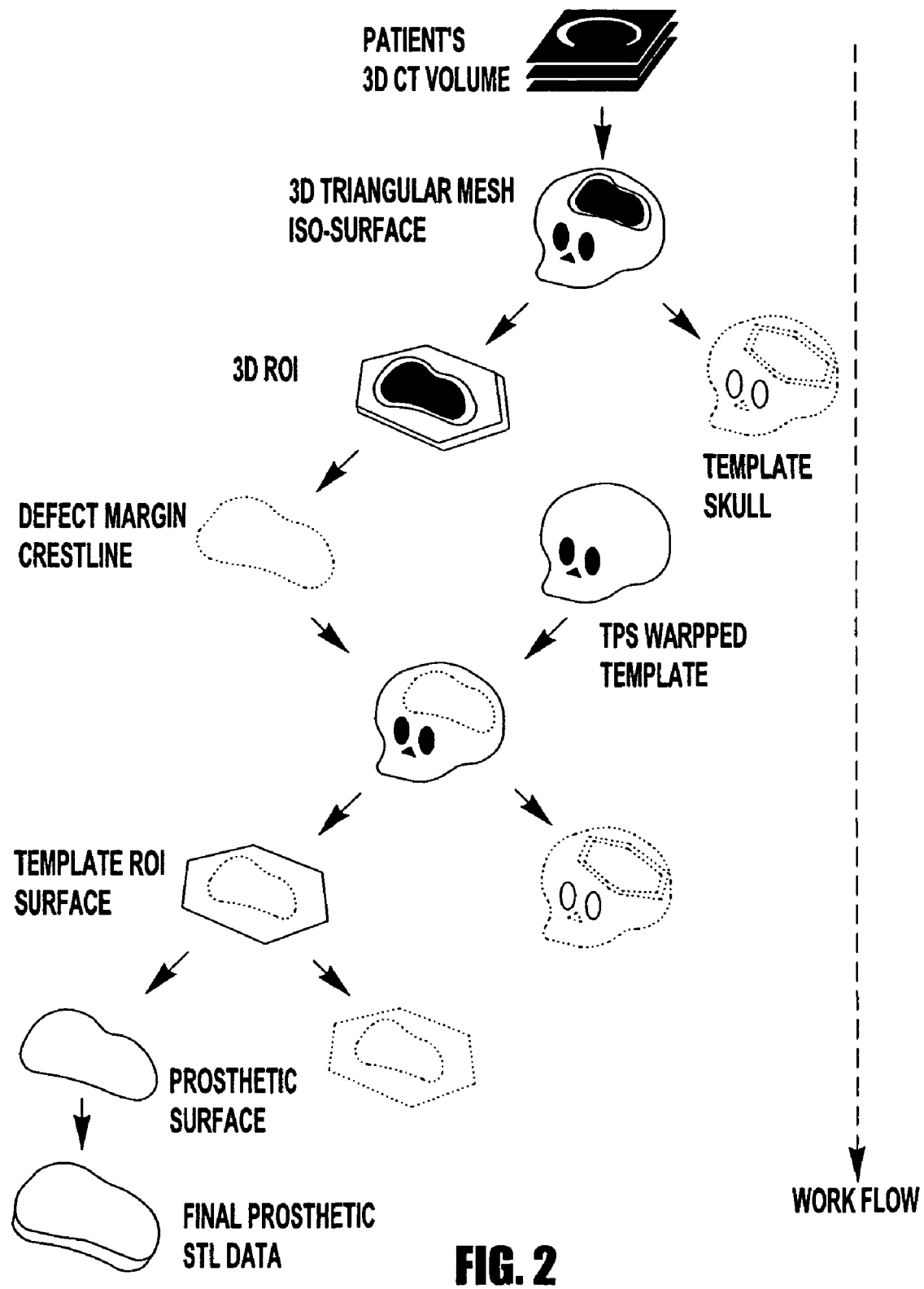
FIG. 2 is a proposed Top-down Medical CAD Approach in accordance with the present invention.

According to the present invention, instead of the traditional bottom-up CAD approach (FIG. 1B), a top-down approach for cranial prosthetic implant CAD/CAM. Specifically, the CAD work begins with a verbose B-rep (i.e., boundary representation) of the patient's CT-derived cranial isosurface that results in an implant represented on computer as a relatively simple B-rep, as shown in FIG. 2. FIG. 2 shows a proposed top-down medical CAD approach. Starting with verbose patient 3D CT data, a simple B-rep fitting the cranial defect is obtained. Only the required features are extracted from the initially large and complex data set. The full skull model is disposed to maximize efficiency during subsequent operations.

This CAD approach present is serially organized to achieve the objectives presented in Table 1.1:

TABLE 1.1

1) Accurate identification of the defect margin crestline.
2) Cranial implant surface interpolation via skull template deformation.
3) Implant surface smoothing and partitioning from the full skull template.
4) Prosthetic edge and surface fit validation prior to fabrication.

A contour in 3D space describing a cranial defect (hole) is referred to as the cranial defect margin crestline or cranial defect margin space curve. This is the outer-most limit of the location where the cranial implant is seated and attached to the patient's skull. The final cranial prosthetic implant CAD data will be converted to STL data format, which is a de facto standard RP object file format [MaLC 01b]. However, the discussion herein will center on CAD methods utilizing full resolution patient data for the design of a B-rep implant object that can be input directly to a RP device such as a stereolithographic (3D Systems, Valencia, Calif.) 3D printer.

The present invention is described in terms of defining a Defect Site of a person's body. The defective site is any portions of a persons body that is defective and requires an implant. While the present invention is described within terms of providing a cranial prosthetic implant which perfectly fits into the defect margin crestline of an opening in a patient's skull, it is equally applicable to create an implant for any part of a person's or animal's body.

The present invention is a CAD/CAM approach to patient-specific cranial implant production which reduces the production time and the cost of prefabrication. It eliminates the most recent process of generating expensive and redundant RP production of intermediate skull models from a patient 3D CT-scan, thereby reducing the design-phase from days to hours. This process also eliminates the standard-of-care procedure whereby the surgeon manually produces an implant intra-operatively and saves the risk of the patient enduring that procedure. Implant fit verification will reduce the risk of a CAD, patient-specific, pre-operatively fabricated implant not fitting during cranial reconstructive surgery. Although a thin titanium sheet could be chosen, the preferred material, currently, for the cranial implant would be the biocompatible plastic Polymethylmetacrylate (PMMA) or Proplast II. It is anticipated that fully or partially resorptive materials will soon be available for this procedure.

In this invention, a contour in 3D space describing the external boundary of the patient's cranial defect (hole) will be defined as the defect margin crestline or cranial defect margin space curve. This is the outer-most limit of the location where a cranial implant is seated and attached to a patient's skull. However, this application is particularly directed to CAD methods utilizing full resolution patient data for the design of a B-rep implant object. The full resolution patient data that can be input directly to a RP device such as a stereolithographic 3D printer in order to print a full thickness implant that protects the underlying brain from trauma and infection.

Cranial Defect Margin Crestline Identification

According to the present invention, a computer-aided method is used for identifying a cranial defect margin on a B-rep skull isosurface image (i.e., most commonly a triangulated polygonal manifold or meshwork surface). Isosurfaces representing a patient's skull can be constructed from 3D CT volumetric images via either the Marching Cubes algorithm [LoCl 87] or Wrapper algorithm [GuDe 94]. The term cranial defect margin refers to a space curve that represents the outer-most extent of the defect site. The cranial defect margin is used to define the rim of the implant as a space curve. The cranial defect margin is assumed to be the edge of a hole, which can be modeled as a closed contour in 3D space. Specifically, the cranial defect margin is represented as a set of 3D points (multiples of x, y, and z positions) that are sequentially ordered in a clockwise or counter-clockwise direction. By serially connecting these points into linear segments, an approximated cranial defect margin space curve is defined. The cranial defect margin is iteratively used throughout subsequent cranial prosthetic implant design processes.

Similar to the notion of a 2D region of interest (ROI) used in image processing, the notion of a 3D ROI is used. The 3D ROI includes only the region of the isosurface image immediately adjacent to the skull defect. Clipping the 3D ROI from the complete skull isosurface image significantly reduces the search space for subsequent analyses, and therefore facilitates more rapid interactive manipulation of the image during the implant design process.

The most intuitive means of extracting the location of the cranial defect margin is to have an operator directly draw a connected family of space curves around the defect site on the skull image. But unlike 2D images, 3D renderings taken from a single eye point may be insufficient for, or misleading to, the implant designer. Rather than providing an effective drawing tool, the cranial defect margin is algorithmically detected. In some sense, this approach is similar to that of the original active contour model image algorithm referred to as "snakes" [KaWT 88]. The snakes active contour model algorithm uses the notion of minimum internal and external energy functions to assist in the automated location of a contour-shape boundary in an intensity image. The boundary detection process is used as a model in an optimization problem initiated by an operator's interactive seeding of points on the surface of the skull image. In addition, detection of a closed contour is guaranteed as compared with the active contour model where a closed contour is not guaranteed.

One can usually find a sharp edge at the outer surface of a skull defect that may be considered as a crestline, where the sharpness is due to the edge dropping from the external skull surface into the cranial defect. Based on this observation, the cranial defect margin is characterized as a closed contour crestline. Geometrically, crestlines correspond to successive loci of the surface whose principal curvature is locally maximal [Thir 94]. This property is utilized in Thirion and Gourdon's Marching Lines algorithm [ThGo 93] for automatic detection of anatomical crestlines [BoCu 88] using principal curvature calculations in volumetric medical images. Although this algorithm extracts anatomic crestlines without any operator interaction, it cannot guarantee that the resulting space curve is a continuously closed contour. Moreover, the principal curvature estimation method employed in this algorithm requires the partial derivatives from neighboring voxels, which would have to be back projected from vertices composing a polygonal mesh. Instead of this computationally expensive strategy, Mokhtarian et al. [MoKY 01] proposed curvature estimation on a free-form polygonal mesh based on approximated rectangular grids referred to as semi-geodesic coordinates. Unfortunately, their method describes estimation of only Gaussian and mean curvatures, excluding principal curvature. Thus, to evaluate principal curvature at arbitrary points of an isosurface, a new metric is presented, termed "principal operational curvature."

When the range of curvature is properly sampled on the isosurface image, then it may be converted to color texture information and mapped on the image. This should reveal the location of the cranial defect margin crestline by discriminating the crestline with visually distinctive color signals. However, in practice, it is common to find extremely sharp, but irrelevant artifacts that skew the curvature range. Therefore, a histogram equalization [GoWo 92, SoHB 99] technique is employed to redistribute the histogram of normalized original operational curvature color coding, thereby enhancing contrast in the curvature map for visualization purposes. This improved curvature map will guide the operator to put seed landmarks on the candidate points of the cranial defect margin crestline that will sufficiently guide the automated detection of the cranial defect margin crestline.

An optimization approach is used to complete detection of the cranial defect margin crestline by modeling the polygonal mesh isosurface image as an undirected graph. Upon the basis of the operational curvature estimation and other estimated geometric parameters, a consecutive minimum-cost path [CoLR 90] is found in the graph that corresponds to the cranial defect margin crestline. General 3D ROI Clipping To acquire the 3D ROI, the operator interactively places landmarks on the surface surrounding the cranial defect margin. The operator attempts to preserve at least 1.0 cm of surface outside of the cranial defect margin to insure capturing a sufficient amount of data for subsequent analyses. Once a closed border is formed, a clipping operation extracts the 3D-ROI from the rest of the skull isosurface image.

The 3D ROI clipping algorithm assumes that the defect is located entirely within a hemisphere of the cranium that can be approximated as a sphere. In Table 2. 1, the 3D ROI clipping algorithm is summarized.

TABLE 2.1

3D ROI Clipping Algorithm:

1. Put index of all vertices into array A[1:n].
2. Find the best fitting plane for the seed landmarks, $p_i$ [FIG. 3A].
3. Reorient the skull so that the normal vector, $n_b$, of the best-fitting plane is aligned with the Z-axis [FIG. 3B].
4. Eliminate indices of vertices in A within negative Z-axis (dark area).
5. Project the remaining indices in A and the seed landmarks onto the XY-plane.
6. Define a line equation between two consecutive landmarks, and perform a test on each vertex to see if it satisfies an inequality for being inside the border in the XY-plane as shown in FIG. 3C. This step requires a convex surface.
7. Leave only the vertices that satisfy step 6, and then iterate for all adjacent landmark pairs in sequence until the ROI cutting contour is closed.
8. Extract triangle information using a bit vector and corresponding vertex indices from A.
9. Rebuild the isosurface data file that describes the extracted vertices and edges [FIG. 3D].

Newell's method [Tamp 92] is used to find the best-fit plane normal in step 2 of Table 2.1. It calculates the plane equation coefficients of the collinear vertices projected as a polygon onto the XY, YZ, and ZX Cartesian planes. The area of these projected images is proportional to the coefficients of the normal vector of the polygon [FvFH 90]. When the vertices form non-planar polygons, the coefficients of the best-fitting plane are calculated. For step 8 of Table 2. 1, bit vectors with size of the total vertex number are used. For each vector, 0 is given when the vertex is within the 3D ROI, otherwise 1 is assigned. By adding bit vectors that correspond to the index of vertices in the triangle list, it can be determined whether each triangle in the list is composed of vertices that are entirely inside the 3D ROI. Specifically, if the result of addition is not 0, then the triangle is eliminated from the list. Note that because the 3D ROI isosurface image is reconstructed based on indices of the vertex set, reorientation of the resulting surface is unnecessary.

Figure 3:
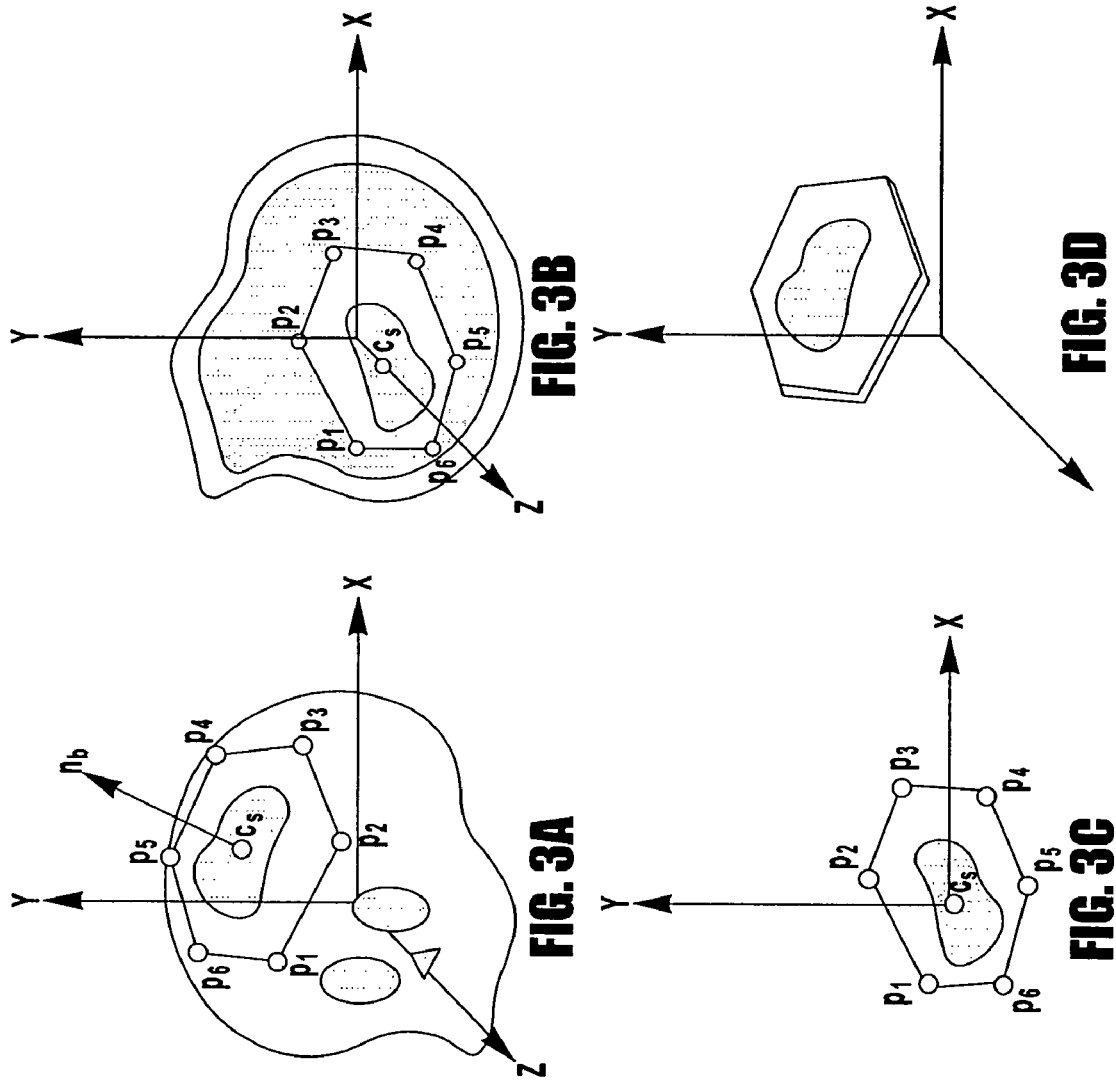
FIGS. 3A-3D shows a cross-sectional view of a 3D ROI Clipping Process in accordance with the present invention.

FIG. 3 which incorporates FIGS. 3A-3D shows the 3D ROI clipping process. FIG. 3A shows the complete skull polygonal mesh isosurface where $n_b$ is the normal vector of the best-fitting plane of selected contour, and $c_s$ is the centroid of the contour defined by operator-seeded points pi FIG. 3B shows after $n_b$ is aligned with the Z-axis, points that have negative Z values are eliminated. FIG. 3C shows a series of linear inequality tests are performed to extract data that resides outside of the contour. FIG. 3D shows reconstructed data representing a 3D ROI. Note that the 3D ROI is no longer a closed surface.

The algorithm's running time bound is O(n+n·m)=O(n·m), where n is the total number of vertices and m is the number of edges of the clipping contour. In practice, because n>>m, the total running time can be approximated as O(n). Note that instead of using plane equations to determine the 3D ROI, a series of line equations in a 2D plane are used, simplifying the process. Running time for Newell's method is trivial since it is a O(k) algorithm, where k is the number of operator placed landmarks, always much smaller than n.

Cube Cut

Occasionally, the 3D-ROI contains complexly shaped regions that may be separated from the cranial defect surface of interest. Indeed, many of these contiguous regions are sufficiently complex in shape to act as outliers in the surface curvature analysis. Therefore, a cube-shaped 'eraser' is employed to remove these regions. Currently, rotation of the cube eraser is not supported, however it is an interactively resizable and translatable object. Once the cube-cutting operation is invoked, 3D-ROI vertices within the cube's x, y, and z dimensions are eliminated. Following the cube-cutting operation, a triangular mesh isosurface is reconstructed using the same method applied to the 3D ROI surface reconstruction.

Operational Curvature Analysis

Operational curvature calculation sets a basis for curvature analysis. It is an approximation of the curvature definition known from differential geometry.

Operational Curvature Definition

Among the various definitions of curvature, the definition of a curvature vector and its magnitude can be determined from the derivative of a unit tangent vector as follows [Case 96]:

Equation 2.1: Curvature Vector and Curvature.

Curvature vector:

$$K_c n = \frac{dt}{dl} = \lim_{\Delta l \to 0} \frac{t(l + \Delta l) - t(l)}{\Delta l}$$

Curvature:

$$K_c = \lim_{\Delta l \to 0} \left| \frac{t(l + \Delta l) - t(l)}{\Delta l} \right|$$

where, n is a unit vector perpendicular to the tangent of the curve at point p, and Δl refers to an arc length between the starting and ending points that is defined for a parametric space curve along the specified interval. The function t(l) comprises a unit tangent vector at p. Because our domain of the computation is a discrete space, this algebraic curvature definition cannot be directly applied. However, if we assume that all vertices of our space curves or surfaces are sub-sampled with sufficient resolution, then the discretely approximated results can closely resemble that of a continuous domain. In this case, let $p_i$ be a point in 3D space, and $t_{ij}$ be the unit vector that is defined if an edge exists between the two points $p_i$ and $p_j$. Then, $t_{ij}$ can be considered as a unit tangent vector between points $p_i$ and $p_j$. The modified definition of curvature in Equation 2.2 using these measures is what we refer to as the operational curvature.

Equation 2.2: Operational Curvature.

Operational curvature:

$$K_d = \frac{|t_{bc} - t_{ab}|}{|p_c - p_b| + |p_b - p_a|}$$

Note that it is assumed that each vertex is a sampled point of the cranial defect margin space curve, which is sampled at the highest sampling rate. Thus, it can also be assumed that the terms corresponding to arc length will asymptotically reach zero. However, this small arc length is left in the definition as the sum of distance along two consecutive line segments. Unlike the curvature value of a point on a space curve, the notion of principal curvature and principal direction must to be introduced to characterize the curvature on a polygonal mesh isosurface, thereby facilitating the location of crestlines.

Principal Operational Curvature Mapping of a Point on Surface

Figure 4:
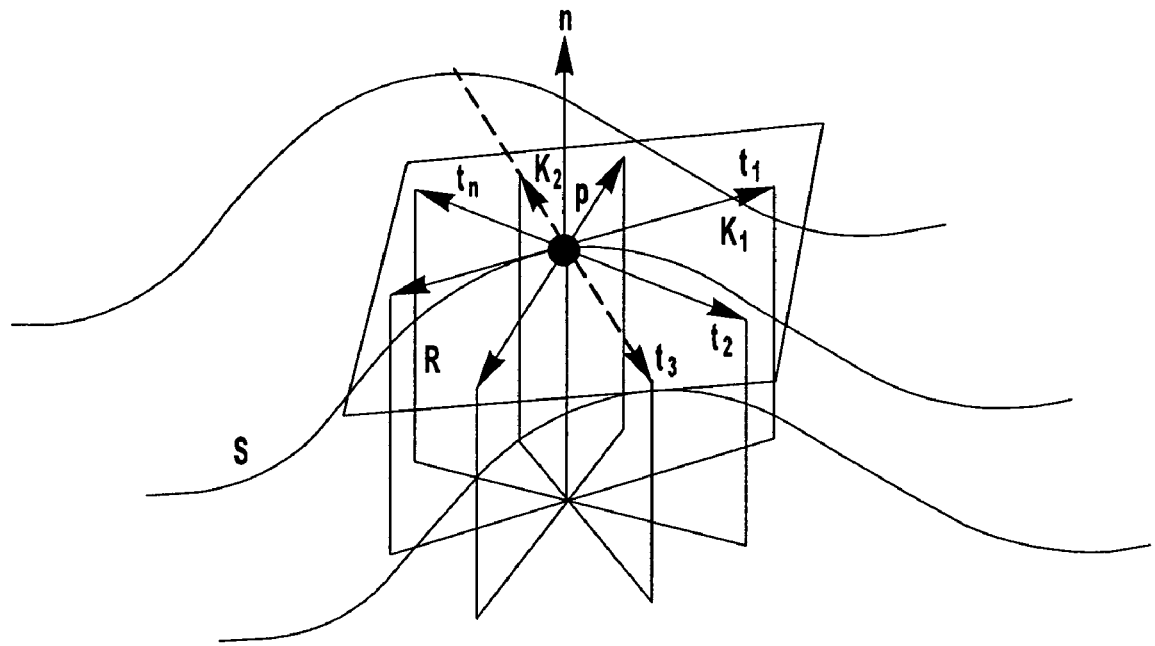
FIG. 4 is a curvatures at an arbitrary point on a surface in accordance with the present invention.

FIG. 4 shows an arbitrary point, p, on surface S where it may have an infinite number of curvature values depending on direction. The curvatures of FIG. 4 are at an arbitrary point on a surface. $K_1$ is the maximal curvature at point p on surface S, possessing the highest curvature value along principal direction $t_l$.

We may analyze this situation as if an infinite set of curves are passing through p, however the tangents, $t_n$, of those curves must cross a point p in a common plane, called tangent plane R. The normal vector of R at p is the normal vector n to surface S at p as well. The normal section is a space curve that can be defined from the intersection of surface S and a plane that contains n. Consequently, all normal sections of p can be located by continuously rotating a plane that contains n as its central shaft, so these space curves pass through R at p.

For each direction $t_n$, with normal n, there can be only one corresponding curvature $k_n$. However, there exists two curvatures, $K_1$ and $K_2$, in different directions $t_1$ and $t_2$ at point p, which correspond to the maximum and the minimum absolute values, respectively. These directions are referred to as the principal directions, and the curvatures at these locations as the principal curvatures. Among the two principal curvatures, $K_1$ is referred to as the maximal principal curvature. By measuring $K_1$ and $K_2$ and their directions, one may derive other curvature values such as Gaussian curvature and average curvature [Case 96, Hilb 90]. The main reason for using principal curvature for his analysis is that crestlines, such as the one depicted as a thick dashed line in FIG. 4, correspond to loci on the surface where principal curvature is locally maximal [ThGo 93, Thir 95]. This is where one can expect to find the cranial defect margin in 3D ROI triangular mesh. In practice, the magnitude of the principal curvature in this crestline may weaken in isolated loci as one travels along the cranial defect margin.

Figure 5:
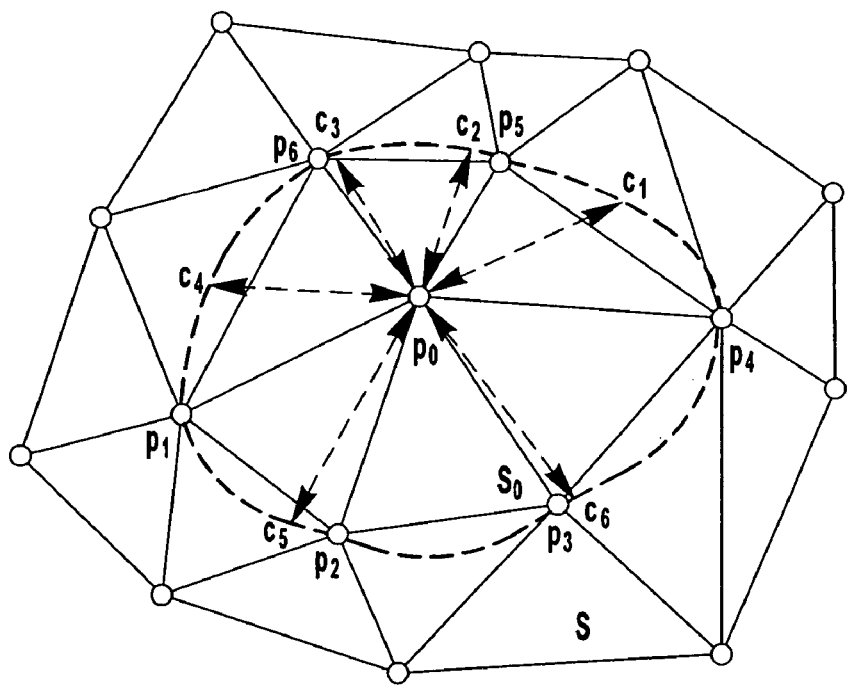
FIG. 5 shows an estimation of Principal Operational Curvature on the Point $p_0$ in accordance with the present invention.

In order to estimate the principal curvature value at each point of the polygonal mesh isosurface, we introduce a new method. We utilize operational curvature to determine a measure that is analogous to principal curvature, which we refer to as principal operational curvature. Consider a small portion of a triangular mesh isosurface, $S_0 \in S$, which is composed of one point, $p_0$, and its adjacent points, $p_n$. Spline interpolation can be performed to smoothly interpolate intervals between the points adjacent to point $p_0$. Then, a projection along the normal vector direction of $p_0$ can be performed on a 2D plane as depicted in FIG. 5. FIG. 5 shows the estimation of principal operational Curvature on the Point $p_0$: Points $p_i$ are vertices of the polygonal mesh isosurface, S. A spline interpolating points along $c_i$ between adjacent $p_i$ is sequentially paired by calculating dot products to find the opposite facing vectors, where $p_0$ is set to their origin. The strait lines $p_ic_i$ are seen as 2D projections of the normal sections.

A Catmull-Rom spline curve interpolation [CaRo 74] is used since it guarantees that each piecewise spline curve passes sequentially through the given control points. Note that points adjacent to $p_0$ are used as control points for this spline curve. The principal operational curvature value at a given point on an isosurface image can be calculated as:

Equation 2.3 Definition of Principal Operational Curvature.

Principal operational curvature value at $p_0$:

$$K_1 = \text{Max}\left[\frac{v_j - u_i}{|p_i - p_0| + |p_0 - c_j|}\right]_{v_j u_i = -1}$$

where $u_i$ denotes the unit vector of direction $p_ip_0$, cm denotes interpolated points, and $v_j$ denotes the unit vector of direction $p_0c_j$. Vector $v_i$ and $u_i$ are chosen to insure that the dot product of the two becomes approximately −1, thereby selecting two vectors that are facing in opposite directions. The concatenation of three points forms a straight line on the projection plane, which can be regarded as a projection of a normal section. By mapping principal operational curvature at all points in the isosurface image, we construct a global curvature map.

When an adaptive isosurface building algorithm, such as the Wrapper [GuDe 94, GeHu 95] is used, small triangles are patched into areas with high complexity (i.e., high curvature). Since operational curvature values are inversely proportional to the length of the edges of these triangles, a relatively higher estimate of curvature will be obtained in those regions. This property consequently amplifies the magnitude of the higher curvatures found in Wrapper-produced surfaces.

Identifying the Cranial Defect Marginre-processing of Cranial Data The identification of the cranial defect margin is initiated by an operator clipping a 3D ROI. The resulting 3D ROI should include at least 1.0 cm of surface space adjacent to the cranial defect margin. Once the operator has performed an operational curvature analysis on the 3D ROI, the determination of curvature cost factors and a color mapping of the magnitude of the principal operational curvature at each surface point is done.

Histogram Equalization

The distribution of the intensity values in an image is often referred to as a histogram. Histogram equalization [GoWo 92, SoHB 99] is an automatic contrast enhancement technique commonly used for 2D intensity images. The aim of Histogram equalization is to resample a biased intensity distribution over the entire intensity scale in order to improve visual contrast; in this case it is the contrast of curvature values at the defect crestline margin.

Suppose an input histogram, H(p), has input intensity ranges $[p_0, p_k]$. The objective is to find a monotonic pixel intensity transformation, q=T(p), such that the desired output histogram, G(q), is uniform over the output intensity range $[q_0, q_k]$. When the histogram is modeled as a discrete probability density function, the monotonic property of the transform T implies:

$$\sum_{i=0}^{k} G(q_i) = \sum_{i=0}^{k} H(p_i) \qquad \text{Equation 2.4}$$

The sums in this equation can be interpreted as discrete distribution functions. By assuming that the input image has N rows and columns, the equalized histogram would correspond to the uniform probability density function:

$$f = \frac{N^2}{q_k - q_0}.$$

When restated as a continuous probability density, above equation may be expressed as:

$$N^2 \int_{q_0}^{q} \frac{1}{q_k - q_0} ds = \frac{N^2(q - q_0)}{q_k - q_0} = \int_{p_0}^{p} H(s) ds \qquad \text{Equation 2.5}$$

The transformation T, is therefore derived as follows:

$$q = T(p) = \frac{q_k - q_0}{N^2} \int_{p_0}^{p} H(s) ds + q_0 \qquad \text{Equation 2.6}$$

The cumulative histogram, which refers to the integral part of the equation, can be expressed in the discrete domain as:

$$q = T(p) = \frac{q_k - q_0}{N^2} \sum_{i=p_0}^{p} H(i) + q_0 \qquad \text{Equation 2.7}$$

Actual implementation of this histogram equalization algorithm for a n by m pixel-sized image is presented in Table 2.2 [SoHB 99].

TABLE 2.2

Histogram Equalization Algorithm:

1. Create a histogram array H[t] of n × m image, where t is the total number of distinct intensity values.
2. Build a histogram by scanning every pixel and then incrementing its intensity $i_k$ corresponding to index of H by one (i.e., $H[i_k] = H[i_k] + 1$, where k = 1, 2, 3, . . . , t − 1).
3. Construct the cumulative image histogram array $H_c$, where $H_c[0] = H[0]$ and $H_c[k] = H_c[k − 1] + H[k]$.
4. Define transfer function $T[k] = \text{round}\left(\frac{t-1}{nm} H_c[k]\right)$.
5. Rescan the image and replace each pixel's intensity with $i_k = T[i_k]$.

The image size is applied to the total number of vertices that compose the cranial isosurface. The principal operational curvature are normalized from 0.0 to 1.0, and then quantized from levels 0 to 1023. These levels represent the intensity of a 10 bit curvature map that will be equalized. FIG. 6 which includes FIG. 6A and 6B shows operational curvature histogram equalization. FIG. 6A shows the original operational curvature map histogram. FIG. 6B shows the equalized histogram of the same operational curvature map.

The original histogram usually shows a left-bias towards low curvature values [see FIG. 6A], whereas the equalized histogram shows more widely distributed curvature values [FIG. 6B]. Because the curvature measure is normalized, the left-biased histogram implies that very few extremely high curvature regions exist on cranial isosurface images. Due to their rarity, the extremely high curvature regions are usually irrelevant to detection of the cranial defect margin crest-line. However as outliers, they strongly influence the curvature color-coding scheme. In order to avoid changing the measured principal curvature during the cranial defect margin crestline identification process, the histogram equalized-curvature map is only applied to the visualization. The visually highlighted crestlines guide the operator to accurately position crestline seed landmarks.

Detection of the Cranial Defect Margin Crestline

Because polygonal mesh isosurface images are composed of vertices and edges, they can also be represented as graphs. This facilitates modeling the cranial defect margin crestline detection as finding a consecutive minimum traversal cost path. Based on the color map of principal operational curvature, an operator starts the cranial defect margin detection by placing several seed landmark points along the crestline at locations that present high principal curvature. These operator-specified "seed" landmarks can be compared to signposts that will guide the crestline detection process to pass from one to the next. When the entire 3D ROI is represented as a graph, the area between a pair of adjacent seed landmarks is treated as a sub-graph, which is referred to as a sector. FIG. 7 shows a sector, $S_1$, bounded by two operator picked landmark points, $p_1$, $p_2$, and a centroid point, $p_c$, of the 3D ROI to define a sector. As seen in FIG. 7, the sectors are pie-shaped portions of the 3D ROI. Consequently, each sector is treated as an independent sub-graph during the crestline search. In terms of the implementation, adjacency lists are built to represent each sector as a graph by referencing topological information in the region of the 3D ROI.

The process of dividing the 3D ROI into sectors is similar to that of 3D ROI Clipping. First, the best fitting plane normal, n, for the operator-selected seed landmarks is determined. Next, the 3D ROI and seed landmarks are reoriented so that the direction of n is aligned with the Z-axis. Both the 3D ROI and seed landmarks are projected onto the XY-plane, while indices of each projected seed landmark are sorted in an order based on the angles between each projected landmark and the positive X-axis. This sorting allows freedom of the operators to pick the seed landmarks in any sequence and direction (i.e., clockwise or counter-clockwise along the crestline). A line is then defined between the seed landmark point and the centroid point of the 3D ROI on the projected plane, and finally, clipping surface outside a pair of adjacent lines defines the sectors. The sector contains even less data than the 3D ROI, thereby further reducing the computational expense for the minimum cost path search. Extracted vertices composing each sector are first rebuilt into a polygonal mesh using an identical method for constructing the 3D ROI. Each sector is then represented as a sub-graph with an adjacency list data structure.

The cranial defect margin is detected by running a single source shortest path finding algorithm, such as Dijkstra's Algorithm [COLR 90], in each sector to determine the minimum traversing cost path. A summary of the cranial defect margin crestline identification algorithm is presented in Table 2.3.

TABLE 2.3

Cranial defect margin Crestline Detection Algorithm:

1. Find the normal $n_b$ of the best fitting plane for operator-selected landmark points on 3D ROI.
2. Reorient the 3D ROI and seed landmark points so that $n_b$ and the Z-axis are aligned in parallel.
3. Set the centroid of the contour formed by the landmark points as the origin of the XY-plane
4. Project the points composing the 3D ROI and seed landmarks onto the XY-plane.
5. Sort the projected landmarks according to the magnitude of the angle between the landmarks and the positive X-axis.
6. Extract sub-graphs that are within the angle between the two adjacent landmarks.
7. Run a single source minimum cost path finding algorithm on each sector, where one sector's landmark point is set to a source vertex, and the adjacent landmark point becomes the terminating vertex.
8. Connect the detected path into a cycle and sequentially store the vertex positions as the cranial defect margin crestline.

The data structure of the minimum cost path specified is a linear array storing a sequence of vertex indices included in the 3D ROI. Then, the 3D positions of the points in the VNX data format used are de-referenced to define the series of points that the cranial defect margin traverses.

Thickness Measurement of Bone Structure underneath the Cranial Defect Margin Crestline Once the cranial defect margin crestline has been identified in each sector, the thickness of the bone structure found internal to the crestline is measured. If the bone layer detected under the candidate cranial defect margin crestline point is very thin or has zero-thickness, placing an implant there may lead to poor fixation, even mechanical failure which is referred to as push-in failure. Push-in failure would lead the implant to fall into the cranial cavity and possibly damage the brain.

The cranial isosurface data derived from the Wrapper algorithm are always closed surfaces [GuDe 94], with an internal and an external surface. Usually, the surface of the defect site is near where those two surfaces meet each other, as depicted in FIG. 7. To avoid bone with zero-thickness underneath the cranial defect margin, the cranial defect margin path is forced to traverse the adjacent external surface based on a thickness measurement. In order to measure the thickness, a ray is cast from each cranial defect margin point internally in the normal direction of the best-fitting plane of operator-specified seed landmarks. Then the Euclidean distance is calculated between the ray origin point and the ray-surface collisions. For the ray-surface collision detection process using ray-cast, and its graphical feedback, the SGI Open Inventor built-in class library [Wern 94] is used.

However, to avoid points with low thickness along the cranial defect margin path, the thickness measurement is done in a sector-wise manner. If the thickness at any point along the minimum cost path is determined to be less than the, given threshold thickness, an infinite cost is imposed on the vertex. This causes the shortest path finding algorithm to iteratively attempt to find a new path until all points of the path have more than the predefined minimum thickness under the cranial defect margin crestline.

Cranial Defect Margin Identification Cost Function

In addition to iterative movements away from points with insufficient underlying bone thickness, four factors contribute to the graph-traversing cost. First, the principal operational curvature of each vertex is taken into account. Second, the linearity of the potential path, based on the distance between the two adjacent operator-selected seed landmarks, is measured. Third, the distance between each potential crestline point and an orthogonal plane below the 3D ROI is used. Finally, the density of the vertices is considered. The first three factors are defined for each vertex, and the last factor is considered for each edge. Equation 2.4 defines of the cost functions that evaluate vertex cost $c_{v_i}$, and edge cost $c_{e_{ij}}$, respectively:

$$c_{v_i} = \alpha(1.0 - k_i) + \beta \cdot t_i + \gamma \cdot d_{im}$$

$$c_{e_{ij}} = \delta \cdot d_{ij}(c_{v_i} + c_{v_j}) \quad \text{Equation 2.8: Vertex and Edge Cost Functions}$$

where, $k_i$ is the normalized principal operational curvature value at vertex $v_i$, $t_i$ is the normalized Euclidean distance between vertex $v_i$ and a line segment defined between the starting landmark and the terminating landmark. The Euclidean distance $d_{im}$ is a height between each point, and a cranial defect margin best-fitting plane shifted beneath the 3D ROI. The Euclidean distance between vertex $v_i$ and $v_j$ is $d_{ij}$, and coefficients $\alpha$, $\beta$, $\gamma$ and $\delta$ are positive weight factors.

The cost for adding a new vertex to the minimum cost path is determined from three factors. The first factor is a curvature cost that derives from the operational principal curvature map. The second factor is a linear track cost that is proportional to the Euclidean distance between a candidate vertex and a line segment defined by the two adjacent seed landmarks spanning the sector. This second factor constrains the cranial defect margin path from straying too far away from the linear path between the operator-chosen landmark points. Without this constraint, the resulting path can be jaggy due to local noise in the curvature cost. The third factor is a height cost that relatively weights the crestline path to prevent it from falling into the cranial defect margin. Because a higher cost is imposed on points closer to an internally shifted plane that best-fits the operator-specified seed landmarks, the height cost increases as the search moves internal to the cranial defect.

In order to use a single-source minimum cost path search algorithm, edge costs for the graph traversal must be defined. The edge costs are derived from the previously estimated vertex costs. Because uniform vertex density along the cranial defect margin is not guaranteed, a higher cost is imposed on long edges than the short ones. When $d_{ij}$ is set as a constant, the growing cranial defect margin avoids regions with high vertex density due to the high cumulative traversal cost in the sector. Therefore, this factor tends to normalize the vertex density of the isosurface in 3D space, which is referred to as density cost.

Cranial Defect Margin Space Curve Smoothing

Clinical CT-scans typically have slice thickness of 1 to 3 mm, which corresponds to the Z dimension of the volume image. It is also common to find pixel sizes of 0.3 to 0.7 mm in the X and Y dimensions, which will result in anisotropic voxels [Robb 95]. This anisotropy, especially due to the difference with the slice thickness resolution, causes jagged staircase shapes on the reconstructed isosurface image that are referred to as CT artifact (stair effect cause rough fit) or slice-edge artifact. As a cranial defect margin is identified on the patient's cranial isosurface, it inherits these slice-edge artifacts as well. The slice edge artifacts are usually apparent at the top of an axially scanned patient's cranium, a portion of the skull where a prosthetic plate is very likely to be needed. By removing the slice edge artifacts, which function as pure noise, the chance of producing a well-fitting implant is increased. To do so, the detected cranial defect margin space curve is encoded as a series of smooth space curves that are seamlessly connected using the Catmull-Rom spline interpolation technique [CaRo 74]. The Catmull-Rom spline is a piecewise interpolating spline that shares many properties with the B-spline, such as affine (grows in only 1 direction) invariance, global smoothness, and local control [BaGo 88]. Note that this spline interpolation was also used for determining principal operational curvature.

Characterizing Cranial Defect Margin Crestline Geometric Properties

Figure 8:
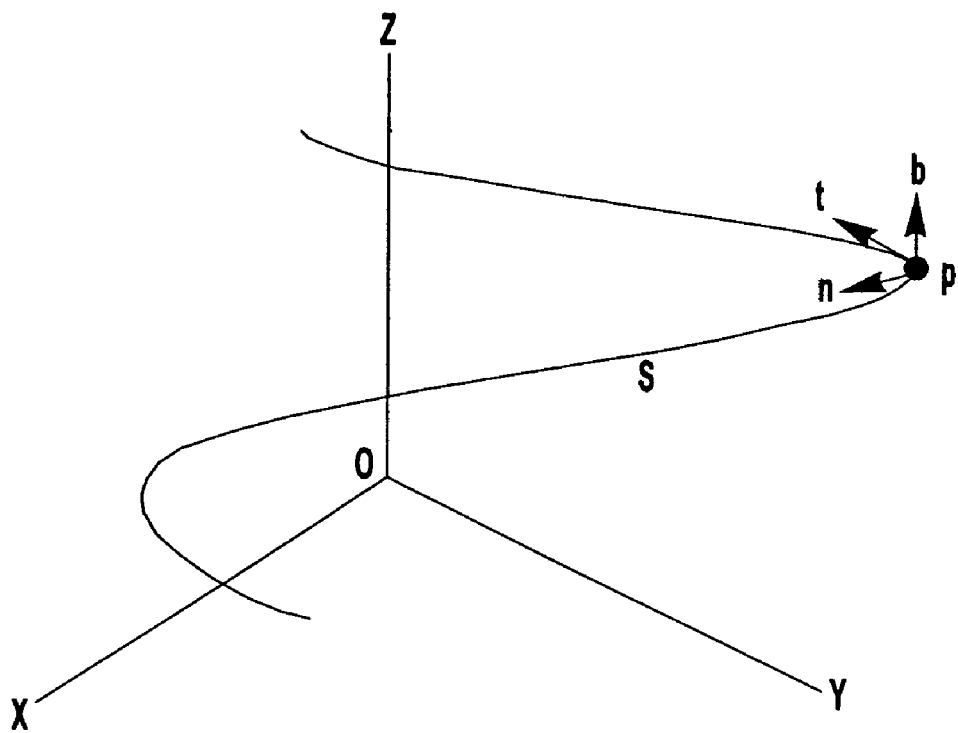
FIG. 8 shows a space curve and its Serret-Frenet Triad in accordance with the present invention.

The extracted cranial defect margin crestline is archived as a Catmull-Rom spline. This space curve was smoothed to remove slice-edge artifacts inherited from the relatively large 3D CT inter-slice spacing. However, the cranial defect margin may still present sharp extensions, incurvations, or twists that present high torsion. Substantial incurvations along the line, whether twisting in or out of plane (i.e., torsion), are likely to promote crack formation under repetitive or traumatic stress. In addition, narrow excurvations (e.g., 'fingers' at the implant margin) are likely to snap off, especially in response to trauma. Characterizing the curvature and torsion of the cranial defect margin provides important information that is otherwise unavailable to one who is preparing a cranial implant via manual methods. The operator can choose to remove sharp incurvations or excurvations along the cranial defect margin space curve as a consequence of this characterization. FIG. 8 and Equation 2.11 show how curvature and torsion can be geometrically defined on a space curve. FIG. 8 shows a space curve and its Serret-Frenet triad. At each point of the arc, a unit tangent vector t and a principal unit normal vector n can be defined. The plane including t and n is referred to as the osculating plane. Unit normal vector b of the osculating plane is referred to as the unit binormal vector. The unit vectors t, n, b, the Serret-Frenet triad, are perpendicular to each other.

Based on three triads of unit vectors, we can define curvature K and torsion T via the Serret-Frenet formula [Case 96] for space curves as:

Equation 2.15 Serret-Frenet formula $$\frac{dt}{ds} = Kn$$

$$\frac{dn}{ds} = -Kt + Tb$$

$$\frac{db}{ds} = -Tn$$

Curvature Calculation along the Cranial Defect Margin Crestline

The data representation of the cranial defect margin crestline is a sequence of points in 3D space. Thus, the definitions in Equation 2.15 must be modified for this application. Suppose $p_i$ is a point in the space curve segment, then $$t_i = \frac{p_{i-1}p_i - p_ip_{i+1}}{|p_{i-1}p_i - p_ip_{i+1}|}$$

will be the approximated unit tangent vector of $p_i$ as depicted in FIG. 2.9. Because Equation 2.15 shows that the curvature at $p_i$ can be calculated by differentiating the normal tangent vector, the curvature at point $p_i$ can be approximated as:

$$K = |t_{i+1} - t_i| \qquad \text{Equation 2.16}$$

Note that the above definition is similar to that of operational curvature in Equation 2.2, where $|p_c - p_b| + |p_b - p_a| = 1$. Because the spline interpolation increases, the point density in the cranial defect margin crestline, mapping operational curvature (see Section 2.2.3) is likely to result in higher operational curvature value. Although this property is useful for principal curvature estimation on an adaptive triangulated surface, it is inappropriate for comparing average curvature values between the original and smoothed cranial defect margin crestlines.

Figure 9:
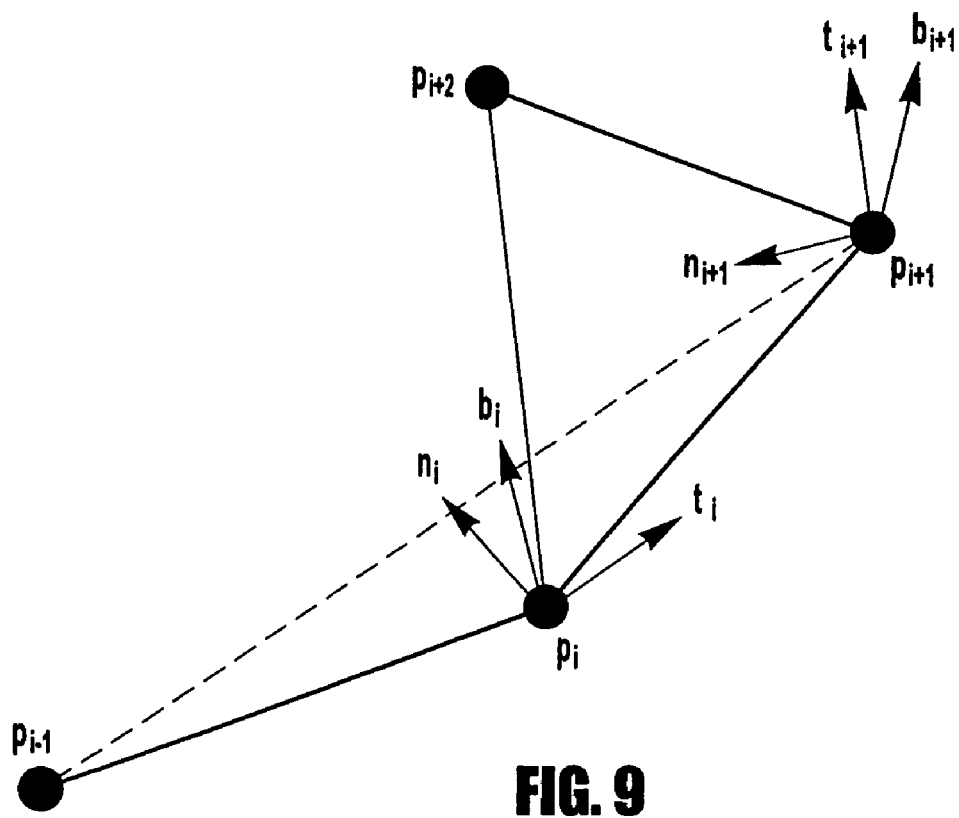
FIG. 9 Serret-Frenet Triads at space curve of linear links of points in 3D Space in accordance with the present invention.

FIG. 9 shows the Serret-Frenet triads at space curve of linear links of points in 3D space. The thick line segments compose a space curve in 3D space, while the dashed lines, together with a pair of thick line segments define the osculating planes. Point $p_i$ is an end point of line segments, and ti denotes a tangent vector of the $p_i$. With three points, the normal vector, $b_i$, of an osculating plane is defined.

Torsion Calculation along the Cranial Defect Margin Crestline

As with the curvature calculation, the definition of torsion in Equation 2.15 is essentially a differentiation of the binormal vector $b_i$. To acquire $b_i$, we locate the normal vector of the osculating plane of $p_i$ with three consecutive points in the space curve by taking the cross product of $p_ip_{i+1}$ and $p_{i-1}p_i$. Therefore, the equation for estimation of approximated torsion T along the cranial defect margin space curve at point $p_i$ is:

$$T = |b_{i+1} - b_i|, \text{ where}$$

$$b_i = p_ip_{i+1} \times p_{i-1}p_i \qquad \text{Equation 2.17}$$

Bone Thickness Measurement

Figure 10:
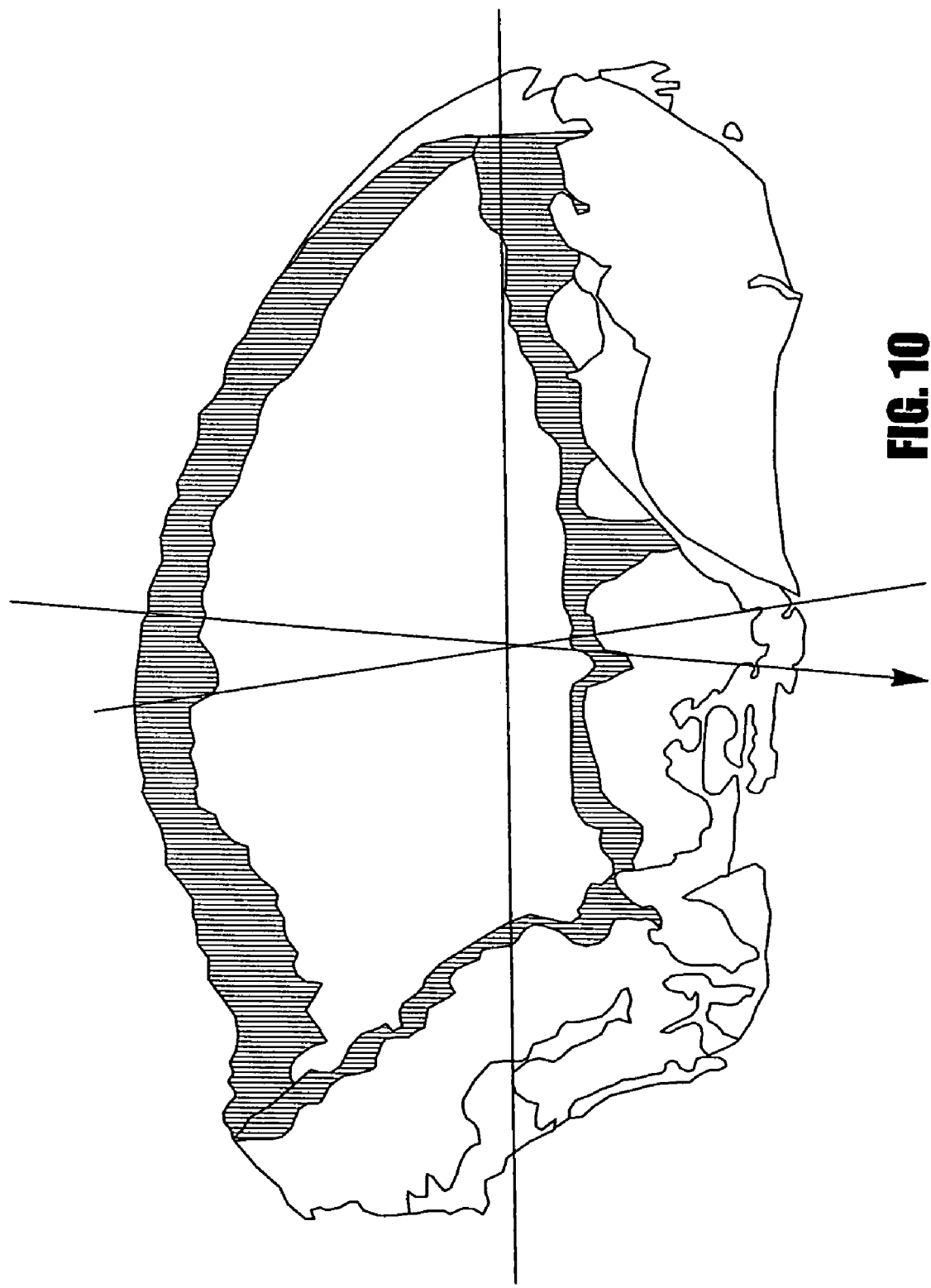
FIG. 10 shows thickness measurements in accordance with the present invention.

FIG. 10 visually shows the thickness measurement taken along the cranial defect margin crestline of a patient. The 3D ROI is rendered transparently to show the rays passing internally from the cranial defect margin crestline found on the external surface. The rays are cast in a direction normal to the best-fitting plane of the cranial defect margin crestline. Note that if the cranial defect margin fell into the defect during the crestline search, it is highly likely to result in zero-thickness, which would re-invoke the search in that sector.

In FIG. 10, the space curve represents the identified cranial defect margin crestline in the defect site. The rays measure the thickness of the bone underneath the detected cranial defect margin crestline.

Cranial Implant Surface Interpolation

Up until now, a method is described to accurately identify a crestline along a cranial defect margin. The cranium had been processed and visualized as a polygonal mesh isosurface image, which had been extracted from a patient's 3D CT-scan. The cranial defect margin crestline describes the outer edge of the cranial defect, where the implant will be seated. The next step in the CAD approach of the present invention is to design the implant surface that will fill the defect space within the cranial defect margin crestline.

The approach of the present invention to this problem is to deform an appropriately matched skull template surface onto the patient's skull isosurface image. The skull template surfaces are either a left-right mirrored or an average skull triangular mesh isosurface image. To acquire a mirrored template surface, the X and Y coordinates of the points composing a cranial isosurface are swapped after setting the centroid of the skull image as the origin. The average skull template image being used is derived from work by Dean et al. [DBKL 98, CBDK 93], using Winged Edge surface encoding [FvFH 90]. In order to deform either of these skull template surfaces, the TPS warp algorithm [Book 89] is employed, which preserves $C^1$ continuity in the resulting surface [CaFB 97]. The TPS warp can be extended to 3D, and has been used for calculating B-spline encoded average skull shapes [SuDe 01]. While the TPS warp is translation, rotation, and scaling invariant [Book 89], the average skull template must be adjusted to fit the patient's reference frame to initiate a useful filling of the defect site. For this reason, the Procrustes superimposition method [Rohl 89] is used to initially position and scale the average skull template from its initially normalized coordinate system.

Methods

Template Surface Determination

The cranial prosthetic implant surface interpolation is initiated by choosing an appropriate skull template. As previously noted, either a left-right mirror of the patient's cranium (case 1 below) or an average cranial template surface (case 2 below) is chosen depending on the location and the distribution of the cranial defect.

Case 1: Unilateral Cranial Defect

In a case where the defect is located unilaterally, the left-right mirror image of the patient's original skull isosurface image is left to become the skull template surface. For appropriate left-right mirroring, the patient needs to lie in a supine (i.e., on their back) position during the CT scanning process. This pose allows for all axial slices to be close to perpendicular of the patient's right-left plane. This will avoid top-to-bottom or front-to-back mirroring. Following appropriate left-right mirroring, geometric translation of the centroid of the left-right mirrored skull template to the original cranial isosurface centroid results in a rough match since the scaling factors are identical.

The displacement is due to the patient not lying in a fully supine position, tilting of other axes that are parallel to the patient's head, and non-ideal symmetry of the human cranium. These parameters are rarely adjusted during the CT-scanning phase, causing the two images to show insufficient registration. However, the interactively selected skull landmarks (e.g., suture intersections, muscle scars, and boney protuberances) are used to globally co-register the skull template surface with the original patient's cranial isosurface image via global first pass TPS warp.

Dean et al. [DeMB 02] present more than 50 cranial landmarks with unique locations and anatomical labels. These landmarks are globally distributed and are located based on knowledge of biological homology. The data structure representing each landmark has four tuples storing its anatomical label, X, Y, and Z position in 3D space. A list of landmark set excluding the anatomical label tuple will be referred to as a landmark configuration and its matrix representation as a landmark configuration matrix.

Case 2: Defect Spanning the Center of the Cranium

Cranial defects spanning both sides of the skull leave too little anatomy to provide sufficient biological homology in a left-right mirrored image. In these cases, an average skull template surface is used. Unlike a mirrored template surface, the average skull image must be scaled to an appropriate size and reoriented for the patient's reference frame. For this reason, the Procrustes superimposition method is used to match the skull template so that the two differently sized cranial images can be initially aligned. Because the Procrustes superimposition method also requires two sets of biologically homologous landmark configurations, an operator must manually prepare them as well. As with the case for a left-right mirrored template, the resized average template surface is then deformed via TPS warp to provide a useful registration.

Skull Template Registration Tools

In order to deform the cranial template surface to the patient's skull surface, two surface registration techniques are used. One is the Procrustes superimposition method [Rohl 89], which is based on a non-affine transformation (i.e., preserving parallelism of lines after transformation). The other is the TPS warp [Book 89], which performs both affine and non-affine transformation. In the approach of the present invention, the fitting and deformation of a skull template surface is preferably driven by two landmark configuration sets manually specified by an operator. In 3D space, a landmark point set $C_S=\{p_i(x_i, y_i, z_i)|i=1, 2, \ldots, n\}$ denotes the configuration of the source landmark points and the other landmark point set $C_T=\{q_j(x_j, y_j, z_j)|j=1, 2, \ldots, n\}$ denotes configuration of the target landmark points. An interactive landmark picking process allows the operator to directly select the homologous points on the source and target surfaces, where the former is the skull template, and the latter is patient's cranial isosurface. This interactive landmark identification tool is implemented using the Open Inventor class library [Wern 94].

Procrustes Superimposition

The Procrustes superimposition method has been used in many studies where anatomical landmark registration is used to indicate the degree of morphological similarity. This algorithm performs rigid body transformation (i.e. translation, rotation) as well as uniform scaling on one landmark configuration in order to superimpose it onto the other configuration. The Procrustes method minimizes the distance between the two landmark configurations, where the sum of inter-landmark distance is the minimum sum of squared distances between all corresponding landmarks. This can be calculated via matrix operations as follows [Subr 00]:

The Procrustes superimposition method is applied between the source landmark configurations $C_S$, and the target landmark configurations $C_T$ [See FIG. 11]. FIG. 11 shows the Procrustes Superimposition Method. The inter-landmark distances between the two landmark configurations $C_D$ (black points) and $C_S$ (white points) are minimized sequentially by translation, scaling, and rotation transformations.

Each configuration is expressed as a n×k matrix where n denotes the number of landmarks and k denotes the dimension of each coordinate. The source and target configurations shown in FIG. 11 would be a 4×2 matrix, respectively.

Translation

The coordinates of landmark configurations $C_S$ and $C_T$ are translated in order to share the origin of $C_T$. This can be achieved by subtracting the means of each axis from $C_S$ and $C_D$, which is equivalent to pre-multiplying each configuration by I–N, where I is a n×n identity matrix, and N is a n×n matrix with every element equal to 1/n. Equation 3.1 presents the I–N matrix.

$$I - N = \begin{bmatrix} 1-\frac{1}{n} & -\frac{1}{n} & -\frac{1}{n} & -\frac{1}{n} \\ -\frac{1}{n} & 1-\frac{1}{n} & -\frac{1}{n} & -\frac{1}{n} \\ -\frac{1}{n} & -\frac{1}{n} & 1-\frac{1}{n} & -\frac{1}{n} \\ -\frac{1}{n} & -\frac{1}{n} & -\frac{1}{n} & 1-\frac{1}{n} \end{bmatrix} \quad \text{Equation 3.1}$$

Equation 3.2 indicates a translation that results in both matrices sharing the origin of matrix $C_1$.

$$C'_S = (I-N) \cdot C_S$$

$$C'_T = (I-N) \cdot C_T \quad \text{Equation 3.2}$$

Scaling

Next, the inter-landmark distances between the two landmark configurations are further reduced by a scaling transformation. This operation requires the calculation of scaling factors for both configurations. The scalar values, $S_S$ and $S_T$, referred to as centroid size, are calculated by taking the square root of the sum-of-squared distances for each landmark to the centroid. Equation 3.3 presents the centroid size computation for all axis components, where t denotes a transpose operator. In order to accomplish the desired scaling, the centroid size is divided into landmark configurations $C_D$ and the previously translated configuration $C_S$.

$$S_S = \sqrt{\text{trace}((I-N) \cdot C_S C_S^t (I-N))}$$

$$S_T = \sqrt{\text{trace}((I-N) \cdot C_T C_T^t (I-N))}$$

$$C''_S = \frac{1}{S_S} \cdot C'_S$$

$$C''_T = \frac{1}{S_T} \cdot C'_T$$

Equation 3.3

Rotation

The optimal rotation minimizes the root sum-of-squared distances between the corresponding landmark configurations. The rotation of C''s is done by first taking its transpose, and then by pre-multiplying with k×k matrix H (Equation 3.5). The Matrix H is obtained by $H = VSU^t$, where V and U are calculated from the singular value decomposition [Stra 98] of the product of the transpose of $C_S$ and $C_T$, and S is a matrix of diagonal elements of ±1 corresponding to the sign of matrix $\Sigma$.

$$C''' = C''^t_S \cdot H, \text{ where}$$

$$C''^{Tt} \cdot C''_S = U\Sigma V^t \quad \text{Equation 3.5}$$

The Procrustes superimposition method provides an automated means to optimally adjust the scaling factor of an average template surface before performing a TPS warp. Since both the Procrustes method and the TPS warp require a pair of homologous landmark configurations manual construction of $C_S$ and $C_D$ is a one time task.

Thin Plate Spline Warp

The thin plate spline has often been used to interpolate surfaces over scattered points [Book 89]. The physical bending energy required to merge two corresponding landmark configurations is a quadratic form of the heights assigned to the surface. As a consequence, a smooth surface deformation is acquired with the minimum bending energy via TPS warp [Book 89, CaFB 97].

Radial Basis Function Approximation

Suppose a 2D radial basis approximation function f: $R^2 \rightarrow R^2$, which maps two real variables (x, y) to (x', y') is operated on. Given a set $\{p_1, p_2, \ldots p_n\}$ of n distinct points, $p_i = (x_i, y_i) \in R^2$ referred to as the nodes of interpolation, a function f that approximates these points to $\{p'_1, p'_2, \ldots p'_n\}$, where $p'_i = (x'_i, y'_i)$, can be formulated as:

$$f(x, y) = a(x, y) + \sum_{i=1}^{n} \lambda_i \varphi(|p_i - (x, y)|), (x, y) \in R^2, \lambda_i \in R \quad \text{Equation 3.6}$$

where a(x, y) is a low degree polynomial and $\varphi$ is a fixed function mapping from $R^+$ to R. Consequently, the radial basis function, f(x, y) is a linear combination of a translated radially symmetric function $\varphi$, which is added to a low degree polynomial. Then the coefficients, $\lambda_i$ of the approximation are determined by requiring f to satisfy the following interpolation conditions:

$$f(p_i) = p'_i, \text{ for } i = 1, 2, \ldots, n \quad \text{Equation 3.7}$$

$$\sum_{i=1}^{n} \lambda_i p_i = 0$$

Thin Plate Spline Radial Basis Function

When choosing function $\varphi$, there are several alternative basis functions one might consider such as linear, Gaussian, or multi-quadratic, other than the TPS basis function [CaFB 97]. The TPS algorithm uses $\varphi = U(r) = r^2 \log r^2$, where $r = \sqrt{x^2 + y^2}$, and where u(r) is expressed as $z(x, y) = -u(r)$ in Cartesian coordinates. The function u(r) is referred to as a thin plate spline or biharmonic spline basis function. This function is a fundamental solution of the biharmonic equation $$\Delta^2 U = \left(\frac{\partial^2}{\partial x^2} + \frac{\partial^2}{\partial y^2}\right)^2 U = 0.$$

The function z(x, y) computes the configuration for minimum physical bending energy known as:

$$E(z) = \int_{R^2} \int \left(\left(\frac{\partial^2 z}{\partial x^2}\right)^2 + 2\left(\frac{\partial^2 z}{\partial x \partial y}\right)^2 + \left(\frac{\partial^2 z}{\partial y^2}\right)^2\right) dx\,dy \quad \text{Equation 3.8}$$

Thus, the TPS provides a smooth interpolation function f, resulting in a surface with $C^1$ continuity following deformation of a hypothetical infinitely thin plate.

Linear Equation for TPS

In order to determine the low degree polynomial and coefficients of the TPS approximation, we can set up a linear equation based on Equation 3.7 as:

$$\begin{bmatrix} U & P \\ P^T & O \end{bmatrix} \begin{bmatrix} L \\ A \end{bmatrix} = \begin{bmatrix} V \\ O \end{bmatrix}, \quad \text{Equation 3.9}$$

where $$U = \begin{bmatrix} 0 & u(r_{12}) & \cdots & u(r_{1n}) \\ u(r_{21}) & 0 & \cdots & u(r_{2n}) \\ \vdots & \vdots & \cdots & \vdots \\ u(r_{n1}) & u(r_{n2}) & \cdots & 0 \end{bmatrix}, n \times n;$$

where $r_{ij} = |p_i - p_j|$;

$$P = \begin{bmatrix} 1 & x_1 & y_1 \\ 1 & x_2 & y_2 \\ \vdots & \vdots & \vdots \\ 1 & x_n & y_n \end{bmatrix}, 3 \times n;$$

$L = [\lambda_1, \lambda_2, \ldots, \lambda_n]^t$, $A = [a_0, a_x, a_y]^t$, and $$V = \begin{bmatrix} x'_1 & x'_2 & \cdots & x'_n \\ y'_1 & y'_2 & \cdots & y'_n \end{bmatrix}^t = [p'_1 \ p'_2 \ \cdots \ p'_n]^t$$

Then, linear equation for calculating coefficients of f is solved as:

$$\begin{bmatrix} \lambda_1 \\ \vdots \\ \lambda_n \\ a_0 \\ a_x \\ a_y \end{bmatrix} = \begin{bmatrix} 0 & \cdots & u(r_{1n}) & 1 & x_1 & y_1 \\ \vdots & 0 & \vdots & \vdots & \vdots & \vdots \\ u(r_{n1}) & \cdots & 0 & 1 & x_n & y_n \\ 1 & \cdots & 1 & 0 & 0 & 0 \\ x_1 & \cdots & x_n & 0 & 0 & 0 \\ y_1 & \cdots & y_n & 0 & 0 & 0 \end{bmatrix}^{-1} \begin{bmatrix} p'_1 \\ \vdots \\ p'_n \\ 0 \\ 0 \\ 0 \end{bmatrix} \quad \text{Equation 3.10}$$

Thus, based on Equation 3.6, the matrix elements in Equation 3.10 define a function f(x, y) everywhere in the plane as:

$$f(x, y) = a_0 + a_x x + a_y y + \sum_{i=1}^{n} \lambda_i u(|p_i - (x, y)|) \quad \text{Equation 3.11}$$

$f_x(x, y) = x'$, and $f_y(x, y) = y'$

3D TPS Warp

The application of the TPS algorithm can be extended to 3D space, including 3D skull shape averaging [SuDe 01]. A 3D TPS warp extends the function z(x, y) to z(x, y, z), and $r = \sqrt{x^2+y^2+z^2}$ is used to evaluate u(r). In addition, a low degree polynomial is constructed as $a(x, y, z) = a_0 + a_x x + a_y y + a_z z$. This result expands the size of the matrix $$\begin{bmatrix} U & P \\ P^T & O \end{bmatrix}$$

by an additional row and column. Therefore, Equation 3.11 is modified as follows for a 3D TPS warp [Subr 00]:

$$f(x, y, z) = a_0 + a_x x + a_y y + c_z z + \sum_{i=1}^{n} \lambda_i u(|p_i - (x, y, z)|) \quad \text{Equation 3.12}$$

$f_x(x, y, z) = x'$, $f_y(x, y, z) = y'$, and $f_z(x, y, z) = z'$

Consequently, we perform a TPS warp by building matrices based on two sets of landmark configurations, $C_S$ and $C_D$. Once the warping coefficients are calculated via matrix inversion, the repositioning of all points composing the skull surface is processed with Equation 3.12.

Two Pass TPS Warp Scheme

A single-step surface warp driven by anatomical landmark points selected by the operator usually does not-provide a sufficient filling of the defect site. The displacement between the template and the patient objects is most apparent at the cranial defect margin; this is where a fully accurate fit is most necessary. The insufficient skull template match is mainly due to an insufficient density of skull landmarks in the region of the cranial defect site. Therefore, a two pass TPS warp scheme is employed to enhance the match in the cranial defect margin region. The first warp deforms the surface template based on globally distributed anatomical landmarks. Then, the second pass warp is performed with additional non-anatomical landmarks that are automatically detected in the regions local to the cranial defect.

Once the anatomical landmarks are manually specified on both skull template and patient's skull surface, only the landmarks pairs that have correspondence in both skull surfaces are used to build configuration matrices $C_S$ and $C_D$. Thus, landmarks missing due to the cranial defect are dropped out from this protocol before Procrustes fit or TPS warp. After the first pass global TPS warp, we locate homologous landmark pairs in the region of the cranial defect margin crestline. To do so, the previously identified cranial defect margin crestline is used. By casting rays from this crestline, ray-surface collision points on the skull template surface can be considered as homologous points to the ray origin points. These new point pairs drive the second pass warp that pins down or pulls up the skull template surface to the cranial defect margin crestline. Note that the cranial defect margin crestline was consequently pre-registered within the patient's cranial isosurface image.

When a left-right mirrored skull template is used, the template surface is composed of two different surface layers. One layer is the external surface and the other is the internal surface, which on external view is hidden beneath the external surface. To describe the method of automatic local homology detection between the template and the patient's skull surfaces, one can say that $S_p$ is denoted for the patient's skull surface, $S_{Te}$ for the exterior surface of the template, and $S_{Ti}$ for the interior surface of a left-right mirrored skull template. Because the left-right mirrored template surface is composed of two different layers, there will be at most two collisions of a ray cast from a point on the cranial defect margin crestline orthogonal to its best-fitting plane. Based on the possible cases (FIG. 3.5), the correspondence can be determined for each sampled point of the defect margin, $p_t$, and its homologous point, $p_s$, on the skull template surface. The new landmark configuration matrices $C_S$ and $C_T$ will add these $p_s$ and $p_t$, respectively for the second pass warp.

In FIG. 12 which includes FIGS. 12A, 12B and 12C, a cranial defect margin crestline ray source point, $p_d$, is depicted as a solid black circle, and its corresponding homologous point, $p_s$, on the skull template surface is shown as a white-filled circle. FIG. 12 shows the local point correspondence detection in the defect margin region. In FIG. 12A, ray source point, $p_s$, is located in between the external template surface, $S_{Te}$, and the internal template surface, $S_{Ti}$. In FIG. 12B, point $p_s$ is located below the skull template surface. In FIG. 12C, point ps is located on top of the skull template surface. Note that this surface detection scheme is required for only the left-right mirrored skull template surface.

Figure 13:
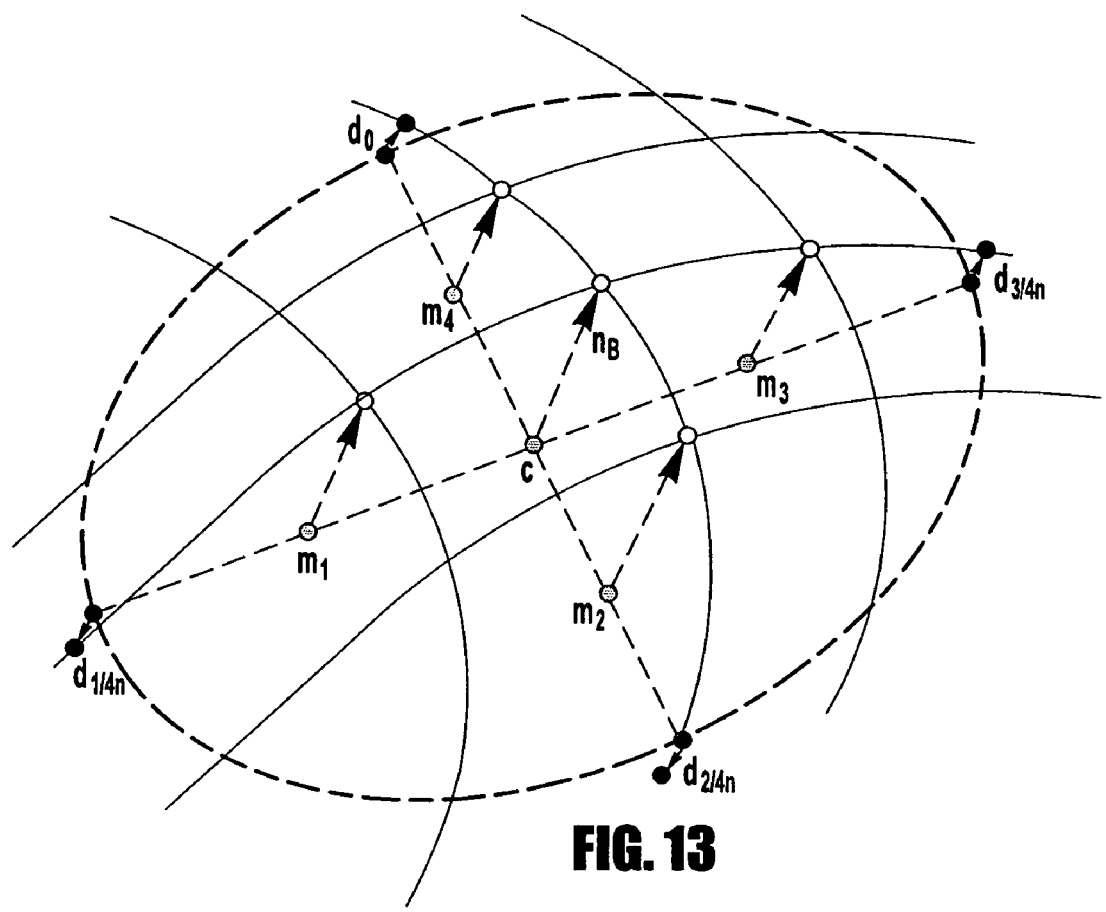
FIG. 13 shows the use of anchor warp points in accordance with the present invention.

Note that the ray source points become the target warp points, $p_t$, and the ray-surface collision points become the source warp point, $p_s$. Gray-filled circles also indicate collision points, but they must be discarded. These points belong to an interior template surface, $S_{Ti}$, which would mislead subsequent second pass TPS warp process. Because there are only three possible ray-surface collision cases, as depicted in FIG. 13, the collision points on $S_{Te}$ can be automatically detected. Specifically, when the ray was shot externally, the outer most collision point is selected. For the case of no collisions, the ray is cast internally and the first collision point is selected.

Table 3.1 summarizes the process for detecting new homologous point pairs between the cranial defect margin of left-right mirrored skull template surfaces and the patient's cranial surface for the second pass TPS warp. Unlike the mirrored template surface, the average skull templates that are used are composed of a single surface. Thus, the exterior versus interior ray-surface collision point discrimination is not required.

Two Pass Warp Algorithm

TABLE 3.1

Algorithm for Detecting Cranial Defect Margin Space Curve Warp Homolog Points on the Skull Template Surface:

1. Complete the first pass warp using the two global landmark configurations that were manually located on the patient and template skull images.
2. Subsample the previously identified defect margin space curve into a set of points, $p_d$, to have uniform spacing.
3. From each $p_d$, cast a ray externally with respect to the normal direction of the cranial defect crestline's best-fitting plane.
4. If one collision occurs, record the hit point as corresponding to point $p_s$.
5. If two collisions occur, record the second hit point as $p_s$, ignoring the first hit point.
6. If no hit occurs, cast a ray in the opposite direction (i.e., internally) from $p_d$.
7. If any hit occurs, record the first hit as corresponding to point $p_s$.
8. If no hit occurs, discard $p_d$.
9. Repeat steps from 3 to 8 until all $p_d$ cast no more than two rays (i.e., externally and internally).

Because the second pass TPS warp includes a high density of cranial defect margin crestline points, there tends to be a flattening of the resulting skull template surface internal to the defect margin crestline. This is because the TPS warp affects the entire surface, smoothly forcing a plastic deformation with minimum bending energy. Therefore, the skull template surface internal to the defect margin crestline must be included in the source and target landmark configuration matrices of the second pass TPS warp, to avoid sinking the template surface (i.e., right-left mirror or average template) into the defect. The main objective of adding anchor points is to preserve the convexity of the original skull template surface, while also insuring that it continues to fit the defect margin. These internal warp points act as local anchors that prevent adjacent surface regions from deforming during the second pass TPS warp. Therefore, these points are referred to as anchor warp points to discriminate them from the cranial defect margin warp points that actively drive the second pass warp. Unlike the other warp points, the anchor points will have identical positions in both the source and target landmark configuration matrices.

Anchor Warp Point Detection

As with the cranial defect margin crestline points on the template and patient skull surfaces, anchor warp points are determined by the ray-surface collision detection technique [Wern 94]. These rays are cast externally from pre-specified points as shown in FIG. 13. FIG. 13 shows anchor warp points detection. Five anchor points are detected. They will be invariant over the TPS warp, thereby preserving template convexity. The defect margin is uniformly subsampled, and then divided into four intervals in this case. Points mi in the midpoint between the defect margin centroid c and points $d_{i/4n}$ cast rays externally in direction of $n_B$, which is the best-fitting plane of the cranial defect margin. The ray-surface collision locates the points with white-filled circles that are the anchor warp points FIG. 13 shows the detection of five anchor warp points, depicted as white-filled circles, while the template surface is shown as a dashed gray wire frame. Point d, indicates the $n^{th}$ index of sequentially ordered and subsampled cranial defect margin points, and the direction of the ray is heading external and parallel to the cranial defect margin crestline's best fitting plane normal, $n_B$. Point c is the centroid of the defect margin, and point mi is a midpoint defined along the line between c and $d_{i/4n}$. In similar fashion, the number of anchor points can be increased or decreased by uniformly dividing the subsampled defect margin crestline point sets. In order to extract only points at the external surface of the mirrored skull template, the scheme is reused as presented in the previous section. FIG. 13 also depicts the defect margin crestline points, $d_n$, which cast rays in either direction for local point correspondence detection.

The effect of the anchor warp points is that when the first pass global warp using manually located anatomical landmark configurations is omitted, the result of the second pass local TPS warp may present biased deformation. Where no anchor points are used in the second pass warp following the first pass warp, the skull template surface might be flattened when compared with the contra-lateral side. The resulting prosthetic implant may possibly compress the underlying brain in addition to providing a poor aesthetic outcome.

When the warp is constructed with a configuration matrices containing a plurality, i.e., 9 anchor points, the cranial defect margin crestline points, and the full anatomical landmark configuration, the left-right symmetry is improved, while the template surface has a reasonable continuity with the defect margin. When even more radially- or grid-distributed anchor points are used, approximately double the number in the previous case, little or no difference has been seen in the result. We determine the necessary anchor-point density in this fashion.

After inserting the new "second" warp point pairs (i.e., cranial defect margin crestline and anchor warp point pairs), the template surface is globally unwarped along with these new warp point pairs. Since these points were detected after the first pass TPS warp, they need to be realigned to their original configuration following the second pass TPS warp. The configuration matrices of the second pass TPS warp integrate the newly found warp points with the previously located global anatomic landmark configuration. Then the template is re-warped based on the updated landmark configuration matrices. This second pass TPS warp results in better skull template surface convexity than the first pass alone and maintenance of continuity of curvature across the cranial defect margin.

Cranial Implant Surface Smoothing and Edge-to-Surface Articulation

Based on methods presented above, a cranial prosthetic plate can be fabricated via stereolithography. However, the resulting implant model presents several deficiencies, which are resolve by introducing new algorithms. Among the deficiencies, are: 1) there is global irregularity of the polygonal mesh presented in the implant CAD data that may cause poor quality RP production; 2) the inheritance of slice-edge artifact by the left-right mirrored skull template from the patient's original $C_T$ data; and 3) surface curvature discontinuity that appeared in the area near the defect margin crestline, where the implant must accurately articulate with the patient's skull. Therefore, below we describe: (1) a method for resampling the skull template surface to have uniformly shaped and spaced triangles; (2) an effective implant surface smoothing algorithm that removes slice edge artifact; and (3) the articulation of the prototype cranial implant surface while maintaining surface curvature continuity across the cranial defect site.

Among known 3D mesh smoothing algorithms, a method referred to as Laplacian flow, or an umbrella operator, is popular due to its simplicity, speed, and effectiveness in most applications. A Laplacian flow repeatedly or simultaneously moves each point in a polygonal mesh by a preset factor based on the difference from the average of all neighboring points. The algorithmic simplicity of Laplacian flow smoothing has motivated a number of modified schemes, such as Taubin smoothing using alternating scaling factors [Taub 95], and mean curvature flow, a scheme that utilizes-each point's mean curvature and its normal direction as weighting factors [DMSB 99]. More recently, an improved Laplacian flow scheme that pushes modified points back toward their original location [VoMM 99], and a method that hybridizes the Laplacian flow and curvature flow were reported [OhBB 01]. However, there are drawbacks in all of these schemes such as surface shrinkage, lack of local control, and increase of mesh irregularity. Laplacian flow causes unintended distortion of the surface especially in irregular meshes with non-uniform point density. Since the Wrapper algorithm [GuDe94] employed to produce patient isosurface images is an adaptive mesh triangulation algorithm (i.e., more highly curved surfaces are assigned large numbers of small triangles), Laplacian flow based smoothing methods are not suitable.

An additional problem of using Laplacian flow based smoothing methods is that the resulting surface topology structures are not useful for our purpose. Moktarian et al. [MoKY 01] propose a different smoothing approach performing reconstruction of semi-geodesic coordinates as a regular quadrilateral mesh to which we can apply a 2D Gaussian convolution. Although, the resulting surface better fits our topology structure, it has been determined that the degree of mesh regularization can be improved by completely resampling the surface with a ray-surface intersection detection scheme. Then, smoothing can be accomplished by running a 2D low-pass spatial filtering [GoWo 92] on the resampled, and now regular, quadrilateral mesh.

Once a smooth implant template surface is obtained, it is mapped with the space curve representing the skull defect margin crestline obtained as described before. This space curve describes the actual location where the implant must attach to the cranial defect site. The cranial defect margin crestline eventually acts as a 'cookie cutter' when it is used for obtaining the prototype implant surface from the skull template. In order to preserve implant-to-patient surface curvature continuity across the defect margin, surface area in the skull template that extends beyond the defect margin crestline is included during smoothing. An obvious way to preserve surface curvature continuity in this case would be to directly clip the prototype implant surface from the smooth skull template surface using constructive solid geometry (CSG) Boolean operations [Hoff 89]. However, this operation usually requires detection of the pair-wise intersection of polygons and neighbors analysis related to boundary determination of the B-rep. This operation is computationally expensive [MaLC 01b] and therefore not suitable for complex clinical isosurface images composed of hundreds of thousands of polygons. In order to enhance the running time of these operations, a recursive polyhedral partitioning algorithm using bounding boxes for intersection determination was proposed by Segal and Sequin [SeSe 88]. Also, a CSG intersection processing algorithm dedicated to triangular primitives [Hubb 91] has shown enhanced performance, and a smaller number of resulting triangles.

In order to use these CSG based algorithms, each entity must be a valid B-rep, such as a set of triangles. However, the cranial implant CAD software of the present invention must partition the implant surface from the polygonal mesh skull template along the previously determined cranial defect margin space curve represented as edge segments. Moreover, the edge segments are unlikely to intersect actual points in the skull template surface mesh (i.e., they are more likely to pass through only edges and faces). Thus, a new partitioning scheme is disclosed that divides the polygonal mesh surface along the defect margin space curve rather than with another polygonal mesh.

Methods

Slice-Edge Artifact on CT-Derived Polygonal Mesh Surfaces

Isosurface image building algorithms for medical volumetric images, such as Marching Cubes [LoCl 87] or the Wrapper [GuDe 94], are commonly applied to source image data with anisotropic voxel dimensions. Anisotropic voxel dimensions are common, for example 0.5×0.5×1.5 mm, in the X-, Y-, and Z-axes, respectively. $C_T$ slice-edge artifacts that result from Z direction anisotropy are visible in the isosurface image as a series of jagged staircase shapes. These $C_T$ slice edge artifacts are usually most apparent at the top of an axially scanned cranium, the portion where a cranial prosthetic implant is most likely to be needed. Interleaving interpolated $C_T$ slices before isosurface construction may reduce the severity of slice-edge artifacts, but it is difficult to eliminate them, especially with a 3:1 within: between slice resolution ratio as in the example voxel resolution listed above. In addition, an unintended effect of smoothing by over-sampling $C_T$ voxels is that most calculations become computationally expensive.

A practical assumption is made that the areal extent of a cranial defect covers less than half of a sphere to facilitate modeling of the cranium as a sphere. An assumption for a convex hemisphere surface also allows the use of unidirectional ray-casting to resample the surface. These rays are cast from regularly spaced grids in a single plane located external to the surface to be resampled. This resampling scheme not only re-tessellates the skull template isosurface image with a regular quadrilateral pattern, but also establishes a basis for utilizing a 2D image smoothing technique.

Mirrored Template Surface Smoothing

Surface Re-Alignment and Template ROI Surface Clipping

Figure 14B:
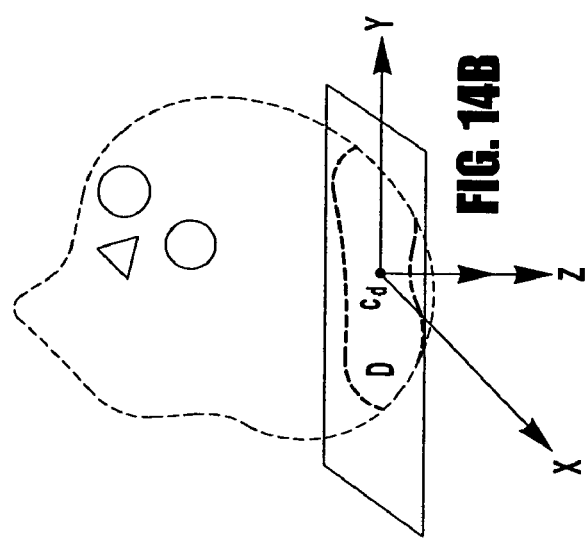
FIG. 14A-14D shows the use of Skull Template ROI Clipping in accordance with the present invention.
Figure 14D:
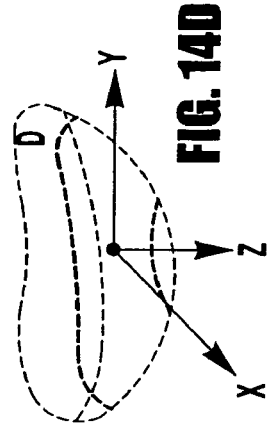
Figure 14A:
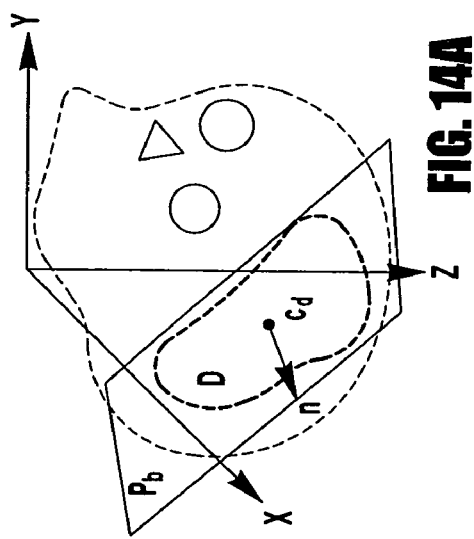
Figure 14C:
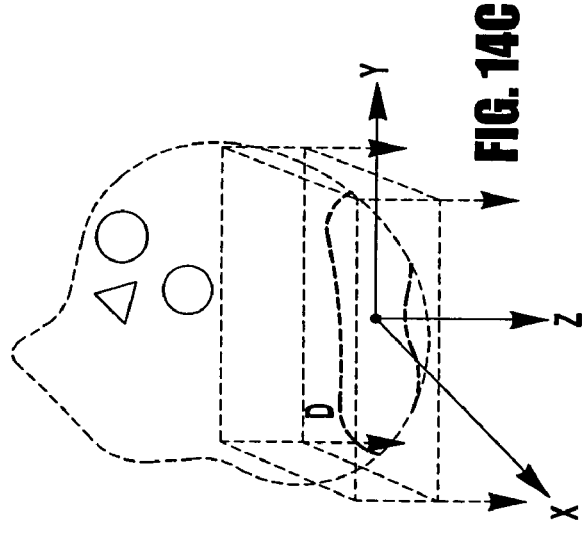

The smoothing process is initiated by registering the defect margin space curve onto the homologous site of the template cranium isosurface (See FIG. 14A). FIGS. 14A-14D show skull template ROI clipping. FIG. 14A shows the original axial scan orientation of the patient to the $C_T$ scanner's X, Y, and Z dimensions. The normal vector n of the best fitting plane $P_b$ for cranial defect margin crestline D is determined. FIG. 14B shows the normal vector n at the centroid, $c_d$, of the defect margin space curve is translated and rotated to be superimposed with the Z-axis at the origin of the coordinate. Note that the alignment of vector n and the Z-axis are used to orient $P_b$ to be perpendicular to the Z-axis. FIG. 14C shows a bounding box embracing the defect margin is extended 1 cm in X, Y, and internally along Z. The bounding box, with infinite depth, is used to clip the template surface ROI. FIG. 14D shows the isolated skull template ROI.

The normal vector n is calculated for the best fitting plane for the defect margin space curve with Newell's algorithm [Tamp 92]. Next, the template surfaces are aligned so that the vector n becomes parallel to the Z-axis. This realignment provides a uniform interval between ray-casting points that are sufficiently normal to the convex surface of interest. The realignment is done through a 3D rigid body transformation matrix $R=R_x R_y T$, which includes one translation and two rotations (See FIG. 14B). The matrix translates the defect centroid $c_d$ to the origin of all three axes. Next it rotates the cranium about the Y-axis so that n lies in the XY-plane, and then rotates about the X-axis so that n lies along the Z-axis. The required angle for each rotation is calculated from the projection image of n onto the XY-plane and the X-axis, respectively [FvFH 90]. In order to acquire the template ROI surface, a rectangle surrounding the defect margin is determined by calculating the minimal and maximal X and Y position of the defect margin space curve in a best-fitting plane. The bounding box is extended 1 cm on all four sides, and then extend an additional 1 cm at the most internal point of the defect margin space curve along the positive direction of the Z-axis (See FIG. 14C). The surface inside this bounding box is extracted with an infinite depth (i.e., minimal Z-plane is not defined) clipping plane that extend outward from the skull centroid (See FIG. 14D).

The cranial defect margin is then registered to the skull template surface. The X and Y plane clipping is done after realignment of the template surface with respect to the best fitting plane of the cranial defect margin space curve. As a consequence of the realignment, the best fitting plane is now parallel to a grid plane with regularly spaced elements. Both the best-fitting and grid planes are also perpendicular to the Z-axis. Surfaces external to the maximum value of the defect margin in the Z direction are then removed to leave the desired skull template ROI. Then the final position of the skull template is ready to be resampled by a ray-surface intersection detection.

Surface Re-Sampling and Smoothing

Figure 15A:
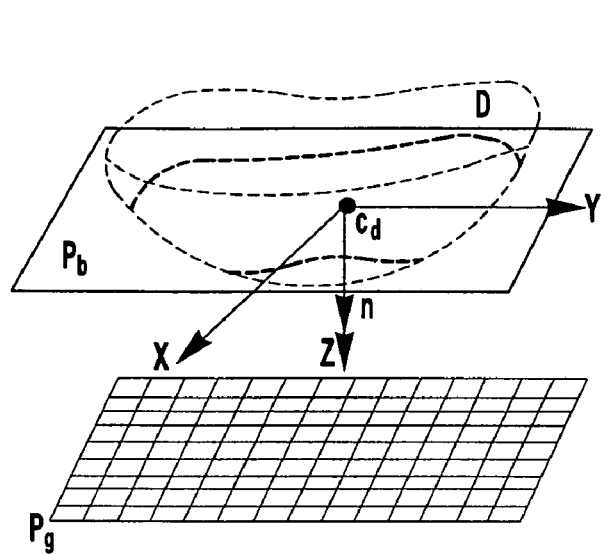
FIG. 15A-15B shows re-sampling and smoothing of the skull template surface ROI in accordance with the present invention.
Figure 15B:
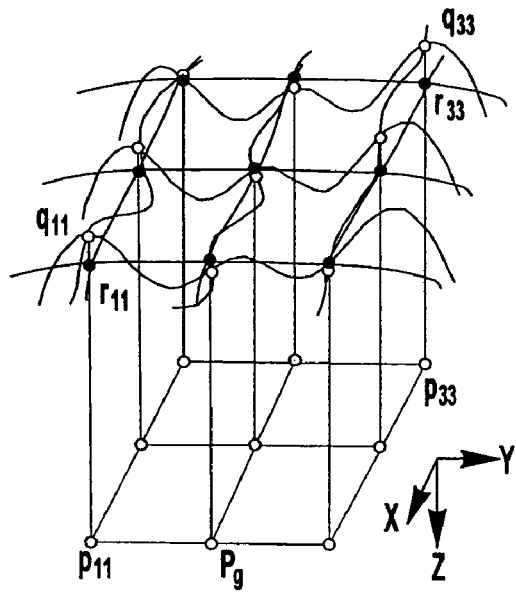

Resampling and smoothing of the clipped template surface ROI begins by casting rays from the Z-aligned plane that is external to the ROI. This plane includes grid points arrayed at a resolution below that of inter-slice thickness for resampling and subsequent smoothing (FIG. 15A). Setting the sampling rate below twice the inter-$C_T$ slice thickness will facilitate removal of slice-edge artifacts present in the skull template ROI. Linear rays are cast in Z direction from the regularly sampled grid points in the plane $P_g$ onto the skull template surface (FIG. 15B). FIGS. 15A-15B shows resampling and smoothing of the skull template surface ROI. FIGS. 15A shows the configuration of the regularly sampled grid plane, $P_g$, external to the template surface ROI. We denote D as the cranial defect margin crestline and $P_b$ as the cranial defect margin best-fitting plane. In FIG. 15B a ray is cast parallel to the Z-axis from point $p_{ij}$ and collides at point $q_{ij}$, thereby resampling the template surface. Resampled point $r_{ij}$ shows shifted locations of $q_{ij}$ after smoothing. Positional information of $r_{ij}$ is recovered by a parametric line equation defined from these three points.

Specifically, a ray is cast from each regularly sampled grid point. It measures the Euclidean distance to the template surface during template surface resampling. Then a matrix M is constructed with i rows and j columns representing a depth map to store the measured distances.

Next the position of a grid point at the $i^{th}$ row and the $j^{th}$ column of the regularly sampled grid plane $P_g$ be $p_{ij}=p(x_{ij}, y_{ij}, z_{ij})$, and the position of intersected subsampled points be $q_{ij}=q(x_{ij}', y_{ij}', z_{ij}')$, then the depth information of M at the $i^{th}$ row and the $j^{th}$ column can be defined as:

$$M_{ij}=\|p_{ij}-q_{ij}\|=z_{ij}-z'_{ij} \quad \text{Equation 4.1}$$

Note the representation of M is equivalent to an intensity image of size m×n, where $1 \leq i \leq n$ and $1 \leq j \leq n$. This property facilitates use of the 2D image techniques such as bilinear interpolation and mask-based spatial smoothing filter. Thus, the density of points in the grid in M is increased to (2n−1)×(2m−1) with bilinear interpolation and then apply a 2D low-pass filtering mask to smooth the skull template surface [GoWo 92]. The process of spatial low-pass filtering is applied to M as follows:

$$N=L_{kk}*M, \text{ where } L_{kk} \text{ is a } k \times k \text{ spatial low-pass filter convolution mask.} \quad \text{Equation 4.2}$$

The final smoothing step is reconstruction of a quadrilateral surface mesh via recovery of positional information from points composing the original skull template surface. The conversion of this depth map into positional information of the projected grid points is accomplished by defining a parametric line equation from point $p_{ij}$ to $q_{ij}$ as:

$$l(t)=(1-t)p_{ij}+tq_{ij}, \text{ where } 0 \leq t \leq 1 \quad \text{Equation 4.3}$$

The newly defined positional information of the surface corresponding to the $i^{th}$ row and the $j^{th}$ column of the smoothed depth map S is denote $r_{ij}=r(x_{ij}'', y_{ij}'', z_{ij}'')$. The ratio of $\|p_{ij}-r_{ij}\|=N_{ij}$ and $\|p_{ij}-q_{ij}\|=M_{ij}$ can be used as a parameter for the line equation, which determines the position of point $r_{ij}$. Since the positions of two points, $p_{ij}$ and $q_{ij}$, are already known, Equation 4.4 can be derived from Equation 4.1 and Equation 4.3, thereby determining $r_{ij}$ as:

$$r_{ij} = \frac{N_{ij}}{M_{ij}}(q_{ij} - p_{ij}) + p_{ij} \quad \text{Equation 4.4}$$

Note that the surface is reoriented to allow ray-casting parallel to the Z-axis of the defect margin's best-fitting plane. This also implies that the parametric line, $p_{ij}$ to $q_{ij}$, can be defined parallel to the Z-axis. This allows an arbitrary value for the Z-component of $q_{ij}$ (i.e. $z_{ij}'$) together with the i and j corresponding components (i.e., the $x_{ij}'$ and $y_{ij}'$) to be used for calculating $r_{ij}$ [FIG. 4(b)]. This useful property can be applied to any $r_{ij}$ where the exact position of the corresponding $p_{ij}$ is unknown, such as at points generated via bilinear interpolation. Transformation of the new smooth skull template surface ROI through matrix $R^{-1}$ is necessary to restore its original orientation. This repositioning subsequently registers the implant template ROI surface to the cranial defect.

Quadrilateral Patch-Based Surface Reconstruction (Needed to do Cookie Cutting)

Figure 16:
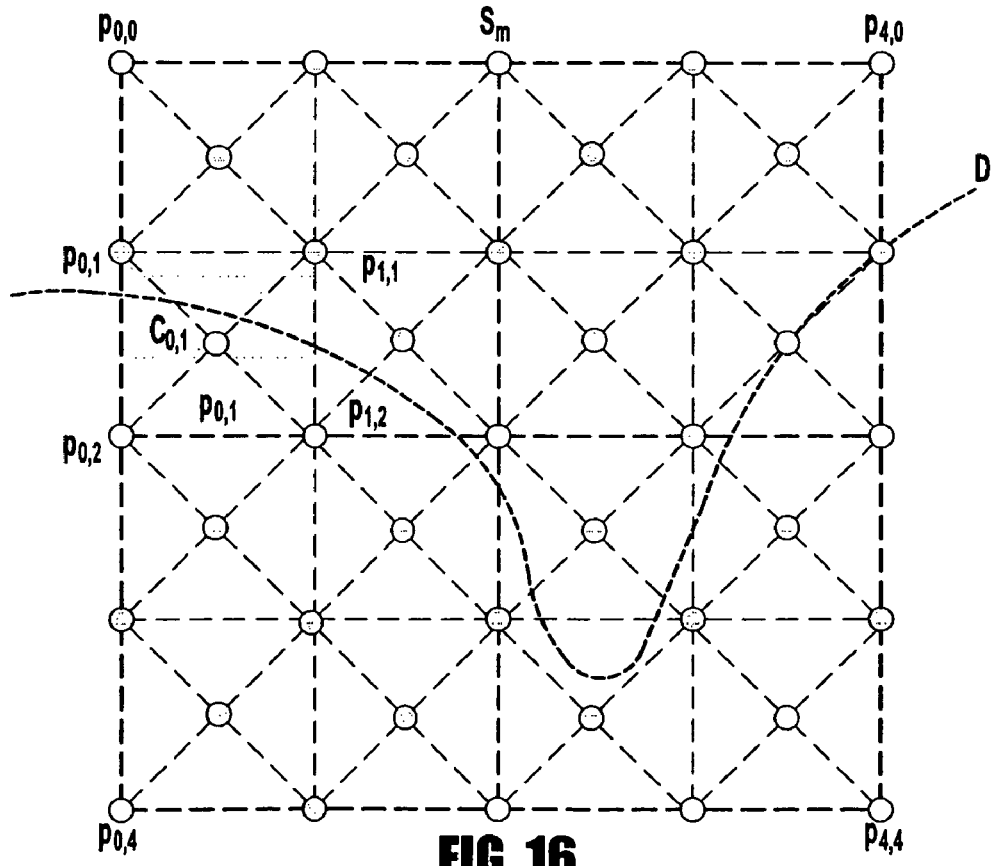
FIG. 16 shows the cranial defect margin space curve D crossing over the Single Gray Patch $P_{0,1}$ of the smoothed and resampled surface $S_m$ in accordance with the present invention.

Additional bilinear interpolation at points-corresponding to the resampled skull template ROI surface $S_m$, results in a quadrilateral pattern (FIG. 16). In FIG. 16 the Cranial Defect Margin Space curve D crosses over the single gray patch $P_{0,1}$ of the smoothed and resampled surface $S_m$. White circles represent resampled points and gray circles represent bilinearly interpolated points. Note that the four triangles in each quadrilateral patch share a single centroid point. The centroid point is adjusted during the defect margin crestline-to-template surface articulation process. Each quadrilateral embeds a recurring pattern of four triangles throughout the revised polygonal mesh skull template ROI surface. If the number of subsampled points were originally n×n, then the subsequent number of points that comprise the skull template ROI surface by the bilinear interpolation becomes $O(n^4)$. The resulting template ROI surface is a single layer triangular mesh, and its regular quadrilateral triangle mesh topology structure provides the basis for articulation of the smoothed skull template and the cranial defect margin space curve. The topology structure of the smoothed skull template surface consists of regularly arranged quadrilateral patches, each embedding four triangles, as seen in FIG. 16.

In FIG. 16 notation $p_{ij}$ indicates a patch corner point at the $i^{th}$ column and $j^{th}$ row of the quadrilateral surface, and $P_{ij}$ indicates a quadrilateral patch having point $p_{ij}$ as its left-top corner vertex. Four triangles in each quadrilateral patch share a centroid point, where point $c_{ij}$ is the centroid of patch $P_{ij}$.

Surface Articulation

Although the skull template ROI is now smoothed and resampled, if one simply removes triangles intersected by the defect margin crestline small gaps will be found between the template surface and the points composing the cranial defect margin space curve. Therefore, accurate articulation of the skull surface and the cranial defect margin requires an effective method for mapping the cranial defect margin space curve points onto the skull template surface. Based on the mapping of the cranial defect margin crestline points, the new regularly resampled topology of the smooth template surface is partitioned via vertex insertion and quadrilateral centroid point adjustment. A doubly-linked list data structure, L, is employed to track candidate patches that require adjustment of their centroid points and subsequent partitioning.

Implicit Characterization of Patch Structure

Figure 17:
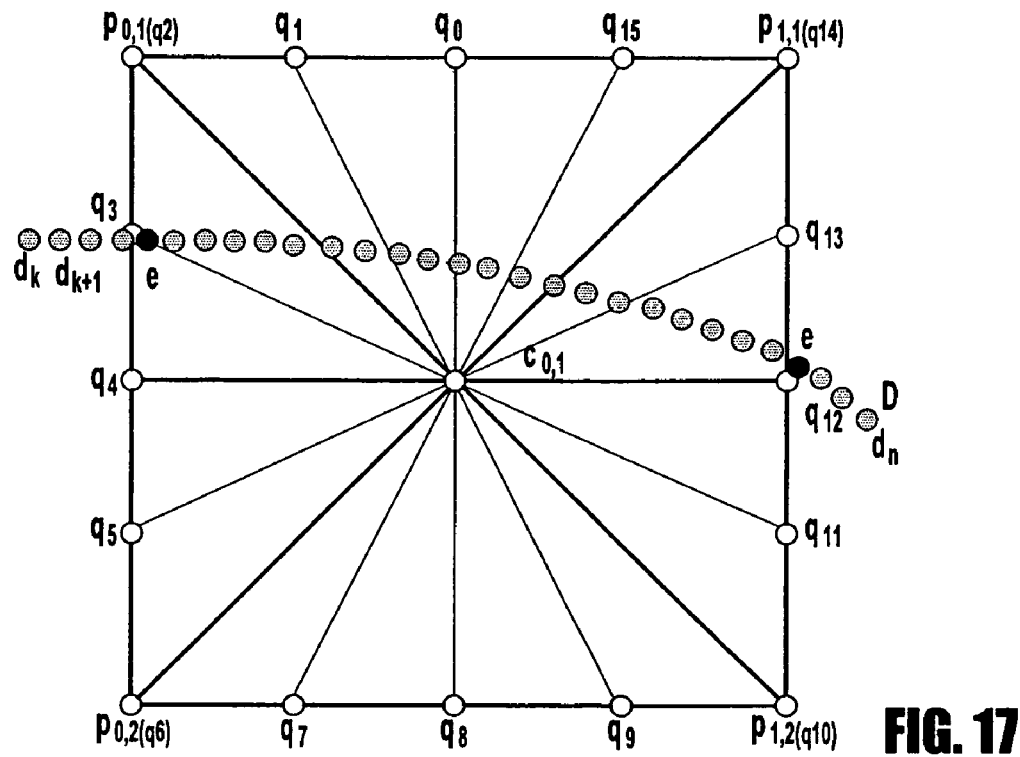
FIG. 17 shows the implicit structure of a quadrilateral patch $P_{0,1}$ in accordance with the present invention.

The articulation algorithm is started by mapping the smoothed and resampled template surface $S_m$, with a set of patches $P=\{P_{ij}|P_{ij}=(p_{i,j}, p_{i+1,j}, p_{i,j+1}, p_{i+j+1}, c_{i,j})\}$, where $p_{i,j}$ represents a point in surface $S_m$ that corresponds to the $i_{th}$ row and the $j_{th}$ column of the depth map. $c_{ij}$ is denoted as the centroid point of a patch $P_{ij}$, and the set of cranial defect margin space curve points as $D=\{d_k|d_k=\{x_k, Y_k, z_k\}\}$, where $0<k<n$. FIG. 17 shows the implicit structure of a quadrilateral patch $P_{0,1}$. $P_{0,1}$ is composed of four-corner points, $p_{0,1}$, $p_{1,1}$, $p_{0,2}$, $P_{1,2}$, and a centroid point, $c_{0,1}$. Among the points $d_k \in D$ that sequentially form the defect margin space curve D, a pair of points e (black) are determined to be the points that enter and exit patch $P_{0,1}$. From the four corner points of the quadrilateral, uniform interval points $q_0$ to $q_{15}$ are located. These points implicitly predefine eight different line segments within the patch. Note that $P_{0,1}$ is depicted as a gray quadrilateral patch in FIG. 16.

Then, intervals of four vertex points for each patch are implicitly subdivided by points indexed from $q_0$ to $q_{15}$ to define dashed projection line segments that allow centroid point adjustment. The nearest neighbor correspondence between D and $c_{ij}$ will determine the patches to be partitioned later. Whenever there is a change in the corresponding nearest patch to any point in the defect margin space curve, D, We add patch $P_{ij}$ to the linked list L.

Throughout the remaining discussion, the correspondence between P and D change as entering and exiting points e ∈D of P. Note that an exiting point of one patch is also the entering point of the subsequent adjacent patch.

Defect Margin Correspondence with Template ROI Surface Patch

Figure 18:
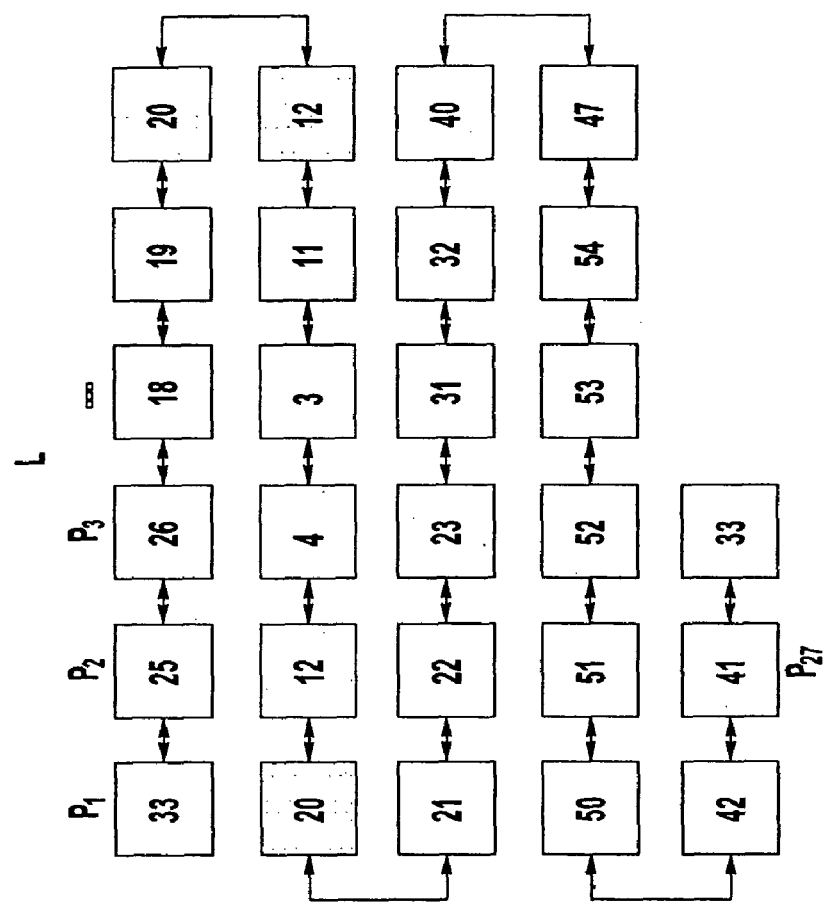
FIG. 18 shows a defect margin corresponding patch list in accordance with the present invention.

The regular patch structure of the skull template ROI facilitates serial detection of correspondence between quadrilateral patches and the defect margin space curve D. The correspondence is determined by sequentially detecting nearest neighboring patches from each $d_k \in D$. The corresponding skull template ROI surface patches are archived in a doubly-linked list $L=\{P_1, P_2, \ldots P_n|P_i$=(patch_id, prev_ptr, next_ptr)$\}$, which is in sequence as one would traverse along the defect margin space curve, D. Each $P_i$ in L has three tuples that store its patch identifier, a pointer to which it references previously visited patch, and a pointer to which it references the next traversed patch. A new patch in list L is added only if the patch identifier differs from that of the previously checked defect margin point $d_k$. FIG. 18 presents an example of a defect margin space curve registered to the skull template ROI surface, where the initial point on D is found in patch identifier 33. FIG. 18 shows the building defect margin corresponding patch list. A doubly-linked list L is built from the defect margin corresponding patches (gray). The sequence of the patches in list L reflects the direction in which defect margin correspondence is located. The first and the last patches in L must be identical to validate the fact that corresponding patches compose a closed contour, as indicated by D. Note that patch identifier 12 and 20 (gray) are located twice in list L, a situation which requires refinement in subsequent steps.

Table 4.1 summarizes the algorithm used to archive the doubly-linked list L which contains patches in the resampled skull template ROI that correspond to the defect margin space curve.

TABLE 4.1

Defect Margin Corresponding Patch List Building Algorithm:

1. From an arbitrary point of the cranial defect margin crestline $d_i \in D$, find the closest patch centroid among patch set P. Add $P_j$ in a doubly-linked list L, with a patch identifier, a previous pointer, and a next pointer. The initial patch should have a null previous pointer.
2. Repeat the steps from 3 to 5 until there are no more cranial defect margin sampled points d ∈ D
3. Check the adjacent point $d_{i+1} \in D$ to determine the closest patch center.
4. If the identifier is identical to $P_j$ in L, then increase i by one.
5. If the identifier is different from $P_j$, then add $P_{j+1}$ in L, and set $d_{i+1}$ as the entering point of $P_{j+1}$ and exiting point of $P_j$.

Figure 19:
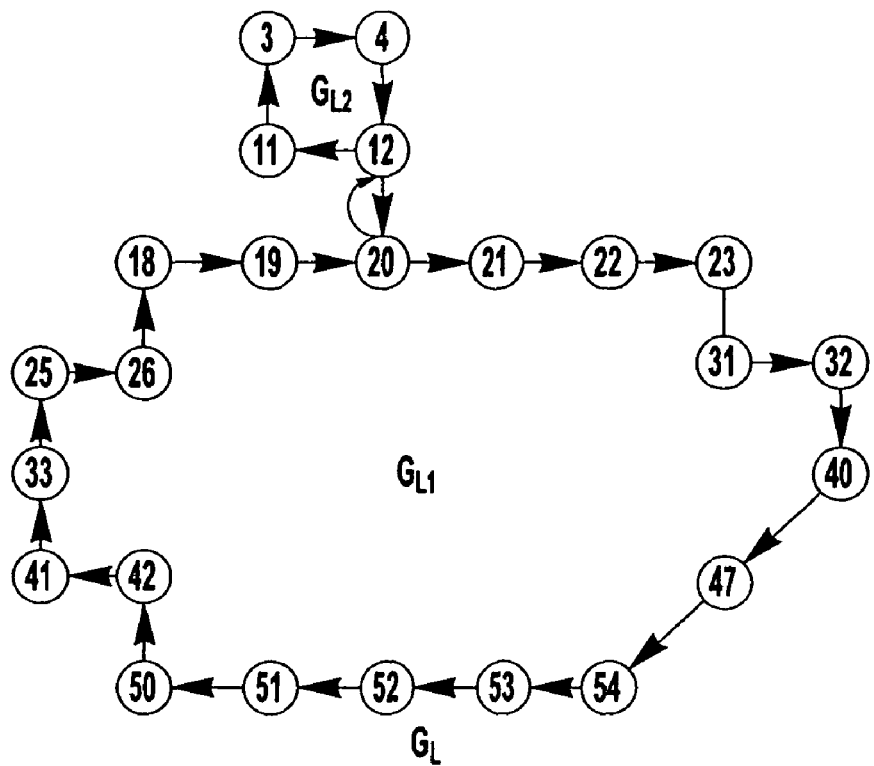
FIG. 19 shows a graphic representation of the defect margin corresponding patch list in accordance with the present invention.

While building the cranial defect margin corresponding patch list, one may find out that some patches are occasionally traversed twice by D, and thus are duplicated in L as well. These patches are indicated by gray in list L on the right side of FIG. 18. This situation is depicted more clearly when list L is represented as a directed graph, $G_L$ (V, E), where V is a set of vertices and E is a set of edges with the same serial direction. Each patch in list L corresponds to each vertex in set V, and each pointer referencing the next patch in L defines a directed edge in set E. FIG. 19 shows list L in FIG. 18 represented as the directed graph $G_L$. FIG. 19 shows a graph representation of the Defect Margin Corresponding patch list. Patch list L is represented as a directed graph $G_L$, where $G_L$ can be divided into two sub-graphs $G_{L1}$ and $G_{L2}$. All vertices other than the gray ones linking $G_{L1}$ and $G_{L2}$ have a degree of two.

During the conversion from L to $G_L$, pointers that reference the serial direction of the traversed patches are converted to a directed edge. By Steps 4 and 5 in Table 4.1, each next pointer must have one-to-one correspondence with an entering and exiting point pair. Because each directed edge imposes one in-degree (i.e., vertex degree of incoming edge) and one out-degree (i.e., vertex degree of out-going edge) per vertex, an entering point is equivalent to an in-degree, and an exiting point is equivalent to an out-degree of the relevant vertex in $G_L$. Consequently, patches with multiple entering and exiting occurrences are represented as vertices with multiple vertex degrees (gray) in $G_L$. Edges between these vertices link two sub-graphs, $G_{L1} \subset G_L$ and $G_{L2} \subset G_L$, both having a single vertex degree. Under an assumption that each quadrilateral patch is sufficiently small (i.e. <4 mm$^2$), implant surface partitioning along these multiple entering and exiting points would result in sharp edges, or a narrow protrusion that is undesirable as an implant rim definition. Thus, these multiply crossed, overly complex regions are multiplied by simplifying them to have only a single pair of entering and exiting points, e. In terms of a graph representation of the patch list L, this simplification process essentially removes smaller sub-graphs, such as $G_{L1}$, which are linked by a vertex of multiple degrees to the largest sub-graph, $G_{L2}$. This path simplification process also facilitates the simplicity and efficiency of our surface-partitioning scheme.

Defect Margin Path Simplification in Template ROI Surface

The main objective of cranial defect margin path simplification is to leave only one corresponding patch in list L, with a unique identifier. Table 4.2 shows a summary of the path simplification algorithm using back-tracking along the links in list L.

TABLE 4.2

Defect Margin Path Simplification Algorithm:

1. From the doubly-linked list L, find an identifier of a patch that has the longest interval before its reappearance in L.
2. Select the next patch with previously located initial starting point patch for the simplification procedure.
3. Repeat the following steps from 4 to 6 until the pointer reaches the end of L.
4. Check if the hash table has an identifier of the currently visited patch in L.
5. If so, then backtrack until it reaches the identical patch. While back-tracking, delete all intermediate patches in L. Update the next pointer.
6. If not, then store its identifier in the hash table. Visit the next patch.

Figure 20:
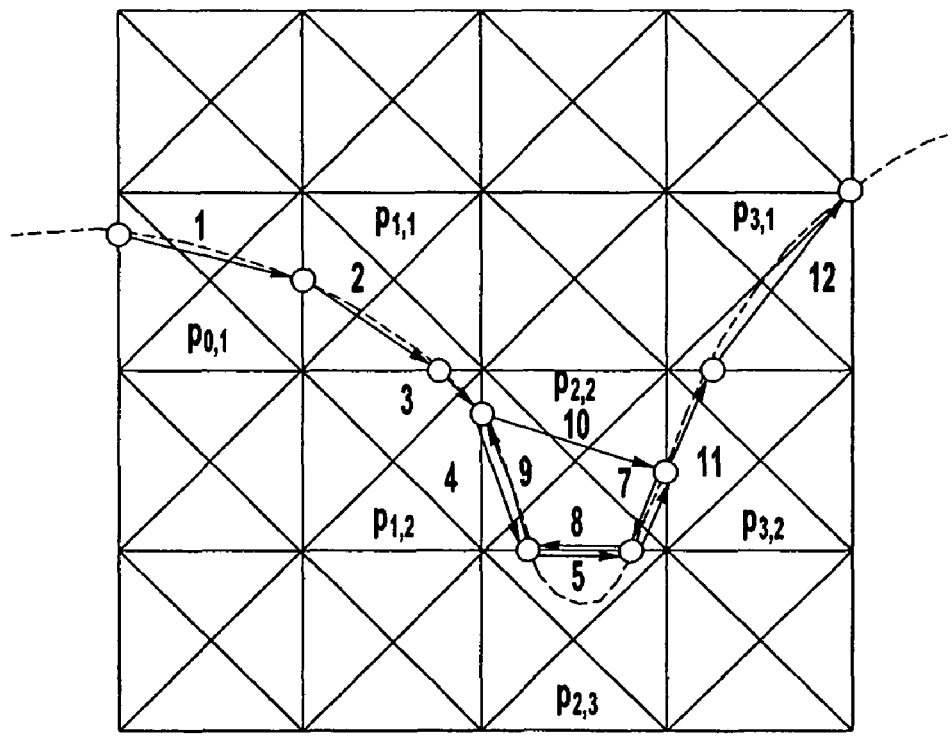
FIG. 20 shows a cranial defect margin path simplification in accordance with the present invention.

The simplification process begins by pre-scanning L and then picking a patch that is the starting patch of the maximum length without multiple entering and exiting point pairs at Step 1 and Step 2 in table 4.2. If no reappearance is detected, then the algorithm is terminated. Next, we scan patches in L along one direction and register a scanned patched identifier in a hash table. When previously registered identifiers are found in the hash table, we invoke recursive backtracking along the reverse path at Step 5 of Table 4.2. We delete the intermediate path once the previous node with the identical patch identifier is encountered. Links of the disconnected patches are restored, and then the hash table is updated (FIG. 20). FIG. 20 shows cranial defect margin path simplification. Multiple entering and exiting point pairs are removed so that each patch has only one pair. The dashed gray line shows the original path of the defect margin across the skull template surface. The solid black arrows represent the direction of the simplified path. The path through patch $P_{2,2}$ with double entering and exiting points is simplified to have a single pair of e. The line segment numbers show the stepwise determination of the simplified path. Note that the path traversed during steps 4 to 9 (dotted arrows) is removed following the backtracking step. A notch is consequentially removed and replaced by a smoother line segment at step 10 by updating the next pointer of $P_{2,2}$ in L.

Scanning for any duplicated patch identifiers in L is continued until the analysis returns to the initial patch in L. Note that when a patch is re-entered, the previously scanned entering point becomes the newly valid entering point. This fact implies the possibility of refinement leading to a local cycle in $G_L$ when the scan is initiated from an inappropriate patch (i.e., a patch that should be deleted during back-tracking). To avoid this local cycle, pre-scanning at Steps 1 and 2 is done, enabling the subsequent scanning from a vertex that is part of the largest cycle in $G_L$. In terms of graph $G_L$, the refinement process can be considered as repetitively removing small cycles to leave only the largest cycle, where all vertices have one in-degree and one out-degree.

Cranial Defect Margin Point Projection onto Skull template

Figure 21:
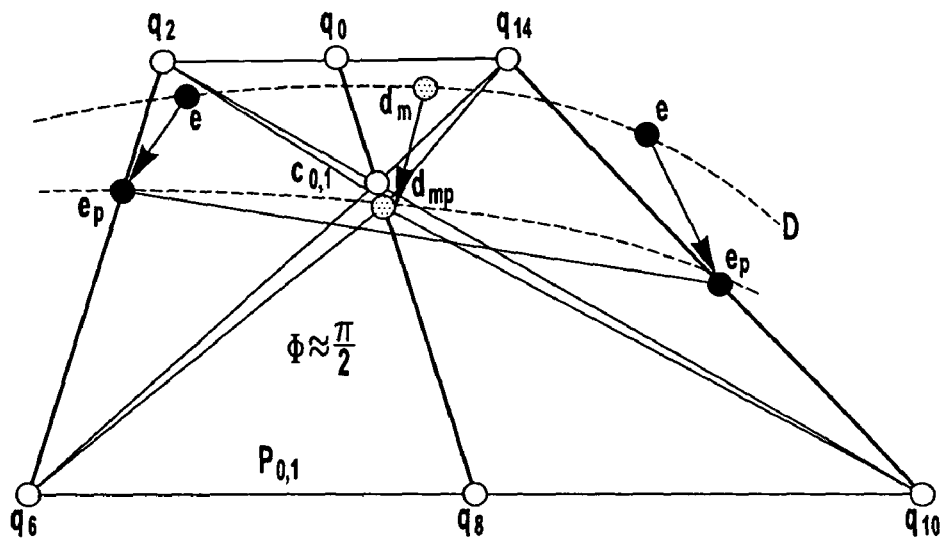
FIG. 21 shows the projection of entering, exiting, and Median Index Points onto Patch $P_{0,1}$ in accordance with the present invention.

The cranial defect margin space curve described above is unlikely to coincide with the skull template surface due to the effect of resampling and smoothing. Therefore, the entering and exiting points of the defect margin are mapped onto the template ROI surface by point-to-line projection. In terms of patches, the projection is done onto the edges or points shared by serially adjacent patches in L (FIG. 21). FIG. 21 shows projection of entering, exiting, and median index points onto patch $P_{0,1}$. The original locations of the entering and exiting points are denoted as points e. These points are projected onto margin-crossing edges as points, $e_p$. The projected point $d_{mp}$ of median index point $d_m$ is approximately halfway between each entering and exiting point pair. The projecting line segment $q_0q_8$ is selected from eight predefined line segments based on its angle against a line segment defined by the $e_p$ pair. The point $d_{mp}$ becomes a new vertex replacing point $c_{0,1}$, which the four triangles were originally sharing previously. The link of these three projected points will eventually form a new border dividing the cranial implant surface and its surrounding skull template surface.

Each median index point $d_m$, between an entering and exiting point pair, is projected onto one of eight predefined line segments (FIG. 17). These new points then become each quadrilateral's new centroid points. A line segment that is approximately perpendicular to the line defined between the projected entering and exiting points is chosen for the centroid point projection. To result in a valid triangulation (i.e., no self-intersecting or flipped triangles), it is important to insure the projected points lie within the quadrilateral patch. Since we perform point-to-line projection, each projection is validated by defining the projection line as a parametric line equation with a parametric range of [0.0, 1.0]. We then check if the parameter value of the projected point lies within this interval. If not, then the point is forced to be placed on either end of the projection line segment.

Implant Template Surface Articulation via Patch Partitioning

Depending on the topological alignment of the projected entering and exiting points, new vertices and edges are inserted on the vertex or edge of triangles composing the patches in the simplified list L. These new vertices and edges subdivide a triangle into two, having a separate membership in terms of connected components. One will belong to the prototype implant surface, and the other to the region surrounding the implant on the skull template surface. Depending on the location of the entering and exiting points, there are three possible cases for placing one or two $e_p$ points on a triangle (FIGS. 22A-22D). FIGS. 22A-22D show three patch elements representing the possible triangle partitioning scenarios. Vertices $p_1$, $p_2$, and $p_3$ are vertices of a triangle in patch $P_{0,1}$ in FIG. 21. Point $e_p$ is the projection of either an entering or exiting point along the defect margin space curve as it traverses a patch. Point c is a centroid point in the quadrilateral patch, equivalent to p3 in this figure. Vertex m is inserted to divide the triangle into two connected components. The dashed line indicates the border where these two new surfaces will be separated. This algorithm introduces, at most, three new vertices, and eight new edges per triangle.

Case 1 applies when the projected entering or exiting point $e_p$ overlaps with a triangle vertex. The partition will be made along a shared edge by adding a vertex m to the edge, and then adding three edges between the triangle vertices and m (FIG. 22A). Case 2 is the most commonly occurring situation, where either the entering or exiting point e lies on one of the four edges of a quadrilateral patch. Vertices $e_p$ and m are added to divide the shared edge (FIG. 22B). Case 3 applies to a rare situation, where the entering point vertex overlaps with an original vertex of the quadrilateral patch and the exiting point vertex lies on an edge, or vice versa (FIG. 22C). Since multiple entering and exiting points on an edge are not allowed, Case 3 is interpreted as a situation when one $e_p$ is on the vertex, and the other $e_p$ is inserted on an edge. Two m points and two corresponding edges are added for partitioning. Note that when one of the $e_p$ vertices is overlapped by $p_2$ instead of $p_1$, the situation is resolved with a combination of Case 1 and Case 2. The default case applies to any triangle of a patch that has no entering or exiting point traversals (FIG. 22D).

Figure 23:
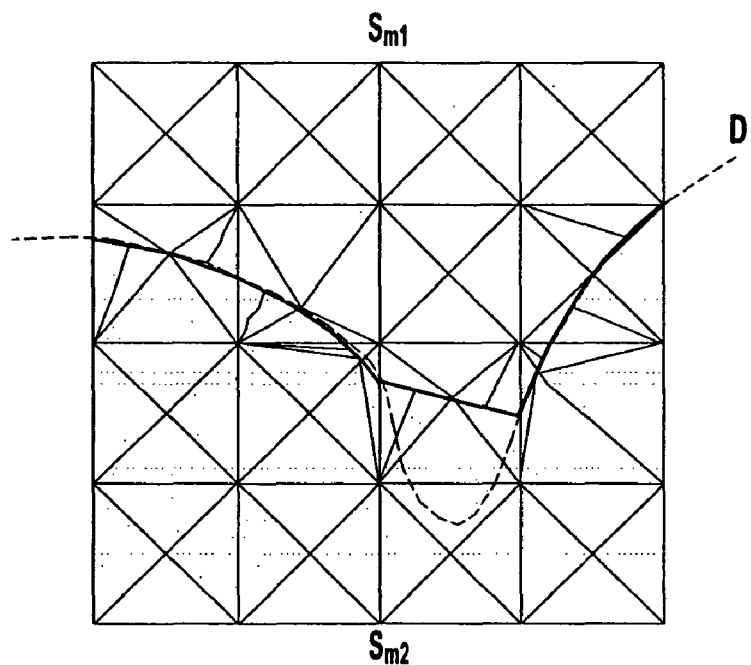
FIG. 23 shows the portioning of surfaces $S_{m1}$ (White) and $S_{m2}$ (Gray is a cross-sectional view), within a right-left mirrored or average skull template, which yields the implant surface and the subsequently unused surrounding surface in accordance with the present invention.

Finally, the newly partitioned surface is represented as a graph $G_m(V, E)$, where V is a vertex set, and E is an edge set. Each vertex in V represents a partitioned triangle, and each edge is included in E is only if a pair of triangles shares this edge. Next, an interactive connected components algorithm [CoLR 90] is run on $G_m$ to discriminate the two independent sub-graphs representing the cranial implant surface, $S_{m1}$, and the rest of the skull template surface, $S_{m2}$ along the simplified cranial defect margin (FIG. 23). FIG. 23 shows the partitioned surface $S_{m1}$. (White) and $S_{m2}$ (Gray). Vertex insertions are made according to combinations of the three possible triangle subdivision alternatives seen in the FIG. 22. The dashed curve indicates the path of cranial defect margin D. The surface is partitioned along the solid black border. Note that the partitioning border does not follow the notch, since it was removed during path simplification. The border of each partitioned patch is composed of two line segments linearly approximating the cranial defect margin space curve.

After the implant surface is extracted, the zero-area triangles that might have been generated if point $e_p$, m, and c were linearly placed on one of four edges of the quadrilateral patch are removed. This is a simple test based on a triangle inequality, checking if the sum of two edges of a triangle is greater than the remaining edge.

Cranial Implant CAD Data Verification and Modification

Next the methods that validate the fit of the prototype cranial implant CAD data are introduced. The prototype cranial implant data resulting from the work presented above is a surface with no thickness. The rim definition of this surface matches the cranial defect margin crestline, which corresponds to the external surface of the final prototype cranial implant design. Adding an internal surface parallel to the external surface, and then interconnecting these two surfaces, introduces an additional surface. This interconnecting surface is found along the implant's edge, which is referred to herein as the taper. The taper is where the implant will contact the patient's cranial defect margin.

This validation not only determines the fit of the prototype cranial implant, but also facilitates modification of either the implant surface or the taper if necessary to improve seating. Clinical experience suggests that care should be taken to insure that the implant does not intersect adjacent structures such as the brain and skull [Bond 02]. Therefore, potential intersections between the implant surface and underlying soft tissue structures are detected and removed via a test referred to herein as implant surface verification. Solid or meshwork titanium cranial implants are often as thin as 1.5 mm, and designed to utilize partial overlap the patient's bone at the defect site [EuSa 01]. The overlapping flap may include screw holes for fixation. However, polymethylmehacrylate (PMMA) cranial implants usually have a thickness greater than 4 mm, requiring inclusion of a taper between external and internal surfaces [Bond 02]. Thus, it is necessary to verify of contact between the taper surface and the defect site, a task which is referred to as implant taper verification. Although others have attempted to verify CAD/CAM fabricated titanium cranial implant seating using skull images and RP (Rapid Prototyping) models [JNRL 99], there is no other work to the inventors' knowledge that validates non-intersection for both surface and taper contact of a CAD cranial implant prior to RP production.

It is tedious at best to insure lack of implant intersection with the patient's tissues via onscreen surface rendering alone. The situation becomes more difficult when contact of the taper is to be visualized. This is because the taper is located internal to the external implant surface when it is seated on the defect site. Therefore, a collision detection technique is used to facilitate verification of proper taper seating as well as non-intersection between that prototype implant and the patient to direct design modification if necessary. Currently, there are a number of fast and robust 3D collision detection algorithms available that are specialized according to system-specific characterization and constraints [JiTT 01]. For the purpose of the present invention, the RAPID algorithm was selected, a polygon-based collision detection algorithm using an oriented bounding box (OBB) tree [GoLM 96], developed by the UNC (University of North Carolina) Research Group. As a constraint, RAPID collision detection is performed between a pair of polygonal soup objects. Polygonal soup objects are a collection of polygons without any topological information. The present CAD approach also uses the polygonal mesh to indicate where each collision occurs by checking in a pair-wise manner, satisfying required specification of the RAPID algorithm. The medical application of OBB tree-based collision detection has previously shown itself useful for determining the constraints of hip motion in surgical planning and simulation of CT- and MR-based polygonal mesh objects [RTEM 99].

Methods

RAPID Collision Detection Algorithm

Figure 24:
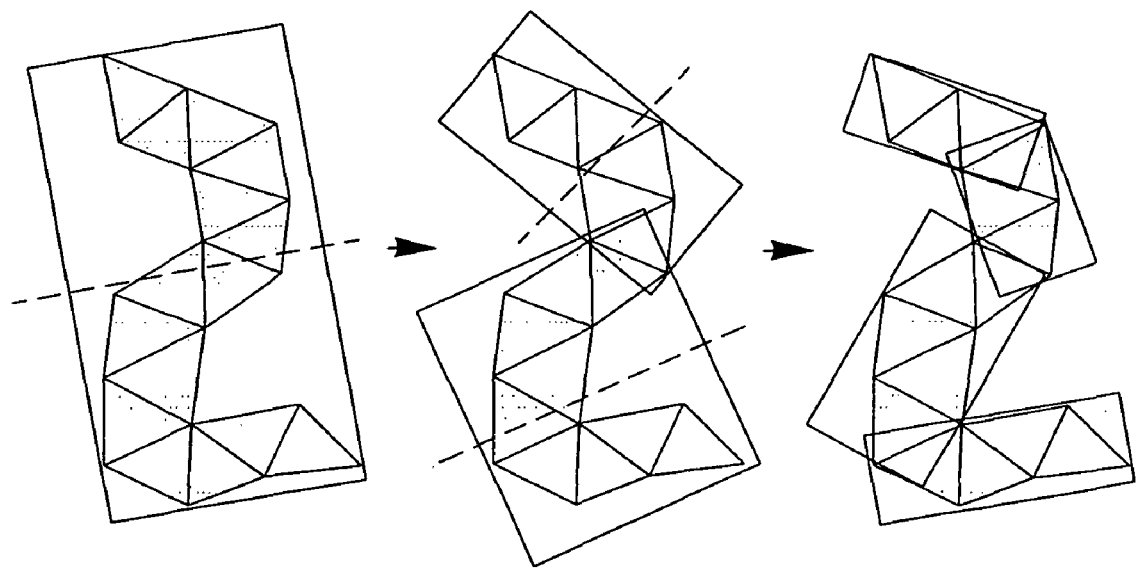
FIG. 24 shows the building an OBB tree in accordance with the present invention.

The RAPID collision detection algorithm is based on an OBB tree data structure proposed by Gottschalk et al. [GoLM 96]. An OBB is a rectangular bounding box having an arbitrary orientation in 3D space. In terms of building a tree, the root of the tree represents a box that entirely encloses the given 3D polygonal structure. The orientation of the box is determined by a statistical calculation of the vertex orientation composing the polygons of interest. The first box is subdivided into two that are oriented independently based on the polygonal sets they surround ( see FIG. 24 where by recursively partitioning the bounding box, a hierarchical tree of an oriented bounding box is generated.

These boxes are then added to the tree as child nodes of the root. Similarly, recursive subdivisions of each box result in a hierarchical tree structure, which is the OBB tree.

Collision detection is initiated by building two separate OBB trees representing the two polygonal objects to be tested. Upon invoking the detection, the two trees are traversed and tested for overlap between oriented bounding boxes based on a principal referred to as the separating axis theorem. The separating axis theorem states that two convex polyhedra are separate, if and only if there is a separating axis orthogonal to a face of either polyhedron, or orthogonal to an edge from each polyhedron. One trivial test for non-overlap is to project the boxes onto a single axis in space. Following this axial projection, each box will form an interval on the axis. If the intervals do not overlap, then the axis is referred to as a separating axis. By the separating axis theorem, the boxes must be non-intersecting in this case. On the other hand, if the intervals do overlap, then the boxes may or may not be disjoint. Full verification requires at most 15 (6 unique faces and 9 pair-wise combination of edges) further testing.

A pair of OBB trees needs to be built only once, prior to invoking collision detection, as long as the polygonal mesh objects are transformed via a rigid body transformation (i.e., rotation and translation). Given a model with n triangles, the running time for building an OBB tree is $O(nlg^2n)$ for using convex hull, and $O(nlgn)$ for not using it. The OBB tree has a depth of $O(lgn)$, which allows a rapid collision detection between large complex geometries composed of hundreds of thousands of polygons interactively.

Implant Surface Verification and Modification

The primary objective of implant surface verification is to ensure that the implant surface does not intersect adjacent soft tissue structures. Thus, the prototype implant surface, $S_p$, and an additional surface representing the dura mater surface, $S_D$, are employed. The dura mater is a flexible fluid-filled layer wrapping the brain. Prior to the patient incurring a skull defect, it was attached to the internal surface of the skull. However, its shape may change following creation of the cranial defect due to brain swelling.

Dura Mater Surface Segmentation

A polygonal mesh surface representation of the dura mater is obtained manually by identifying dura mater pixels seen in the region of the skull defect in the relevant series of cranial CT slice images. CT images may present a low contrast between soft tissue structures, such as the scalp and the brain. Contrast stretching [GoWo 92] is performed between the pixel intensities of these two structures in order to enhance the contrast of the dura mater (FIGS. 25A-25B). FIGS. 25A-25B show dura mater surface segmentation. In FIG. 25A the original appearance of patient head CT scan in the region with a cranial defect is shown. In FIG. 25B the contrast stretched CT scan of (a) is shown. Expanding the histogram between minimum and maximum intensity value of the soft tissue significantly increases the contrast. This allows the operator to identify the dura mater edge inside the defect site.

The pixels identified as the external edges of the dura mater are built into a 3D polygonal mesh via Delaunay triangulation.

Dura Mater Surface Smoothing

The initial dura mater polygonal mesh surface, $S_D$, built by manual segmentation is usually a rather rough surface, especially when CT inter-slice spacing is larger than pixel size.

Resampling and smoothing the surface, $S_D$, is done with the method introduced above. The decreased number of triangles composing the dura mater surface reduces the computational cost for subsequent analyses. Moreover, the smooth dura mater surface facilitates its direct use as a target surface for a TPS warp if implant surface modification is required. Table 5.1 summarizes the dura mater surface smoothing process.

TABLE 5.1

Dura Mater Surface Smoothing Algorithm:

1. Load dura mater surface, $S_D$, and the cranial defect margin space curve data, D simultaneously on screen.
2. Find the normal vector, n, of the cranial defect margin's best-fitting plane.
3. Align $S_D$ so that n is parallel with the Z-axis using a rotation matrix R.
4. Define a regularly sampled grid plane external to the surface.
5. Cast rays from each grid point internally.
6. Detect the ray intersection points on $S_D$.
7. Build a 2D depth-map matrix containing the distances between the grid points and $S_D$.
8. Smooth this depth map using a 2D low-pass imaging mask.
9. Increase point density of the depth map via bilinear interpolation.
10. Convert the depth information back to 3D positional information. Note that the X and Y components correspond to the row and column of the depth map, where as the z component corresponds to the depth.
11. Rebuild the $S_D$ polygonal mesh.
12. Restore the original configuration of $S_D$ via rotation matrix $R^{-1}$.

Since the dura mater is rougher than a left-right mirrored skull template surface or an average skull surface image, a larger X and Y interval (e.g., more than 1.5 mm, which is the CT slice spacing) in the grid can be used during resampling process for computational efficiency. Note that unlike the cranial prosthetic surface, no surface-to-edge articulation is needed since only the surface information is referenced. In step 1 of Table 5. 1, the cranial defect margin space curve, $D=\{d_i|d_i=(x_i, y_i, z_i)\}$, where $0 \leq i < n$ is acquired from the detection method introduced in Section 2.

Implant Surface Verification Using Collision Detection

The RAPID algorithm is used to detect intersections between the dura mater surface, $S_D$, and the prototype implant surface, $S_p$. If no collision or only a minor collision occurs between $S_D$ and $S_p$, then it is assumed that the implant prototype will safely occupy the sleeve between the dura mater and the implant covering the cranial defect site. The implant surface shape requires no further modification in such cases. However, if a contour-shaped collision, that is referred to as a significant intersection, is detected (See FIG. 26A), the dura mater surface will be judged to sufficiently penetrate the implant prototype surface as shown in FIG. 26B. This type of the intersection is likely to prevent the cranial implant from fitting into the cranial defect site. Referring to FIG. 26A when viewed from above, a contour-shaped collision pattern is detected between an implant prototype surface, $S_p$, and dura mater surface, $S_D$. In FIG. 26B, a cross-section through plane P in (a) shows that $S_D$ is penetrating $S_p$. However, when there is sufficient free space under $S_p$, it is assumed that it is to possible to fully enclose the protruding portion of the dura mater surface under the prototype implant.

Before deciding to modify the prototype implant surface, the implant-dura intersections are analyzed using a ray-surface intersection technique [Wern 94]. First the homologous surface points are located between the dura mater surface, $S_D$, and the prototype implant surface, $S_p$. Then, the volume between $S_p$ and $S_D$, is calculated which can be subdivided into separate volumes. One is the portion of $S_D$ that protrudes through $S_p$, and the other is a free space between $S_p$ and $S_D$. The prototype implant surface will be modified, only if the dura mater volume penetrated by the implant is less than that of the volume between the dura mater and the implant. Because these volume calculations are based on points from surface homology mapping, the correspondence between point pairs in $S_p$ and $S_D$ must be known for subsequent TPS warp. Table 5.2 presents summary of the process for locating homologous point pairs between $S_p$ and $S_D$ via ray-surface intersection detection.

TABLE 5.2

Homologous Point Pair Detection between $S_D$ and $S_P$:

1. Place surfaces $S_D$, $S_P$, and the defect margin D in proper positions simultaneously.
2. Calculate the normal vector, n, of the best-fitting plane for D.
3. Reorient all three objects so that n is parallel to the Z-axis.
4. Define a plane $P_G$ with normal vector n, composed of n × m points with identical spacing in the X and Y dimensions, respectively.
5. Cast a ray from each point with direction n. Note that unless the underlying surfaces are folded, there will be at most two collisions per ray with $S_D$ and $S_P$, respectively.
6. Build an n × m volume matrix V based on the rule given in Table 5.3.
7. Store the positions of ray-surface collisions on $S_D$ and $S_P$.

Once the homologous points in the two surfaces, $S_p$ and $S_D$, are mapped, the internal free volume and the protruding dura mater surface volume are calculated via discrete definite integration. To do so, we fit 3D hexahedra between the corresponding points of $S_D$ and $S_p$. FIG. 27 shows a cross-sectional view of these fitted hexahedra, where each hexahedron is depicted as a rectangle. Note that these hexahedra are bounded by rays cast from a regularly sampled grid plane external to both $S_D$ and $S_p$. Because the rays are cast from a grid with regular X and Y spacing, the volume of each hexahedron is proportional only to the length of the ray connecting $S_D$ and $S_p$. An interval along the ray that corresponds to empty space internal to the implant will collide first with $S_D$ and then $S_p$. In contrast, an interval that corresponds to the dura mater penetration external to the implant will intersect $S_p$ first and then $S_D$.

FIG. 27 shows the volume estimation of Dura Mater penetrated space and sub-Implant Space. Rays are cast from a regular grid plane $P_G$. $P_G$ that is located internal to both the dura mater surface $S_D$ and the prototype implant surface $S_p$. The direction of the ray is identical with the best fitting plane normal vector, n, of the cranial defect margin space curve D. Most of these grids have two hits along each ray that first hits $S_D$ and then $S_p$, or vise versa. White balls indicate where the ray hits $S_D$, and gray balls indicate that with $S_p$. Each volume is tagged as either empty space or penetrated space according to the sequence of ray cast collisions. Step 6 in Table 5.2, defines a metric which is referred to as the volume matrix, V. This n×m matrix will provide information to determine the need for the prototype implant surface modification to correct clinically significant intersections occurring between $S_D$ and $S_p$. Matrix V has elements $V_{ij}$ at the $i^{th}$ row and the $_1$th column derived from the ray casting procedure according to the rule shown in Table 5.3. The volume matrix v can be simultaneously built during the ray-casting process at Step 5.

TABLE 5.3

Rule of Building Volume Matrix V:

1. $V_{ij} = 0$, when less than one collision occurs at the $i^{th}$ row and the $j^{th}$ column point.
2. $V_{ij} = z_{sp} - \alpha \cdot z_{sd}$, when two collisions occur at the $i^{th}$ row and the $j^{th}$ column point of ray cast grid plane, where $z_{sp}$ is the z component (i.e., ray length) of the hit position on $S_P$ and $z_{sd}$ is the z component of the hit position on $S_D$. A constant α scaling factor greater than 1.

The equation used to determine the need for the revision of an implant prototype design is defined as:

$$d = \sum_{i,j} V_{ij} \qquad \text{Equation 5.1}$$

The scalar value d is called the modification coefficient. Table 5.4 presents criteria that are used to interpret the result of above equation.

TABLE 5.4

Interpretation of Modification Coefficient Value d:

1. If $d \leq 0$, then modify the prototype implant surface $S_P$.
2. If $d > 0$, then there is no need to modify $S_P$, since there will be enough open space underneath the implant.

The scaling factor a in Table 5.3 increases the weight of the actual penetrated dura mater volume, thereby penalizing the effective free sub-implant space. Because the cranial soft-tissue structure is not truly elastic, a is set to be greater than 1. Note that when a=1, the approximated difference of the true volumes can be approximated as V=d·w·h, where w and h is width (row interval) and height (i.e., column interval) of each ray cast hexahedral grid element, respectively. The sign of d indicates whether the larger volume exists internally as free space or externally as a dura mater-implant intersected space. Thus, Equation 5.1 calculates a value that is proportional to the volume difference. It also gives d its sign indicating the larger volume between the two, since both w and h cannot have negative measures. The sequence of the collision points between the $S_p$ and $S_D$ will only affect this sign.

Implant Surface Modification Using TPS Warp

If the value of d turns out to be negative, we deform $S_p$ via a thin plate spine (TPS) warp [Book 89]. As discussed above, the TPS surface warp may be considered as a mapping function $f: R^3 \to R^3$, given a set of distinct points in $R^3$ referred to as nodes of interpolation. Thus, homologous surface point pairs that were identified during the volume calculation process in $S_D$ and $S_p$ are used for the warp. The penetrated dura mater points on $S_D$ are set as the warp target points for the corresponding points in $S_p$. Along with these source and target warp point pairs, invariant anchor warp points (see discussion of anchor warp points in Section 4) around the implant rim area. These anchor warp points impose a constraint that does not allow movement of points at the attachment site for proper implant fixation. Technically, points at the edge of $S_p$ are fixed during the TPS warp by setting their source and target warp points as identical.

Implant Taper Creation and Verification

After the final external implant surface is obtained, the implant taper where the contact with defect site occurs is defined. It also closes the external and internal implant surfaces with a connected polygonal mesh that is acceptable as CAD data for RP production.

Determining the Location and Size of the Internal Implant Surface

Figure 28A:
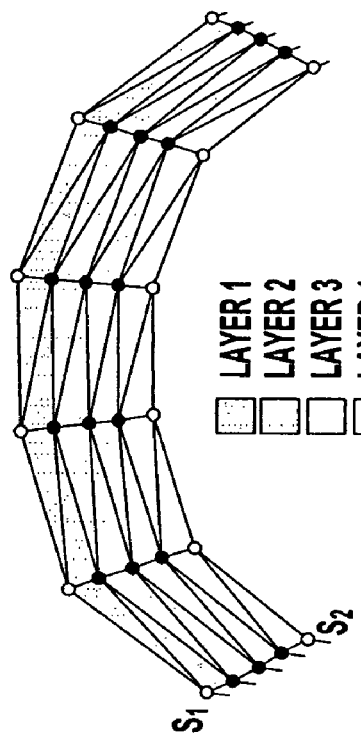
FIGS. 28A-28B shows an implant taper designed in accordance with the present invention.
Figure 28B:
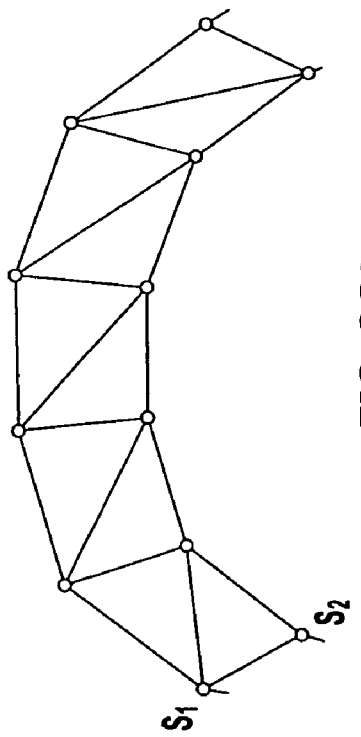

The internal implant surface, $S_2$ is defined by duplicating $S_i$, and then applying two geometric transformations. $P_{S2}$ is denoted as the point set composing $S_2$, and $P_{S1}$ for the point set of $S_1$. A geometric transformation of $P_{S2} = T_T T_S P_{s1}$, is imposed, where $T_S$ is a scaling matrix that shrinks the internal surface, and $T_T$ is a translation matrix that translates the internal surface to be moved below the external surface. The direction of the translation is parallel to the normal vector of the cranial defect margin's best-fitting plane. Note that $S_2$ has the identical the topology structure as $S_1$, since $S_2$ is a uniformly scaled-down and translated version of $S_1$. Thus, a triangle stripe linking the homologous points along the rims of $S_1$ and $S_2$ can be created. This polygonal stripe is the taper (See FIG. 28A which links the internal and external implant surfaces. FIGS. 28A-28B show the implant taper. FIG. 28A shows that the taper is created by adding a polygonal stripe along rim between the external surface, $S_1$, and the internal surface, $S_2$. $S_2$ is a translated and scaled down version of $S_1$. FIG. 28B shows a subdivision of the taper into four layers. Each layer is treated as an independent "polygonal soup" during subsequent implant and cranial attachment site collision detection. The percentage of triangles with collisions is recorded per stripe.

Defining the taper between $S_1$ and $S_2$ results in a closed mesh that can be used for RP production. In terms of the translation of the internal surface, a valid triangulated surface (i.e., a surface free from degenerate triangles) will be created as long as there are no folded surfaces along the direction of the translation. Because the ray direction during the resampling process acquiring $S_1$ was identical to that of the internal surface's translation, any folded surface encountered as a second hit along the ray path must have been removed during the initial resampling process. However, in terms of scaling the internal surface, degenerate triangles can be generated if there is a rapid curvature change near the cranial defect margin.

Implant Taper Verification and Modification

The taper should accurately contact the cranial defect, but should not penetrate surrounding boney structures. We evaluate the amount of taper contact with the patient's polygonal mesh isosurface image is before producing the final implant shape. Once again the RAPID collision detection algorithm is employed to numerically and visually determine the degree of intersection between the tapered edge surface and the defect site. For computational efficiency, the 3D ROI that includes the cranial defect site acquired from the full skull image prior to the cranial defect margin crestline identification step above is reused.

Figure 29:
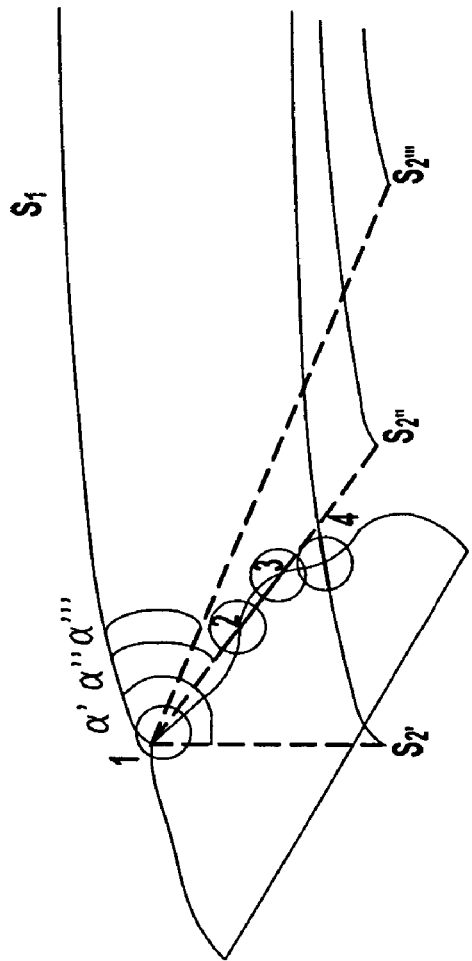
FIG. 29 shows an implant taper angle based on collision detection information in accordance with the present invention.

Although the RAPID algorithm is capable of detecting collisions occurring between pairs of triangles. FIG. 29 depicts intersecting regions between the potential implant taper and the cranial defect site as detected by the RAPID algorithm. The shaded region represents the bony tissue structure of the cranial defect site, where $S_{2'}$, $S_{2''}$, and $S_{2'''}$ are possible specifications of internal implant surfaces generated from decreasing scaling factors. We denote an angle $\alpha$, found between the external implant surface, $S_1$ and the taper, as the taper angle. Without losing contact at the external implant surface, the possibility of penetration decreases as a decreases. The taper angle should not be too small, since the resulting thickness close to upper taper would become unacceptably thin. However, FIG. 29 provides an indirect internal intersection detecting approach by observing collision patterns shown between the taper and the internal surface $S_2$. If the scaling factor is too large, taper angle $\alpha'$ becomes too steep, causing the taper (dashed line) to penetrate into the patient's cranial defect site. In this case, collisions are detected in the circled regions and 4, where region 4 is located on the internal implant surface, $S_{2'}$. In contrast, if the scaling factor is too small, a shallow taper angle $\alpha'''$ is defined, leaving surface contact only at circled region 1, which may result in a loose fit. Finally, if the scaling factor is appropriately chosen for taper angle $\alpha''$, we see collisions at the circled regions 1, 2, and 3 as detected with RAPID the algorithm.

FIG. 29 shows the taper angle determination based on collision pattern. From a single external implant surface $S_1$, the internal implant surfaces $S_{2'}$, $S_{2''}$, and $S_2$ can be defined depending on the scaling factors for $S_2$. The taper (dashed line) between $S_1$ and $S_2$ fully penetrates the cranial defect site (shaded) with a steep taper angle $\alpha'$, while that of $S_1$ and $S_2$ may not result in stable implant seating. The former can be detected by observing no collisions along the taper other than at circled region 1 and a collision in the internal implant surface $S_{2'}$ (circle region 4). The taper between $S_1$ and $S_{2''}$ presents the most desirable collision pattern with an optimal taper angle $\alpha''$, which would show a steadily decreasing pattern of collision (circled region 1, 2, and 3) as the taper gets closer to $S_2$.

This is a simplistic example as one must insure that this type of intersection pattern occurs continuously as one travels radially around the cranial defect margin contour. An intersection pattern showing no collisions at $S_2$, with decreasing frequency of collisions as the taper gets closer to the $S_2$, should be sufficient in most if not all situations, such as those seen in $S_1$-$S_{2''}$ of FIG. 29.

To detect and characterize the degree of contact between the taper and the cranial defect site, the taper is divided into four polygonal stripe layers [see FIG. 28B]. Then, each stripe layer is assigned to a separate group of triangles as its own "polygonal soup" during collision detection with the cranial defect site. FIG. 30 presents a cross-sectional view of possible implant design specifications. FIG. 30 shows the determination of implant thickness and taper. The thin dashed lines depict alternative tapers based on varying translation and scaling factors. Between external surface, $S_1$, and internal surface, $S_2$, thick dashed lines represent the possible taper locations. Shaded areas represent areas of penetration of potential tapers into the cranial defect site. Note that according to this figure, the taper angle is not only dependent upon the scaling factor, but also on the translation factor.

Thus, if adjustment of the taper angle is necessary, both translation and scaling factors may be interactively altered by the operator. A reasonable combination of these factors can be sought so that the degree of intersection will decline from the outer to the inner layer of the taper. Feedback from the RAPID collision detection algorithm is color-encoded to visually discriminate the relative number of collided triangles. The percentage of area contacting the cranial defect in each layer is calculated by counting the number of collided triangles versus the total number of triangles composing the stripe.

Novel Medical CAD Algorithms

The present invention introduces a top-down approach to the CAD of a cranial implant. Fo 11 ur aspects of the invention include: 1) detection of a cranial defect margin crestline; 2)

interpolation of a skull template surface into the cranial defect; 3) skull template surface smoothing and its articulation with the cranial defect margin crestline; and 4) validation of the final implant's taper, thickness, and overall fit (i.e., non-intersection with the patient).

Besides adopting known algorithms to a cranial implant CAD system, the present invention presents the following new algorithms.

- Principal curvature calculation of vertices in a polygonal mesh isosurface image.
- Detection of a cranial defect margin crestline via the minimum cost path search of a graph representing a 3D skull isosurface image.
- Cranial defect margin space curve smoothing and Catmull-Rom spline encoding.
- Use of a mirrored or an average skull template surface for the CAD of a cranial implant surface.
- Automated globally distributed homologous landmark detection, as well as anchor warp points for the second pass local TPS warp.
- Regular polygonal mesh resampling and smoothing that removes CT slice-edge artifact from left-right mirrored skull templates.
- Quadrilateral surface patch partitioning along a space curve that approximates the cranial defect margin crestline.
- Validation of prototype cranial implant surface and taper fit with adjacent skull and soft tissue structures prior to RP production.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, circuits, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A computer-aided design method for producing an implant for a patient prior to operation, the method comprising:
   generating digital image data with a non-invasive three-dimensional (3D) volume scan of an anatomical region of the patient comprising a defect site that is to receive the implant;
   generating a polygonal-mesh 3D surface image representing the anatomical region of the patient based on the digital image data;
   defining a defect margin crestline describing the external boundary of the patient's defect based on a curvature estimation on the polygonal-mesh 3D surface image;
   generating a digital template of desired anatomy associated with the anatomical region;
   performing a two-pass thin plate spline (TPS) warp on the digital template to register the digital template specifically to the patient;
   generating a prototype implant surface based on the defect margin crestline and the registered template of the anatomical region, the prototype implant surface defining an outer surface of a 3D digital model of the implant;
   generating at least one internal surface and at least one connecting surface with respect to the prototype implant surface to generate the 3D digital model of the implant; and
   fabricating the implant based on the 3D digital model of the implant.

2. The method of claim 1, wherein the polygonal-mesh 3D surface image is of an entirety of the anatomical region that is represented by the digital image data, the method further comprising:
   determining a 3D region of interest (ROI) on the polygonal-mesh 3D surface image of the anatomical region that includes only a region of the polygonal-mesh 3D surface image immediately adjacent to and surrounding the defect site; and
   extracting the 3D ROI from the polygonal-mesh 3D surface image to generate a polygonal-mesh 3D surface image file of the 3D ROI;
   wherein defining the defect margin crestline comprises defining the defect margin crestline on the 3D ROI.

3. The method of claim 2, wherein determining the 3D ROI comprises:
   placing a plurality of seed landmarks in the region of the polygonal-mesh 3D surface image immediately adjacent to the defect site such that the seed landmarks are coplanar to define a best-fitting plane;
   connecting consecutive ones of the plurality of seed landmarks based on a line equation; and
   defining the 3D ROI as a 3D area of the polygonal-mesh 3D surface image that is enclosed within the connected plurality of seed landmarks.

4. The method of claim 1, wherein defining the defect margin crestline comprises:
   determining a 3D surface curvature at each respective 3D surface point of the polygonal-mesh 3D surface image to generate the curvature estimate; and
   generating color values corresponding to a magnitude of the 3D surface curvature at each respective 3D surface point of the polygonal-mesh 3D surface image.

5. The method of claim 4, wherein determining the 3D surface comprises:
   defining an arc length between predefined starting and ending points defining a specified arc length for a parametric space curve along the polygonal-mesh 3D surface image; and
   calculating a unit vector perpendicular to a tangent of the parametric space curve at each respective 3D surface point.

6. The method of claim 4, further comprising redistributing the color values in a histogram over an entire intensity scale to ascertain contrasts between low and high curvature of the respective 3D surface points.

7. The method of claim 4, further comprising:
   placing seed landmarks at 3D surface points having highest curvature magnitudes based on the color values;
   forming sectors on the polygonal-mesh 3D surface image based on the seed landmarks; and
   executing a minimum-cost path traversal algorithm in each sector to determine a series of points defining the defect margin crestline.

8. The method of claim 1, wherein generating the digital template of the anatomical region comprises generating the digital template based on one of left-right mirroring of the anatomical region and providing a digital template that is an average of the anatomical region imaged on a plurality of patients.

9. The method of claim 8, wherein generating the digital template comprises implementing left-right mirroring of the anatomical region in response to the defect site being unilateral with respect to a plane separating left and right sides of the patient.

10. The method of claim 8, wherein generating the digital template comprises providing an average of the anatomical region that is an appropriate size and reoriented for a reference frame of the patient in response to the defect site spanning a plane separating left and right sides of the patient.

11. The method of claim 1, wherein generating the at least one internal surface and the at least one connecting surface comprises extending the prototype implant surface such that it spans a thickness of a body structure of the patient underlying the defect margin crestline based on the polygonal-mesh 3D surface image.

12. The method of claim 11, wherein extending the prototype implant surface comprises:
casting geometric rays from each point of the defect margin crestline internally in a normal direction of a best-fitting plane of seed landmarks that defines a 3D region of interest (ROI) of the anatomical region that includes the defect site; and
calculating a Euclidean distance between an origin of each geometric ray and the best-fitting plane.

13. The method of claim 1, wherein the prototype implant surface is configured as a triangular-mesh isosurface image, the method further comprising:
resampling the prototype implant surface to uniformly shape and space triangles associated with the triangular-mesh isosurface image;
implementing a surface smoothing algorithm to remove slice-edge artifact from the resampled prototype implant surface; and
implementing an articulation algorithm to articulate the surface-smoothed and resampled prototype implant surface to fit the defect margin crestline.

14. The method of claim 13, wherein implementing the surface smoothing algorithm comprises removing slice edge artifact in response to volume image slices having an inter-slice dimension that is larger than an in-slice pixel dimension.

15. The method of claim 1, wherein generating the at least one internal surface and the at least one connecting surface comprises generating connecting surfaces between the prototype implant surface and the internal surface with a taper-fit surface that is tapered between the prototype implant surface and the internal surface.

16. The method of claim 15, further comprising validating the 3D digital model of the implant with respect to contact of the taper-fit surface and the internal surface with adjacent bone and soft tissue structures prior to fabricating the implant.

17. The method of claim 16, wherein validating the 3D digital model of the implant comprises implementing a collision detection algorithm to verify seating of the taper-fit surface with adjacent bone structure and to verify non-collision with adjacent had and soft tissues.

18. The method of claim 1, further comprising selecting the defect site of the patient from at least one of a hard tissue element and a soft tissue element.

19. The method of claim 1, further comprising selecting the defect site of the patient as a cranial defect associated with the skull of the patient.

* * * * *

UNITED STATES PATENT AND TRADEMARK OFFICE
CERTIFICATE OF CORRECTION

| | | |
|---|---|---|
| PATENT NO. | : 7,747,305 B2 | Page 1 of 1 |
| APPLICATION NO. | : 11/299138 | |
| DATED | : June 29, 2010 | |
| INVENTOR(S) | : David Dean and Kyoung-June Min | |

It is certified that error appears in the above-identified patent and that said Letters Patent is hereby corrected as shown below:

Column 1, line 13,
After the CROSS-REFERENCE TO RELATED APPLICATIONS section and before the TECHNICAL FIELD section add:

"FEDERAL FUNDING NOTICE
This invention was made with government support under grants R01-DE013740 and R43-DE013786 awarded by the National Institutes of Health. The government has certain rights in the invention."

Signed and Sealed this
First Day of February, 2011

David J. Kappos
*Director of the United States Patent and Trademark Office*